United States Patent
Bentley et al.

(10) Patent No.: US 7,253,281 B2
(45) Date of Patent: Aug. 7, 2007

(54) ANTI-OBESITY 1,2,3,4,10,10A-HEXAHYDROPYRAZINO[1,2-A] INDOLES

(75) Inventors: Jonathan Mark Bentley, Reading (GB); Paul Hebeisen, Basel (CH); Patrizio Mattei, Riehen (CH); Marc Muller, Saint-Louis (FR); Hans Richter, Grenzach-Wyhlen (DE); Stephan Roever, Inzlingen (DE); Sven Taylor, Riedisheim (FR)

(73) Assignees: Hoffmann-La Roche Inc., Nutley, NJ (US); Vernalis Research Limited, Winnersh, Wokingham (GB)

( * ) Notice: Subject to any disclaimer, the term of this patent is extended or adjusted under 35 U.S.C. 154(b) by 0 days.

(21) Appl. No.: 11/169,079

(22) Filed: Jun. 28, 2005

(65) Prior Publication Data

US 2005/0239789 A1    Oct. 27, 2005

Related U.S. Application Data

(63) Continuation of application No. 10/396,242, filed on Mar. 25, 2003, now Pat. No. 6,933,387, which is a continuation of application No. 09/912,949, filed on Jul. 25, 2001, now abandoned.

(30) Foreign Application Priority Data

Jul. 31, 2000  (EP) .................................. 00116517

(51) Int. Cl.
  *C07D 487/04*   (2006.01)
  *A61K 31/4985*  (2006.01)

(52) U.S. Cl. ..................... 544/344; 514/250

(58) Field of Classification Search ................ 544/344; 514/250

See application file for complete search history.

(56) References Cited

U.S. PATENT DOCUMENTS

| 3,317,524 | A | 5/1967 | Freed et al. |
| 5,432,177 | A | 7/1995 | Baker et al. |
| 5,576,319 | A | 11/1996 | Baker et al. |
| 5,622,950 | A | 4/1997 | Baker et al. |
| 6,552,018 | B1 | 4/2003 | Ejima et al. |
| 6,800,627 | B1 * | 10/2004 | Adams et al. ............... 514/250 |
| 6,933,387 | B2 * | 8/2005 | Bentley et al. ............. 544/344 |

FOREIGN PATENT DOCUMENTS

| DE | 2 162 422 | 6/1973 |
| EP | 0572863 | 12/1993 |
| JP | 60279442 | 10/1994 |
| JP | 2000-169475 | 6/2000 |
| WO | WO 0035922 | 6/2000 |
| WO | WO 00/44753 | 8/2000 |

* cited by examiner

*Primary Examiner*—Emily Bernhardt
(74) *Attorney, Agent, or Firm*—George W. Johnston; Dennis P. Tramaloni; Samuel H. Megerditchian

(57) ABSTRACT

The present invention is directed to 1,2,3,4,10,10a,-hexahydropyrazino[1,2-a]indole derivatives as well as pharmaceutically acceptable salts, solvates and esters thereof, wherein $R^1$ to $R^8$ have the significance given in claim 1 be used in the form of pharmaceutical preparations for the treatment or prevention of disorders of the central nervous system, damage to the central nervous system, cardiovascular disorders, gastrointestinal disorders, diabetes insipidus, obesity and sleep apnea.

8 Claims, No Drawings

ANTI-OBESITY 1,2,3,4,10,10A-HEXAHYDROPYRAZINO[1,2-A] INDOLES

CONTINUITY INFORMATION

This application is a continuation of Ser. No. 10/396,242, filed Mar. 25, 2003, (issued as U.S. Pat. No. 6,933,387), which is a continuation of Ser. No. 09/912,949, filed Jul. 25, 2001, which is abandoned.

BACKGROUND OF THE INVENTION

It has been recognised that obesity is a disease process influenced by environmental factors in which the traditional weight loss methods of dieting and exercise need to be supplemented by therapeutic products (S. Parker, "*Obesity: Trends and Treatments*", Scrip Reports, PJB Publications Ltd, 1996).

Whether someone is classified as overweight or obese is generally determined on the basis of their body mass index (BMI) which is calculated by dividing body weight (kg) by height squared (m$^2$). Thus, the units of BMI are kg/m$^2$ and it is possible to calculate the BMI range associated with minimum mortality in each decade of life. Overweight is defined as a BMI in the range 25–30 kg/m$^2$, and obesity as a BMI greater than 30 kg/m$^2$. There are problems with this definition in that it does not take into account the proportion of body mass that is muscle in relation to fat (adipose tissue). To account for this, obesity can also be defined on the basis of body fat content: greater than 25% and 30% in males and females, respectively.

As the BMI increases there is an increased risk of death from a variety of causes that is independent of other risk factors. The most common diseases with obesity are cardiovascular disease (particularly hypertension), diabetes, including Type I and Type II diabetes, (obesity aggravates the development of diabetes), gall bladder disease (particularly cancer) and diseases of reproduction. Research has shown that even a modest reduction in body weight can correspond to a significant reduction in the risk of developing coronary heart disease.

Compounds marketed as anti-obesity agents include Orlistat (XENICAL®) and Sibutramine. Orlistat (a lipase inhibitor) inhibits fat absorption directly and tends to produce a high incidence of unpleasant (though relatively harmless) side-effects such as diarrhoea. Sibutramine (a mixed 5-HT/noradrenaline reuptake inhibitor) can increase blood pressure and heart rate in some patients. The serotonin releaser/reuptake inhibitors fenfluramine (Pondimin®) and dexfenfluramine (Redux™) have been reported to decrease food intake and body weight over a prolonged period (greater than 6 months). However, both products were withdrawn after reports of preliminary evidence of heart valve abnormalities associated with their use. There is therefore a need for the development of a safer anti-obesity agent.

The non-selective 5-HT$_{2C}$ receptor agonists/partial agonists m-chlorophenylpiperazine (mCPP) and trifluoromethylphenylpiperazine (TFMPP) have been shown to reduce food intake in rats (G. A. Kennett and G. Curzon, *Psychopharmacol.*, 1988, 96, 93–100; G. A. Kennett, C. T. Dourish and G. Curzon, *Eur. J. Pharmacol.*, 1987, 141, 429–435) and to accelerate the appearance of the behavioural satiety sequence (S. J. Kitchener and C. T. Dourish, *Psychopharmacol.*, 1994, 113, 369–377). Recent findings from studies with mCPP in normal human volunteers and obese subjects have also shown decreases in food intake. Thus, a single dose of mCPP decreased food intake in female volunteers (A. E. S. Walsh et al, *Psychopharmacol.*, 1994, 116, 120–122) and decreased the appetite and body weight of obese male and female subjects during subchronic treatment for a 14 day period (P. A. Sargeant et al., *Psychopharmacol.*, 1997, 133, 309–312). The anorectic action of mCPP is absent in 5-HT$_{2C}$ receptor knockout mutant mice (L. H. Tecott et al., *Nature*, 1995, 374, 542–546) and is antagonised by the 5-HT$_{2C}$ receptor antagonist SB-242084 in rats (G. A. Kennett et al., *Neuropharmacol.*, 1997, 36, 609–620). It seems therefore that mCPP decreases food intake via an agonist action at the 5-HT$_{2C}$ receptor.

Other compounds which have been proposed as 5-HT$_{2C}$ receptor agonists for use in the treatment of obesity include the substituted 1-aminoethyl indoles disclosed in EP-A-0655440. CA-2132887 and CA-2153937 disclose that tricyclic 1-aminoethylpyrrole derivatives and tricyclic 1-aminoethyl pyrazole derivatives bind to 5-HT$_{2C}$ receptors and may be used in the treatment of obesity. WO-A-98/30548 discloses aminoalkylindazole compounds as 5-HT$_{2C}$ agonists for the treatment of CNS diseases and appetite regulation disorders. 2-(2,3-Dihydro-1H-pyrrolo[1,2-a]indol-9-yl)ethylamine is disclosed in *J. Med. Chem.*, 1965, 8, 700. The preparation of pyrido[1,2-a]indoles for the treatment of cerebrovascular disorders is disclosed in EP-A-0252643 and EP-A-0167901. The preparation of 10-[(acylamino)ethyl] tetrahydropyrido[1,2-a]indoles as anti-ischemic agents is disclosed in EP-A-0279125.

It is an object of this invention to provide selective, directly acting 5HT$_2$ receptor ligands for use in therapy and particularly for use as anti-obesity agents. It is a further object of this invention to provide directly acting ligands selective for 5-HT$_{2B}$ and/or 5-HT$_{2C}$ receptors, for use in therapy and particularly for use as anti-obesity agents. It is a further object of this invention to provide selective, directly acting 5-HT$_{2C}$ receptor ligands, preferably 5-HT$_{2C}$ receptor agonists, for use in therapy and particularly for use as anti-obesity agents.

SUMMARY OF INVENTION

The invention is concerned particularly with compounds of formula I and their pharmaceutically acceptable salts, solvates and esters

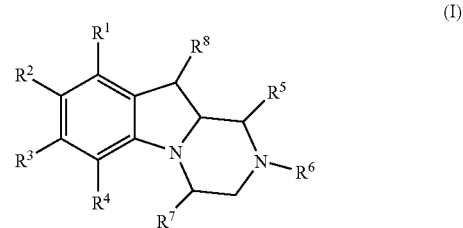

(I)

wherein
R$^1$, R$^2$, R$^3$ and R$^4$ are independently hydrogen, halogen, hydroxy, alkyl, cycloalkyl, aralkyl, aryl, alkoxy, alkoxy alkyl, hydroxy alkyl, alkoxy alkoxy alkyl, hydroxyalkoxy alkyl, halo alkyl, halo alkoxy, aryloxy, alkylcarbonyl, arylcarbonyl, alkylthio, arylthio, alkylsulfoxyl, arylsulfoxyl, alkylsulfonyl, arylsulfonyl, amino, nitro, cyano, alkoxycarbonyl, aryloxycarbonyl, alkylaminocarbonyl, dialkylaminocarbonyl, alkylcarbonylamino, carboxy, heterocyclyl or R$^3$ and R$^4$ form together with the carbon atoms to which they are attached form a 5- to 7-membered carbocyclic ring which ring is unsubstituted or alkyl substituted;

$R^5$ is hydrogen, alkyl or cycloalkyl;

$R^6$ is hydrogen, alkyl, hydroxy alkyl, carbamoyl alkyl, alkoxycarbonyl alkyl, aryloxycarbonyl alkyl or —$(CH_2)_n$-A;

$R^7$ is hydrogen, alkyl, cycloalkyl, hydroxyalkyl or alkoxyalkyl, whereby $R^7$ is not hydrogen when $R^6$ is hydrogen, alkyl, cycloalkyl or 1H-pyrrolo(2,3-b)pyridin-3-ylmethyl;

$R^8$ is hydrogen, alkyl or cycloalkyl;

A is a heterocyclyl or cycloalkyl ring which ring can be unsubstituted or substituted on a ring carbon atom with a hydroxy, carboxy, oxo, alkanoyloxy alkyl, aryloxycarbonyl or alkylcarbamoyl substituent;

n is 0, 1, 2 or 3;

are selectively active 5-HT$_2$ receptor agonists for use in treating obesity and in the use in treating Type I and Type II diabetes.

DETAILED DESCRIPTION

Among the preferred compounds of this invention are compounds of the formula

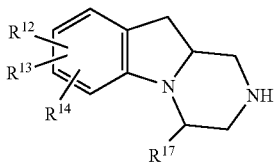

I-A wherein $R^{12}$, $R^{13}$ and $R^{14}$ are independently hydrogen, halogen, trifluoromethyl, lower alkyl, lower alkoxy lower alkyl, lower alkoxy-lower alkoxy lower alkyl, halo lower alkoxy, lower alkyl aminocarbonyl, di-lower alkyl aminocarbonyl or cyano and $R^{17}$ is lower alkyl or hydroxy lower alkyl;

compounds of the formula

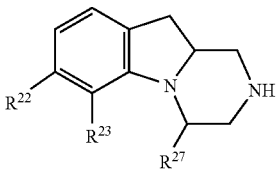

I-B wherein one of $R^{22}$ and $R^{23}$ is hydrogen and the other is hydroxy lower alkyl, alkyl lower-alkylaminocarbonyl, di-lower alkylaminocarbonyl, alkoxy lower alkyl, lower alkylcarbonylamino or lower alkoxy-lower alkoxy lower alkyl; or $R^{22}$ and $R^{23}$ taken together with the carbon atoms to which they are added to form a 4- to 6-membered saturated carbocyclic ring which ring is unsubstituted or lower alkyl substituted and $R^{27}$ is lower alkyl;

and compounds of the formula

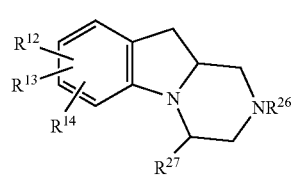

I-C wherein $R^{12}$, $R^{13}$ and $R^{14}$ are independently hydrogen, halogen, trifluoromethyl, lower alkyl, lower alkoxy lower alkyl, lower alkoxy lower alkoxy lower alkyl, halo lower alkoxy, lower alkyl aminocarbonyl or di-lower alkyl aminocarbonyl, cyano; $R^{17}$ is lower alkyl or hydroxy-lower alkyl and $R^{26}$ is $(CH_2)_n$-Y, hydroxy lower alkyl, lower alkoxycarbonyl lower alkyl or carbamoyl lower alkyl;

Y is a saturated 3- to 6-membered carbocyclic ring or a 5- to 7-membered heterocyclic ring containing at most two hetero atoms selected from the group consisting of oxygen, sulfer or nitrogen, which rings can be unsubstituted or substituted on a ring carbon atom with an oxo; and n is 0, 1, 2 or 3.

The compounds of formula I were all active as 5-HT$_2$ receptor agonists as determined by the Assay Procedures A-D hereinafter described. In view of this activity, the compounds of this invention are active in treating obesity and diseases related to obesity such as those mentioned hereinbefore and particularly diabetes including Type I and Type II diabetes.

In the present description the term "alkyl", alone or in combination, signifies a straight-chain or branched-chain alkyl group with 1 to 8 carbon atoms, preferably a straight or branched-chain alkyl group with 1–4 carbon atoms. Examples of straight-chain and branched $C_1$–$C_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl, ethyl, propyl and isopropyl. Particularly preferred are methyl and ethyl. The preferred alkyl groups are lower alkyl groups containing from 1 to 6 carbon atoms.

The term "cycloalkyl" or "carbocyclic" ring, alone or in combination, signifies a saturated cycloalkyl ring with 3 to 8, preferably 3 to 6 carbon atoms and most preferably a cycloalkyl ring with 4 to 6 carbon atoms. Examples of $C_3$–$C_8$ cycloalkyl are cyclopropyl, methyl-cyclopropyl, dimethylcyclopropyl, cyclobutyl, methyl-cyclobutyl, cyclopentyl, methyl-cyclopentyl, cyclohexyl, methylcyclohexyl, dimethyl-cyclohexyl, cycloheptyl and cyclooctyl, preferably cyclopropyl and particularly cyclopentyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec.butoxy and tert.butoxy, preferably methoxy and ethoxy. The preferred alkoxy group is a lower alkoxy? group containing from 1 to 6 carbon atoms.

The term "aryloxy", alone or in combination, signifies a group of the formula aryl-O—. Phenyloxy is an example of such an aryloxy group. The preferred aryl group is phenyl.

The term "haloalkyl", alone or in combination, signifies an alkyl group as previously defined, with lower alky being preferred, wherein one or several hydrogen atoms, preferably one hydrogen atom have/has been replaced by halogen. Examples of haloalkyl groups are trifluoromethyl, pentafluoroethyl and trichloromethyl. Preferred examples are trifluoromethyl and difluoromethyl.

The term "haloalkoxy", alone or in combination, signifies an alkoxy group, with lower alkoxy being preferred, as previously defined, wherein one or several hydrogen atoms, preferably one hydrogen atom have/has been replaced by halogen. Examples of haloalkoxy groups are trifluoromethoxy, pentafluoroethoxy and trichloromethoxy. A preferred example is trifluoromethoxy.

The term "carbonyl" refer to a group of the formula —C(O)—. The term alkanoyl designates a monovalent alkanoyl substituent derived from an aliphatic hydrocarbon carboxylic acids having the terminal hydroxy group of the carboxylic acid moiety removed. The monovalent alkanoyl groups contain from 2 to 10 carbon atoms with lower alkanoyl groups containing from 2 to 7 carbon atoms being preferred.

The term "alkylthio", alone or in combination, signifies a group of the formula alkyl-S— in which the term "alkyl" has the previously given significance, such as methylthio, ethylthio, n-propylthio, isopropylthio. Preferred are methylthio and ethylthio.

The term "arylthio", alone or in combination, signifies a group of the formula aryl-S— in which the term "aryl" has the previously given significance. Phenylthio is an example of such an arylthio group.

The term "sulphonyl", alone or in combination, signifies a group of the formula

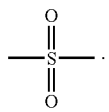

The term "sulfoxyl", alone or in combination, signifies a group of the formula

The term "aryl", alone or in combination, signifies a phenyl or naphthyl group which optionally carries one to three substituents each independently selected from alkyl, alkoxy, halogen, carboxy, alkoxycarbonyl, aminocarbonyl, hydroxy, amino, nitro and the like, such as phenyl, p-tolyl, 4-methoxyphenyl, 4-tert.butoxyphenyl, 4-fluorophenyl, 2-chlorophenyl, 3-chlorophenyl, 4-chlorophenyl, 4-hydroxyphenyl, 1-naphthyl and 2-naphthyl. Preferred are phenyl, 4-fluorophenyl, 1-naphthyl and 2-naphthyl and particularly phenyl.

The term "heterocyclyl", alone or in combination, signifies either a saturated 4- to 7-membered heterocyclic ring, partially unsaturated or aromatic 5- to 10-membered heterocycle, preferably a 5- or 6-membered ring. The heterocyclic ring can contain from one to three hetero atoms selected from nitrogen, oxygen and sulphur. Generally, such rings containing from one to 2 heteroatoms are preferred, with one heteroatom being particularly preferred. If desired, they can be substituted on one to three carbon atoms by halogen, alkyl, alkoxy, oxo etc. and/or on a secondary nitrogen atom (i.e. —NH—) by alkyl, cycloalkyl, aralkoxycarbonyl, alkanoyl, phenyl or phenylalkyl or on a tertiary nitrogen atom (i.e.=N—) by oxido, with halogen, alkyl, cycloalkyl and alkoxy being preferred. Examples of such heterocyclyl groups are pyrrolidinyl, piperidinyl, piperazinyl, morpholinyl, thiomorpholinyl, pyrazoyl, imidazoyl (e.g. imidazol-4-yl and 1-benzyloxycarbonyl-imidazol-4-yl), pyrazoyl, pyridyl, pyrazinyl, pyrimidinyl, hexahydro-pyrimidinyl, furyl, thienyl, thiazolyl, oxazolyl, indolyl (e.g. 2-indolyl), quinolyl (e.g. 2-quinolyl, 3-quinolyl and 1-oxido-2-quinolyl), isoquinolyl (e.g. 1-isoquinolyl and 3-isoquinolyl), tetrahydroquinolyl (e.g. 1,2,3,4-tetrahydro-2-quinolyl), 1,2,3,4-tetrahydroisoquinolyl (e.g. 1,2,3,4-tetrahydro-1-oxo-isoquinolyl) and quinoxalinyl. Preferred are oxazolidinone, cyclobutanonyl, [1,2,4]triazol-3-yl, [1,2,4]oxadiazol-3-yl, [1,2,4]triazol-3-one-5-yl, tetrazolyl, [1,3,4]oxadiazol-2-yl, [1,3,4]thiadiazol-2-yl, 1H-imidazol-2-yl, 1H-imidazol-4-yl. Particularly preferred examples for heterocyclyl are [1,2,4]oxadiazol-3-yl or cyclobutanon-2-yl.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substitutents together forming a ring, such as, for example, —NH$_2$, methylamino, ethylamino, dimethylamino, diethylamino, methyl-ethylamino, pyrrolidin-1-yl or piperidino etc., preferably amino, dimethylamino and diethylamino and particularly primary amino.

The term "halogen" signifies fluorine, chlorine, bromine or iodine and preferably fluorine, chlorine or bromine and particularly chlorine and bromine.

The term "carboxy", alone or in combination, signifies a —COOH group.

The term "carboxyalkyl" alone or in combination, signifies an alkyl group as previously described in which one hydrogen atom has been replaced by a carboxy group. The carboxymethyl group is preferred and particularly carboxyethyl.

The term "carbamoyl" refers to a group of the formula amino-C(O)—.

The term "cycloalkanonyl" refers to a cycloalkyl ring, wherein one carbon ring atom has been replaced by a —C(O)— group. In this manner, cycloalkanoyl designates a saturated carbocyclic ring which is substituted on one ring carbon atom with an oxo group. Preferably, the ring contains from 3 to 6 ring members and most perferably 4 to 6 ring members.

Compounds of formula I, wherein R$^3$ and R$^4$ form together with the carbon atoms to which they are attached a 5-to 7-membered carbocyclic ring, which is optionally substituted by alkyl comprise one of the following moieties IAA, IBB or ICC:

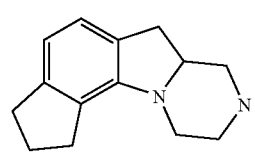

IAA

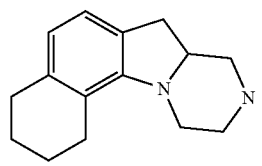

IBB

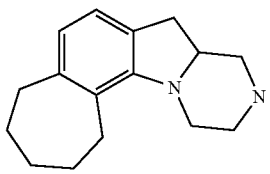

ICC

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared form addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions.

The invention expressly includes pharmaceutically acceptable salts, esters and solvates of compounds according to formula I which includes compounds of formuae I-A, I-B and I-C. The compounds of formula I can be solvated, e.g. hydrated. The solvation can be effected in the course of the manufacturing process or can take place e.g. as a consequence of hygroscopic properties of an initially anhydrous compound of formula I (hydration). The term pharmaceutically acceptable salts also includes physiologically acceptable solvates.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

In more detail, for example, the COOH groups of compounds according to formula I can be esterified. The alkyl and aralkyl esters are examples of suitable esters. The methyl, ethyl, propyl, butyl and benzyl esters are preferred esters. The methyl and ethyl esters are especially preferred. Further examples of pharmaceutically usable esters are compounds of formula I, wherein the hydroxy groups can be esterified. Examples of such esters are formate, acetate, propionate, butyrate, isobutyrate, valerate, 2-methylbutyrate, isovalerate and N,N-dimethylaminoacetate. Preferred esters are acetate and N,N-dimethylaminoacetate.

The term "lipase inhibitor" refers to compounds which are capable of inhibiting the action of lipases, for example gastric and pancreatic lipases. For example orlistat and lipstatin as described in U.S. Pat. No. 4,598,089 are potent inhibitor of lipases. Lipstatin is a natural product of microbial origin, and orlistat is the result of a hydrogenation of lipstatin. Other lipase inhibitors include a class of compound commonly referred to as panclicins. Panclicins are analogues of orlistat (Mutoh et al, 1994). The term "lipase inhibitor" refers also to polymer bound lipase inhibitors for example described in International Patent Application WO99/34786 (Geltex Pharmaceuticals Inc.). These polymers are characterized in that they have been substituted with one or more groups that inhibit lipases. The term "lipase inhibitor" also comprises pharmaceutically acceptable salts of these compounds. The term "lipase inhibitor" preferably refers to orlistat.

Orlistat is a known compound useful for the control or prevention of obesity and hyperlipidemia. See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122 and WO 00/09123. Additional processes for the preparation of orlistat are disclosed in European Patent Applications Publication Nos. 185,359, 189,577, 443,449, and 524,495.

Orlistat is preferably orally administered from 60 to 720 mg per day in divided doses two to three times per day. Preferred is wherein from 180 to 360 mg, most preferably 360 mg per day of a lipase inhibitor is administered to a subject, preferably in divided doses two or, particularly, three times per day. The subject is preferably an obese or overweight human, i.e. a human with a body mass index of 25 or greater. Generally, it is preferred that the lipase inhibitor be administered within about one or two hours of ingestion of a meal containing fat. Generally, for administering a lipase inhibitor as defined above it is preferred that treatment be administered to a human who has a strong family history of obesity and has obtained a body mass index of 25 or greater.

Orlistat can be administered to humans in conventional oral compositions, such as, tablets, coated tablets, hard and soft gelatin capsules, emulsions or suspensions. Examples of carriers which can be used for tablets, coated tablets, dragees and hard gelatin capsules are lactose, other sugars and sugar alcohols like sorbitol, mannitol, maltodextrin, or other fillers; surfactants like sodium lauryle sulfate, Brij 96, or Tween 80; disintegrants like sodium starch glycolate, maize starch or derivatives thereof; polymers like povidone, crospovidone; talc; stearic acid or its salts and the like. Suitable carriers for soft gelatin capsules are, for example, vegetable oils, waxes, fats, semi-solid and liquid polyols and the like. Moreover, the pharmaceutical preparations can contain preserving agents, solubilizers, stabilizing agents, wetting agents, emulsifying agents, sweetening agents, coloring agents, flavoring agents, salts for varying the osmotic pressure, buffers, coating agents and antioxidants. They can also contain still other therapeutically valuable substances. The formulations may conveniently be presented in unit dosage form and may be prepared by any methods known in the pharmaceutical art. Preferably, orlistat is administered according to the formulation shown in the Examples and in U.S. Pat. No. 6,004,996, respectively.

The compounds of formula I can contain several asymmetric centres and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluent).

Preferred compounds according to formula I are those, wherein $R^1$, $R^2$, $R^3$ and $R^4$ are independently selected from hydrogen, halogen, hydroxy, alkyl, cycloalkyl, aralkyl, aryl, alkoxy, alkoxyalkyl, haloalkyl, aryloxy, alkylcarbonyl, arylcarbonyl, alkylthio, arylthio, alkylsulfoxyl, arylsulfoxyl, alkylsulfonyl, arylsulfonyl, amino, nitro, cyano, alkoxycarbonyl, aryloxycarbonyl, alkylaminocarbonyl, dialkylaminocarbonyl, alkylcarbonylamino, carboxy or heterocyclyl;

$R^5$ is hydrogen, alkyl or cycloalkyl;

$R^6$ is hydrogen, alkyl, cycloalkyl, hydroxyalkyl, carbamoylalkyl, alkoxycarbonylalkyl, aryloxycarbonylalkyl or —$(CH_2)_n$-A;

$R^7$ is hydrogen, alkyl or cycloalkyl, whereby $R^7$ is not hydrogen when $R^6$ is hydrogen, alkyl, cycloalkyl or 1H-pyrrolo(2,3-b)pyridin-3-ylmethyl;

$R^8$ is hydrogen;

A is heterocyclyl, cycloalkanonyl or cycloalkyl substituted with hydroxy, carboxy, alkyloxycarbonyl, aryloxycarbonyl or carbamoyl;

n is 0, 1, 2 or 3;

and their pharmaceutically usable salts, solvates and esters.

Preferred compounds according to formula I are those, wherein $R^1$, $R^2$, $R^3$ and $R^4$ are independently selected from hydrogen, halogen, hydroxy, alkyl, cycloalkyl, aralkyl, aryl, alkoxy, alkoxyalkyl, haloalkyl, aryloxy, alkylcarbonyl, arylcarbonyl, alkylthio, arylthio, alkylsulfoxyl, arylsulfoxyl, alkylsulfonyl, arylsulfonyl, amino, nitro, cyano, alkoxycarbonyl, aryloxycarbonyl, alkylaminocarbonyl, dialkylaminocarbonyl, alkylcarbonylamino, carboxy or heterocyclyl. Also preferred are compounds according to formula I, wherein $R^3$ and $R^4$ form together with the carbon atoms to which they are attached a 5-membered carbocyclic ring otionally substituted by alkyl, wherein these compounds compise the moiety of formula IA.

Further preferred compounds according to formula I are those, wherein $R^1$, $R^2$, $R^3$ and $R^4$ are independently selected from hydrogen, halogen, alkyl, alkoxy, haloalkyl, haloalkoxy and cyano. Particularly preferred compounds of formula I are those, wherein one or two of $R^1$, $R^2$, $R^3$ and $R^4$ are independently selected from chloro, bromo, methyl, trifluoromethyl and cyano and the others are hydrogen.

Preferred compounds of formula I are those, wherein $R^5$ is hydrogen, alkyl or cycloalkyl. Another preferred embodiment of the invention comprises compounds of formula I, wherein $R^5$ is hydrogen or alkyl. Particularly preferred are compounds according to formula I, wherein $R^5$ is hydrogen.

Further preferred compounds according to formula I are those, wherein $R^6$ is hydrogen, alkyl, cycloalkyl, hydroxyalkyl, carbamoylalkyl, alkoxycarbonylalkyl, aryloxycarbonylalkyl or —$(CH_2)_n$-A. Particularly preferred are those compounds of formula I, wherein $R^6$ is hydrogen, hydroxyalkyl, carbamoylalkyl, alkyloxycarbonylalkyl or —$(CH_2)_n$-A. Very preferred are compounds of formula I, wherein $R^6$ is hydrogen.

A further preferred embodiment of the present invention are the compounds according to formula I, wherein A is oxazolidinone, cyclobutanonyl, [1,2,4]triazol-3-yl, [1,2,4]oxadiazol-3-yl, [1,2,4]triazol-3-one-5-yl, tetrazolyl, [1,3,4]oxadiazol-2-yl, [1,3,4]thiadiazol-2-yl, 1H-imidazol-2-yl or 1H-imidazol-4-yl. Particularly preferred are 2-oxazolidin-2-one and cyclobutanon-2-yl.

Moreover, preferred are those compounds, wherein A is cycloalkanoyl and n is 0. Likewise preferred are the compounds according to formula I, wherein A is heterocyclyl and n is 1.

Another preferred aspect of the present invention are compounds of formula I, wherein n is 0 or 1.

Among the preferred compounds of formula I-A are those where $R^{12}$ and $R^{13}$ are halo and $R^{14}$ is hydrogen and $R^{17}$ is lower alkyl, particularly methyl. Another preferred embodiment of the compound of formula I-A are those compounds where $R^{12}$ is halogen, $R^{13}$ and $R^{14}$ are hydrogen and $R^{17}$ is lower alkyl, particularly methyl or ethyl. Another embodiment of the compound of formula I-A are those compounds where $R^{12}$, $R^{13}$ and $R^{14}$ are halo, while $R^{17}$ is lower alkyl, particularly methyl. Still another embodiment of the compound of formula I-A are those compounds where $R^{12}$ is hydrogen and $R^{13}$ and R14 are independently hydrogen or lower alkyl and $R^{17}$ is lower alkyl, particularly methyl. Still another embodiment of the compounds of formula I-A are those compounds where $R^{12}$ is hydrogen and $R^{13}$ and $R^{14}$ are halo or lower alkyl, while $R^{17}$ is lower alkyl, particularly methyl. While $R^{17}$ is lower alkyl, particularly methyl, a still further embodiment of the compound of formula I-A are those compounds where $R^{12}$ is hydrogen and one of $R^{13}$ and $R^{14}$ is trimethyl, trifluoromethoxy or cyano while the other is hydrogen halo or lower alkyl and $R^{17}$ is lower alkyl, particularly methyl. Another embodiment of the compound of formula I-A are those where $R^{17}$ is hydroxy lower alkyl while $R^{12}$ is hydrogen and one of $R^{13}$ and $R^{14}$ is trifluoromethyl, trifluoromethoxy or cyano while the other is hydrogen, halo or lower alkyl.

The compound of formula I-B has various preferred embodiments. Among the preferred embodiments are those compounds where $R^{22}$ and $R^{23}$ taken together with their attached carbon atoms form a carbocyclic ring, particularly the 4 to 6 membered saturated carbocyclic ring. Another embodiment of the compound of formula I-B are those compounds wherein one of $R^{22}$ and $R^{23}$ is hydrogen while the other is hydroxy, lower alkyl lower alkyl aminocarbonyl, di-lower alkyl amino carbonyl, lower alkoxy lower alkyl, lower alkylcarbonylamino or lower alkoxy lower alkoxy lower alkyl.

Preferred embodiments are where Y is a saturated 4 to 6 membered carboxylic ring or is a 5 to 7 membered heterocyclic ring containing at most two heteroaotms selected from the group consisting of oxygen or nitrogen. Generally, the compounds of formula I-C were Y is a heterocyclic ring containing either one oxygen or one nitrogen atom in the ring are generally preferred.

Preferred compounds according to formula I are those, wherein $R^7$ is hydrogen or alkyl. Particularly preferred are methyl and ethyl.

Further preferred compounds according to formula I are those, wherein $R^8$ is hydrogen or alkyl. Particularly preferred are compounds of formula I, wherein $R^8$ is methyl. Very preferred are compounds according to formula I, wherein $R^8$ is hydrogen.

Examples of preferred compounds of formula I are:

(2S,10aR)-2-(9-bromo-3,4,10,10a-tetrahydro-1H-pyrazino[1,2-a]indol-2-yl)-cyclobutanone;
(2R,10aR)-2-(9-bromo-3,4,10,10a-tetrahydro-1H-pyrazino[1,2-a]indol-2-yl)-cyclobutanone;
(2S,10aS)-2-(9-bromo-3,4,10,10a-tetrahydro-1H-pyrazino[1,2-a]indol-2-yl)-cyclobutanone;
(2R,10aS)-2-(9-bromo-3,4,10,10a-tetrahydro-1H-pyrazino[1,2-a]indol-2-yl)-cyclobutanone;
(10aR)-3-(9-bromo-3,4,10,10a-tetrahydro-1H-pyrazino[1,2-a]indol-2-ylmethyl)-oxazolidin-2-one;
(10aS)-3-(9-bromo-3,4,10,10a-tetrahydro-1H-pyrazino[1,2-a]indol-2-ylmethyl)-oxazolidin-2-one;
(10aR)-2-(9-bromo-3,4,10,10a-tetrahydro-1H-pyrazino[1,2-a]indol-2-yl)-ethanol;
(10aR)-(9-bromo-3,4,10,10a-tetrahydro-1H-pyrazino[1,2-a]indol-2-yl)-acetic acid methyl ester;
(10aR)-2-(9-bromo-3,4,10,10a-tetrahydro-1H-pyrazino[1,2-a]indol-2-yl)-acetamide;
(4R,10aR)-7-chloro-4-methyl-1,2,3,4,10,10a-hexahydro-pyrazino[1,2-a]indole;
(4R,10aS)-7-chloro-4-methyl-1,2,3,4,10,10a-hexahydro-pyrazino[1,2-a]indole;
(4S,10aS)-7-chloro-4-methyl-1,2,3,4,10,10a-hexahydro-pyrazino[1,2-a]indole;
(4S,10aR)-7-chloro-4-methyl-1,2,3,4,10,10a-hexahydro-pyrazino[1,2-a]indole.
(4R,10aR)-4-Methyl-7-trifluoromethyl-1,2,3,4,10,10a-hexahydro-pyrazino[1,2-a]indole;
(4R,10aS)-4-Methyl-7-trifluoromethyl-1,2,3,4,10,10a-hexahydro-pyrazino[1,2-a]indole;
(4R,10aS)-6-Ethyl-4-methyl-1,2,3,4,10,10a-hexahydro-pyrazino[1,2-a]indole;
(4R,10aR)-6-Ethyl-4-methyl-1,2,3,4,10,10a-hexahydro-pyrazino[1,2-a]indole;
(4R,10aR)-8-Bromo-4-methyl-7-trifluoromethyl-1,2,3,4,10,10a-hexahydro-pyrazino[1,2-a]indole;
(4R,10aR)-4,6,7-Trimethyl-1,2,3,4,10,10a-hexahydro-pyrazino[1,2-a]indole;
(4R,10aR)-7-Bromo-4-methyl-1,2,3,4,10,10a-hexahydro-pyrazino[1,2-a]indole;
(4R,10aR)-4,8-Dimethyl-7-trifluoromethyl-1,2,3,4,10,10a-hexahydro-pyrazino[1,2-a]indole;
(4R,10aR)-9-Chloro-4-methyl-1,2,3,4,10,10a-hexahydro-pyrazino[1,2-a]indole;
(4R,10aS)-4,8-Dimethyl-7-trifluoromethyl-1,2,3,4,10,10a-hexahydro-pyrazino[1,2-a]indole;
(4R,10aR)-7-Chloro-8-fluoro-4-methyl-1,2,3,4,10,10a-hexahydro-pyrazino[1,2-a]indole;
(4R,10aS)-8-Bromo-4-methyl-7-trifluoromethyl-1,2,3,4,10,10a-hexahydro-pyrazino[1,2-a]indole;
(4R,10aR)-4-Methyl-1,2,3,4,10,10a-hexahydro-pyrazino[1,2-a]indole-7-carbonitrile;
(4R,10aR)-9-Chloro-6-fluoro-4-methyl-1,2,3,4,10,10a-hexahydro-pyrazino[1,2-a]indole;
(4R,10aR)-6,7-Difluoro-4-methyl-1,2,3,4,10,10a-hexahydro-pyrazino[1,2-a]indole;
(4R,10aS)-6,7-Difluoro-4-methyl-1,2,3,4,10,10a-hexahydro-pyrazino[1,2-a]indole;
(4R,10aR)-7-Chloro-6-fluoro-4-methyl-1,2,3,4,10,10a-hexahydro-pyrazino[1,2-a]indole;
(4RS,10aRS)-7-Bromo-4-ethyl-1,2,3,4,10,10a-hexahydro-pyrazino[1,2-a]indole;
(4RS,10aSR)-7-Bromo-4-ethyl-1,2,3,4,10,10a-hexahydro-pyrazino[1,2-a]indole;
(4RS,10aRS)-6,7,8-Tribromo-4-ethyl-1,2,3,4,10,10a-hexahydro-pyrazino[1,2-a]indole;
(4RS,10aRS)-7,8-Dibromo-4-ethyl-1,2,3,4,10,10a-hexahydro-pyrazino[1,2-a]indole;
(4R,10aR)-7-Bromo-4-ethyl-1,2,3,4,10,10a-hexahydro-pyrazino[1,2-a]indole;
(4S,10aS)-7-Bromo-4-ethyl-1,2,3,4,10,10a-hexahydro-pyrazino[1,2-a]indole;
(4RS,10aSR)-4-Ethyl-1,2,3,4,10,10a-hexahydro-pyrazino[1,2-a]indole;
(4RS,10aRS)-4-Ethyl-1,2,3,4,10,10a-hexahydro-pyrazino[1,2-a]indole;
(4R,10aR)-8-Bromo-6-ethyl-4-methyl-1,2,3,4,10,10a-hexahydro-pyrazino[1,2-a]indole;
(4R,10S,10aR)-4,6,10-Trimethyl-1,2,3,4,10,10a-hexahydro-pyrazino[1,2-a]indole;
(4R,10R,10aR)-4,6,10-Trimethyl-1,2,3,4,10,10a-hexahydro-pyrazino[1,2-a]indole;
(4R,10aR)-8-Fluoro-4,7-dimethyl-1,2,3,4,10,10a-hexahydro-pyrazino[1,2-a]indole;
(4R,10aS)-8-Fluoro-4,7-dimethyl-1,2,3,4,10,10a-hexahydro-pyrazino[1,2-a]indole;
(4R,10aR)-6-Fluoro-4,7-dimethyl-1,2,3,4,10,10a-hexahydro-pyrazino[1,2-a]indole;
(4R,10aS)-6-Fluoro-4,7-dimethyl-1,2,3,4,10,10a-hexahydro-pyrazino[1,2-a]indole;
(4R,10aR)-8-Fluoro-4-methyl-1,2,3,4,10,10a-hexahydro-pyrazino[1,2-a]indole;
(4R,10aR)-4,6-Dimethyl-1,2,3,4,10,10a-hexahydro-pyrazino[1,2-a]indole;
(4R,10aS)-4,6-Dimethyl-1,2,3,4,10,10a-hexahydro-pyrazino[1,2-a]indole;
(4R,10aR)-7-Bromo-9-fluoro-4-methyl-1,2,3,4,10,10a-hexahydro-pyrazino[1,2-a]indole;
(4R,10aR)-6-Fluoro-4-methyl-1,2,3,4,10,10a-hexahydro-pyrazino[1,2-a]indole;
(4R,10aR)-6,9-Difluoro-4-methyl-1,2,3,4,10,10a-hexahydro-pyrazino[1,2-a]indole;
(4R,10aR)-7,9-Dichloro-4-methyl-1,2,3,4,10,10a-hexahydro-pyrazino[1,2-a]indole;
(4R,10aS)-7,9-Dichloro-4-methyl-1,2,3,4,10,10a-hexahydro-pyrazino[1,2-a]indole;
(4R,10aR)-4,7,9-Trimethyl-1,2,3,4,10,10a-hexahydro-pyrazino[1,2-a]indole;
(4R,10aS)-6-Bromo-4-methyl-1,2,3,4,10,10a-hexahydro-pyrazino[1,2-a]indole;
(4R,10aR)-7-Fluoro-4,6-dimethyl-1,2,3,4,10,10a-hexahydro-pyrazino[1,2-a]indole;
(4R,10aS)-7-Chloro-4,8-dimethyl-1,2,3,4,10,10a-hexahydro-pyrazino[1,2-a]indole;
(4R,10aR)-7-Chloro-4,8-dimethyl-1,2,3,4,10,10a-hexahydro-pyrazino[1,2-a]indole;
(4R,10aR)-4-Methyl-6-trifluoromethoxy-1,2,3,4,10,10a-hexahydro-pyrazino[1,2-a]indole;
(4R,10aR)-6-Fluoro-4,9-dimethyl-1,2,3,4,10,10a-hexahydro-pyrazino[1,2-a]indole;
(4R,10aS)-6-Fluoro-4,9-dimethyl-1,2,3,4,10,10a-hexahydro-pyrazino[1,2-a]indole;
(4R,10aR)-4-Methyl-1,2,3,4,10,10a-hexahydro-pyrazino[1,2-a]indole-6-carbonitrile;

(4R,10aR)-6-Chloro-4,8-dimethyl-1,2,3,4,10,10a-hexahydro-pyrazino[1,2-a]indole;
(4R,10aS)-6-Chloro-4,8-dimethyl-1,2,3,4,10,10a-hexahydro-pyrazino[1,2-a]indole;
(4R,10aR)-4,6,9-Trimethyl-1,2,3,4,10,10a-hexahydro-pyrazino[1,2-a]indole;
(4R,10aS)-4,6,7-Trimethyl-1,2,3,4,10,10a-hexahydro-pyrazino[1,2-a]indole;
(4R,10aS)-4,6,9-Trimethyl-1,2,3,4,10,10a-hexahydro-pyrazino[1,2-a]indole;
(4R,10aR)-7-Chloro-4,6-dimethyl-1,2,3,4,10,10a-hexahydro-pyrazino[1,2-a]indole;
(4R,10aS)-7-Chloro-4,6-dimethyl-1,2,3,4,10,10a-hexahydro-pyrazino[1,2-a]indole;
(4S,10aS)-7-Chloro-4-ethyl-1,2,3,4,10,10a-hexahydro-pyrazino[1,2-a]indole;
(4R,10aR)-7-Chloro-4-ethyl-1,2,3,4,10,10a-hexahydro-pyrazino[1,2-a]indole;
(4S,10aR)-7-chloro-4-ethyl-1,2,3,4,10,10a-hexahydro-pyrazino[1,2-a]indole;
(4R,10aS)-7-chloro-4-ethyl-1,2,3,4,10,10a-hexahydro-pyrazino[1,2-a]indole;
(4R,10aR)-7-Chloro-4-ethyl-1,2,3,4,10,10a-hexahydro-pyrazino[1,2-a]indole;
(4R,10aS)-7-Chloro-4-ethyl-1,2,3,4,10,10a-hexahydro-pyrazino[1,2-a]indole;
(4S,10aS)-7-Chloro-4-ethyl-1,2,3,4,10,10a-hexahydro-pyrazino[1,2-a]indole;
(4S,10aR)-7-Chloro-4-ethyl-1,2,3,4,10,10a-hexahydro-pyrazino[1,2-a]indole;
(4R,10aS)-6-Chloro-4,7-dimethyl-1,2,3,4,10,10a-hexahydro-pyrazino[1,2-a]indole;
(4R,10aR)-6-Chloro-4,7-dimethyl-1,2,3,4,10,10a-hexahydro-pyrazino[1,2-a]indole;
(10R,6aS)-10-Methyl-2,3,6,6a,7,8,9,10-octahydro-1H-8,10a-diaza-cyclopenta[c]fluorene;
(4R,10aR)-N-(4-Methyl-1,2,3,4,10,10a-hexahydro-pyrazino[1,2-a]indol-7-yl)-acetamide;
(4R,10aR)-(4-Methyl-1,2,3,4,10,10a-hexahydro-pyrazino[1,2-a]indol-7-yl)-methanol;
(4R,10aR)-4-Methyl-1,2,3,4,10,10a-hexahydro-pyrazino[1,2-a]indole-7-carboxylic acid butylamide;
(4R,10aR)-4,8-Dimethyl-1,2,3,4,10,10a-hexahydro-pyrazino[1,2-a]indole;
(4R,10aR)-8-Bromo-4,7-dimethyl-1,2,3,4,10,10a-hexahydro-pyrazino[1,2-a]indole;
(4R,10aS)-8-Bromo-4,7-dimethyl-1,2,3,4,10,10a-hexahydro-pyrazino[1,2-a]indole;
(4R,10aS)4,7-Dimethyl-1,2,3,4,10,10a-hexahydro-pyrazino[1,2-a]indole;
(4R,10aR)4,7-Dimethyl-1,2,3,4,10,10a-hexahydro-pyrazino[1,2-a]indole;
(4R,10aR)-4,7,8-Trimethyl-1,2,3,4,10,10a-hexahydro-pyrazino[1,2-a]indole;
(4R,10aS)4,7,8-Trimethyl-1,2,3,4,10,10a-hexahydro-pyrazino[1,2-a]indole;
(4R,10aR)-6,7-Dichloro-4-methyl-1,2,3,4,10,10a-hexahydro-pyrazino[1,2-a]indole;
(4R,10aS)-8-Fluoro-4,6-dimethyl-1,2,3,4,10,10a-hexahydro-pyrazino[1,2-a]indole;
(4R,10aR)-8-Bromo-7-fluoro-4methyl-1,2,3,4,10,10a-hexahydro-pyrazino[1,2-a]indole;
(4R,10aS)-8-Bromo-7-fluoro-4methyl-1,2,3,4,10,10a-hexahydro-pyrazino[1,2-a]indole;
(4R,10aR)-4-Methyl-1,2,3,4,10,10a-hexahydro-pyrazino[1,2-a]indole-7-carboxylic acid diethylamide;
(4R,10aR)-8-Fluoro-4,6-dimethyl-1,2,3,4,10,10a-hexahydro-pyrazino[1,2-a]indole;
(4R,10aR)-7-Methoxymethyl-4-methyl-1,2,3,4,10,10a-hexahydro-pyrazino[1,2-a]indole;
(4R,10aR)-7-(2-Methoxy-ethoxymethyl)-4-methyl-1,2,3,4,10,10a-hexahydro-pyrazino[1,2-a]indole;
(4R,10aR)-6-Bromo-4,7-dimethyl-1,2,3,4,10,10a-hexahydro-pyrazino[1,2-a]indole;
(4S,10aS)-(7-Trifluoromethyl-1,2,3,4,10,10a-hexahydro-pyrazino[1,2-a]indol-4-yl)-methanol; and
(4S,10aR)-(7-Trifluoromethyl-1,2,3,4,10,10a-hexahydro-pyrazino[1,2-a]indol-4-yl)-methanol.

Examples of particularly preferred compounds of formula I are:
(4R,10aR)-7-Chloro-4-methyl-1,2,3,4,10,10a-hexahydro-pyrazino[1,2-a]indole;
(4R,10aR)-4,6,7-Trimethyl-1,2,3,4,10,10a-hexahydro-pyrazino[1,2-a]indole;
(4R,10aR)-7-Bromo-4-methyl-1,2,3,4,10,10a-hexahydro-pyrazino[1,2-a]indole;
(4R,10aR)-4,8-Dimethyl-7-trifluoromethyl-1,2,3,4,10,10a-hexahydro-pyrazino[1,2-a]indole;
(4R,10aR)-7-Bromo-4-ethyl-1,2,3,4,10,10a-hexahydro-pyrazino[1,2-a]indole;
(4R,10aR)-4,6-Dimethyl-1,2,3,4,10,10a-hexahydro-pyrazino[1,2-a]indole;
(4R,10aR)-4-Methyl-1,2,3,4,10,10a-hexahydro-pyrazino[1,2-a]indole-6-carbonitrile;
(4R,10aS)-4,6,9-Trimethyl-1,2,3,4,10,10a-hexahydro-pyrazino[1,2-a]indole;
(4R,10aS)-7-Chloro-4,6-dimethyl-1,2,3,4,10,10a-hexahydro-pyrazino[1,2-a]indole; and
(4R,10aS)-6-Chloro-4,7-dimethyl-1,2,3,4,10,10a-hexahydro-pyrazino[1,2-a]indole.

Processes for the manufacture of the compounds according to formula I are an object of the present invention. The substituents and indices used in the following schemes have the significance given above unless indicated to the contrary.

Indoles of formula A can be prepared by methods known in the art, (e.g., T. L. Gilchrist, Heterocyclic chemistry, 1997 or The chemistry of heterocyclic compounds Vol 25, 1972 or Joule, J. A. Indoles, isoindoles, their reduced derivatives, and carbazoles. Rodd's Chem. Carbon Compd. 1997 or G. W. Gribble, J. Chem. Soc. Perkin I 2000, 1045)

Scheme 1

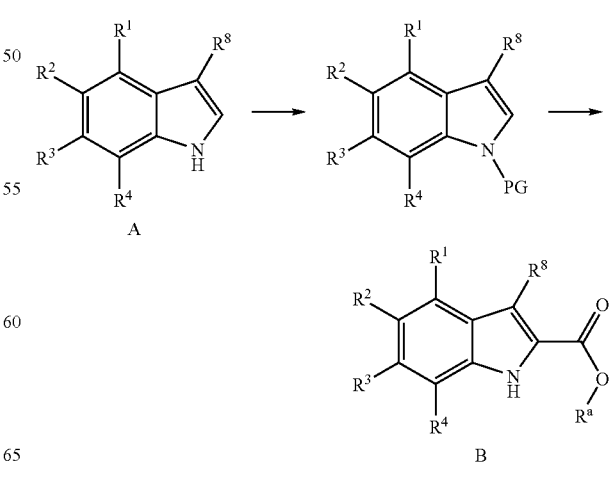

Indole-2-carboxylates of formula B can be prepared by methods known in the art (see above) or alternatively from indoles of formula A by first protecting the indole nitrogen with a suitable protecting group (PG; e.g., tert-butoxycarbonyl (Boc)), treating the protected indole derivative with a suitable base under anhydrous conditions (e.g., with lithium 2,2,6,6-tetramethylpiperidide in THF), reacting the intermediate anion with a chloroformate (e.g. ethyl chloroformate) and removing the protecting group (e.g., by treatment with acid for the Boc protecting group). $R^a$ in scheme 1 is an alkyl group, preferably methyl or ethyl.

Scheme 2:

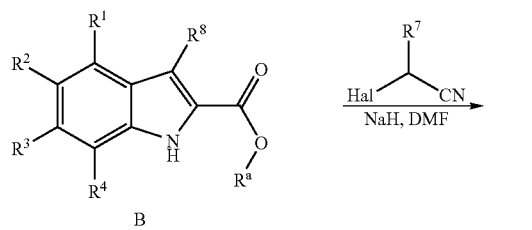

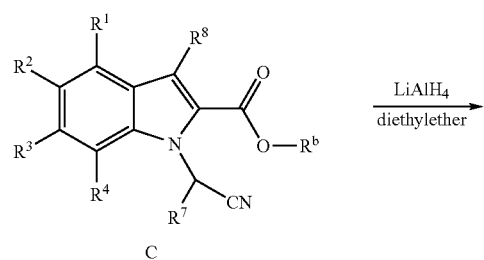

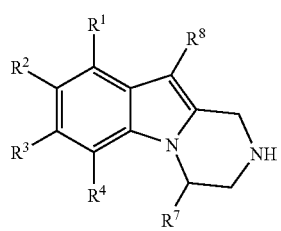

Pyrazinoindoles of formula D1 can be prepared by a process where the indole-2-carboxylate of formula B is first reacted with an alpha halo alkanenitrile (e.g., 2-bromo propionitrile) in a suitable solvent (e.g., DMF) with a suitable base (e.g., NaH). The intermediate C is reduced and cyclized to the tetrahydro-pyrazino[1,2-a]indole D1 by reaction with a suitable reducing agent in a suitable solvent (e.g., LiAlH$_4$ in THF or diethylether). In the case where $R^7 \neq H$, the latter reduction is preferably carried out stepwise, by subsequent treatment of intermediate C with (i) borane-dimethylsulfide complex in THF, (ii) potassium carbonate in methanol, (iii) borane-dimethylsulfide complex in THF. $R^b$ in scheme 2 is an alkyl group, preferably a lower alkyl group, preferably methyl or ethyl.

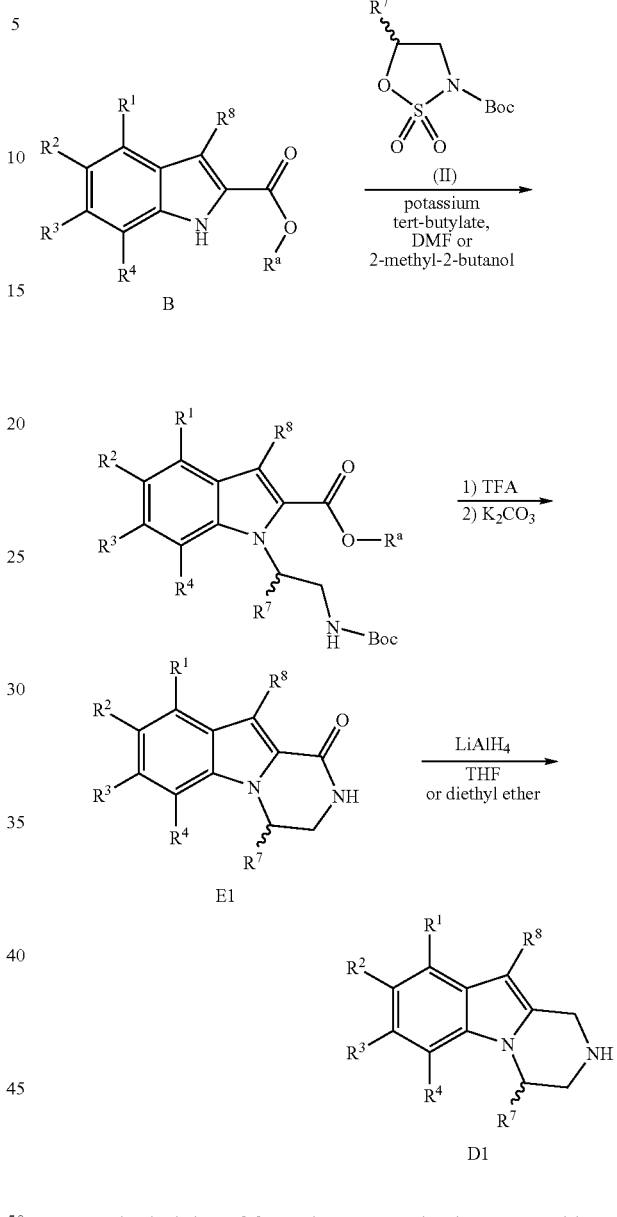

Pyrazinoindoles of formula D1 can also be prepared by a process where the indole-2-carboxylate of formula B is first reacted with the hitherto unknown Boc-sulfamidate (II) in a suitable solvent (e.g., DMF or 2-methyl-2-butanol) with a suitable base (e.g., potassium tert-butylate or sodium hydride) followed by removal of the Boc protecting group and ring closure in the presence of base (e.g., potassium carbonate). The stereochemistry of the carbon atom attached to $R^7$ in Boc-sulfamidate II is inverted (>90% e.e.) in this reaction sequence. The intermediate amide (E1) is reduced with a suitable reducing agent in a suitable solvent (e.g., LiAlH$_4$ in diethyl ether or borane-dimethylsulfide complex in THF). $R^a$ in Scheme 3 is an alkyl group, preferably a lower alkyl group, preferably methyl or ethyl.

If racemic Boc-sulfamidate II is used in this process, the enantiomers of intermediate E1 can be obtained, e. g., by preparative chiral HPLC as depicted in scheme 4.

Scheme 4:

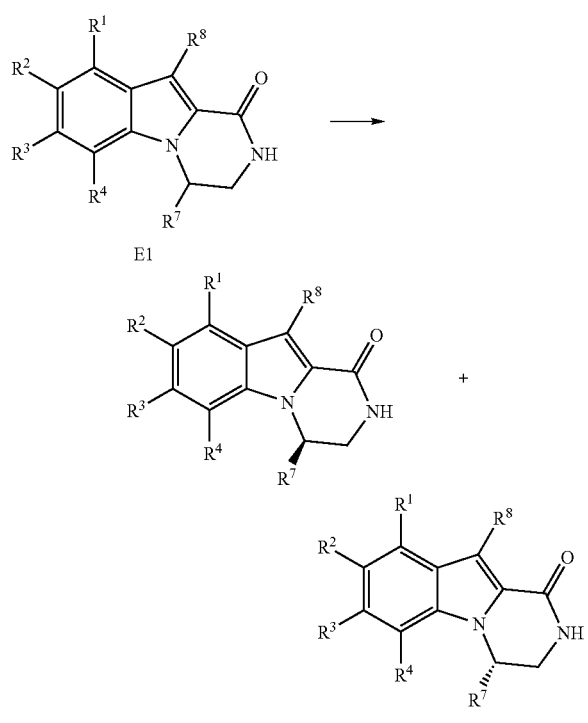

Intermediate E1 can also be prepared by a multi-step procedure starting with saponification of the ester B (e.g., with LiOH in THF/water mixtures) to the indole-2-carboxylic acid, amide coupling of the acid with a suitable aminoalcohol derivative (PG is a suitable protecting group, e.g., benzyl), transformation of the hydroxyl into a leaving group (e.g., with mesylchloride), treatment with a suitable base in a suitable solvent (e.g., NaH in DMF), and cleavage of the protective group (e. g., by hydrogenation in the presence of a palladium catalyst on carbon in the case of PG=benzyl). $R^c$ in scheme 5 is an alkyl group, preferably a lower alkyl group, preferably methyl or ethyl.

Scheme 5:

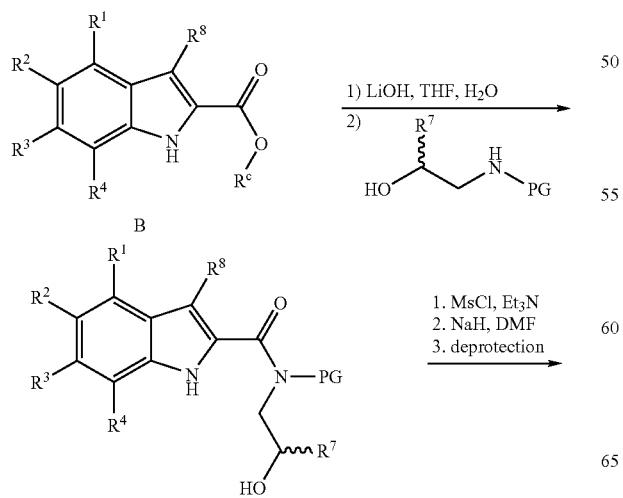

Intermediate E2 can also be prepared according to scheme 6, by a process where indole-2-carboxylate B is first reacted with an activated aminoethanol derivative (e.g. Boc-aziridine in a suitable solvent e.g. DMSO with a suitable base, e. g., KOH) followed by removal of the Boc protecting group and ring closure in the presence of base (e.g., potassium carbonate).

Scheme 6:

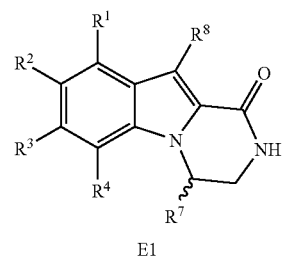

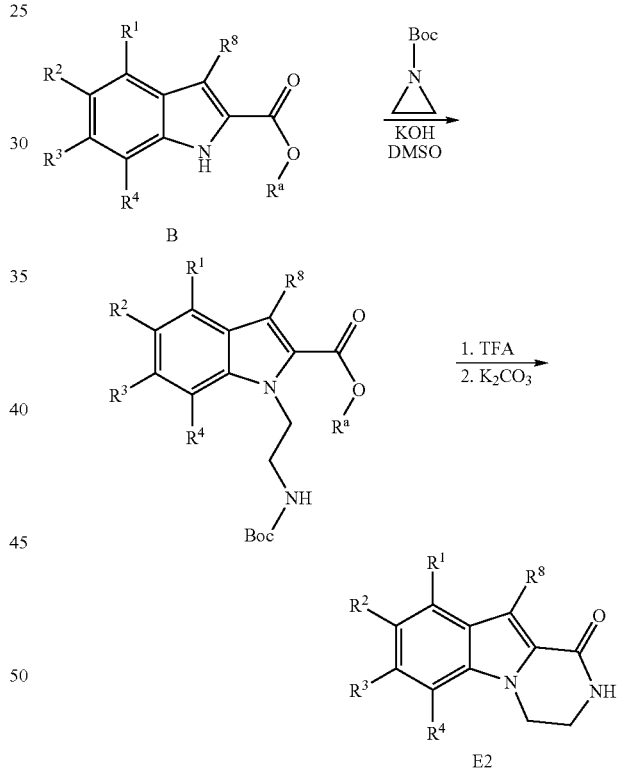

Indole derivatives F can be prepared starting from protected o-iodoanilines (a suitable protective group, $PG^1$, is, N-methoxycarbonyl) by reaction with suitably substituted and optionally protected carbinols (preferred protective groups are silyl ethers, especially preferred is tert-butyldimethylsilyl). The reaction proceeds in the presence of a suitable catalyst (e.g., bis-triphenylphosphine palladium dichloride and copper(I)iodide as co-catalyst) in a suitable solvent (e.g. triethylamine). The intermediate is treated with a base (e.g. LiOH in THF/water) to yield the indole derivative F1 (scheme 7).

Scheme 7

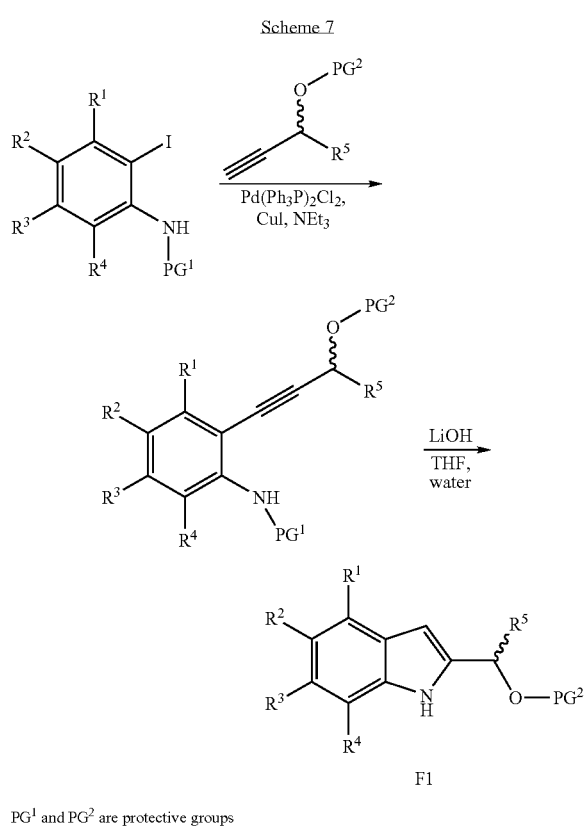

PG[1] and PG[2] are protective groups

Intermediates of formula G can be prepared according to scheme 8 by a process where the indole derivative of formula F2 is first reacted with the hitherto unknown Boc-sulfamidate (II) in a suitable solvent (e.g., DMF or 2-methyl-2-butanol) with a suitable base (e.g., NaH or potassium tert-butylate) followed by deprotection of the alcohol (e.g., with tetrabutylammoniumfluoride) in a solvent (e.g., THF) and oxidation of the alcohol (e. g., with manganese dioxide). The stereochemistry of the carbon atom attached to R[7] in Boc-sulfamidate II is inverted (>90% e.e.) in this reaction sequence.

Scheme 8

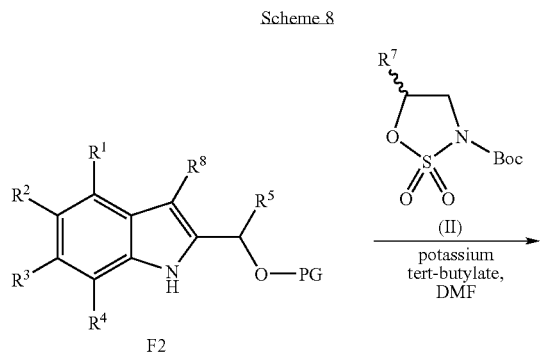

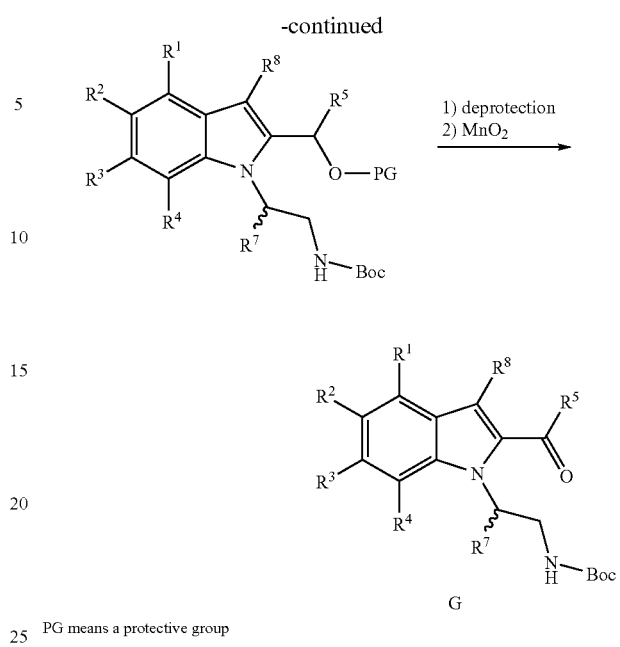

PG means a protective group

Indole derivatives G can also be prepared according to scheme 9, starting from protected o-iodoanilines (a suitable protective group, PG[1], is, N-methoxycarbonyl) by cross-coupling reaction with propargyl alcohol derivatives in the presence of a suitable catalyst (e.g., bis-triphenylphosphine palladium dichloride and copper(I)iodide as co-catalyst) in a suitable solvent (e.g. triethylamine), followed by treatment with a base (e.g. LiOH in THF/water). The alcohol intermediate is oxidised, e. g., with manganese dioxide, to yield the indole derivative H. Alkylation of H with Boc-sulfamidate (II) in a suitable solvent (e.g., DMF or 2-methyl-2-butanol) with a suitable base (e.g., potassium tert-butylate or NaH) leads to intermediate G. The stereochemistry of the carbon atom attached to R[7] in Boc-sulfamidate II is inverted (>90% e.e.) in this reaction.

Scheme 9

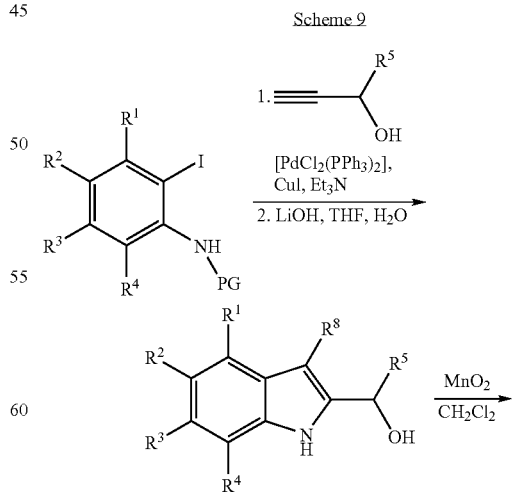

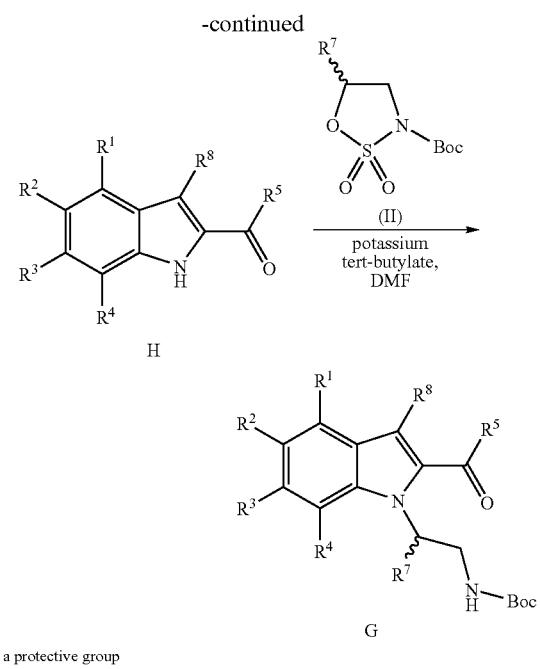

PG is a protective group

These intermediates of formula G can be further processed to compounds of formula D2 by either removal of the Boc protecting group (e. g., with trifluoroacetic acid) to yield an imine intermediate which is not isolated but reduced directly with lithium aluminium hydride to yield D2 as a separable mixture of epimers, or direct reductive amination (e.g., with sodium triacetoxyborohydride, molecular sieves and acetic acid in a suitable solvent, e.g., dichloromethane) followed deprotection of the intermediate j1 (e.g., with trifluoroacetic acid in dichloromethane) as depicted in scheme 10.

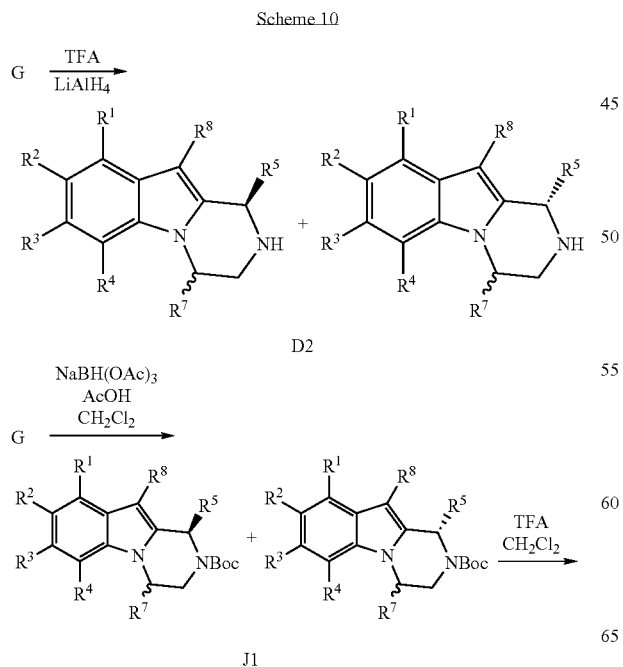

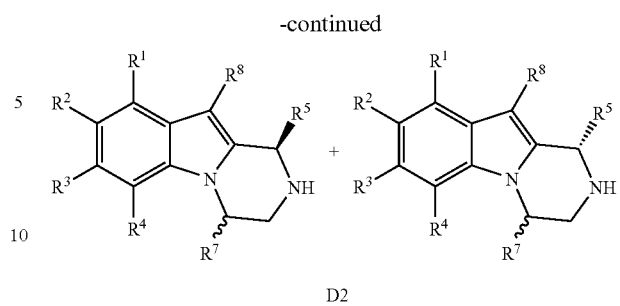

Substituents $R^8$ can be introduced as shown in scheme 11, starting from tetrahydropyrazino[1,2-a]indole D3. To that end, the amine nitrogen of D3 is protected, e. g., as the tert-butyl carbamate to generate compound J2, which is elaborated as follows:

a) Vilsmeier reaction yields aldehyde K, which is be reduced to tetrahydropyrazino[1,2-a]indole D4, preferably with triethylsilane in trifluoroacetic acid.

b) Halogenation (preferably with N-iodosuccinimide or N-bromosuccinimide in acetonitrile) yields halide L, which is transformed into compound J1 by cross-coupling reaction, using methods known in the art (e. g., F. Diederich, P. J. Stang (eds.), Metal-catalyzed Cross-coupling Reactions, Wiley-VCH, 1998)

Scheme 11

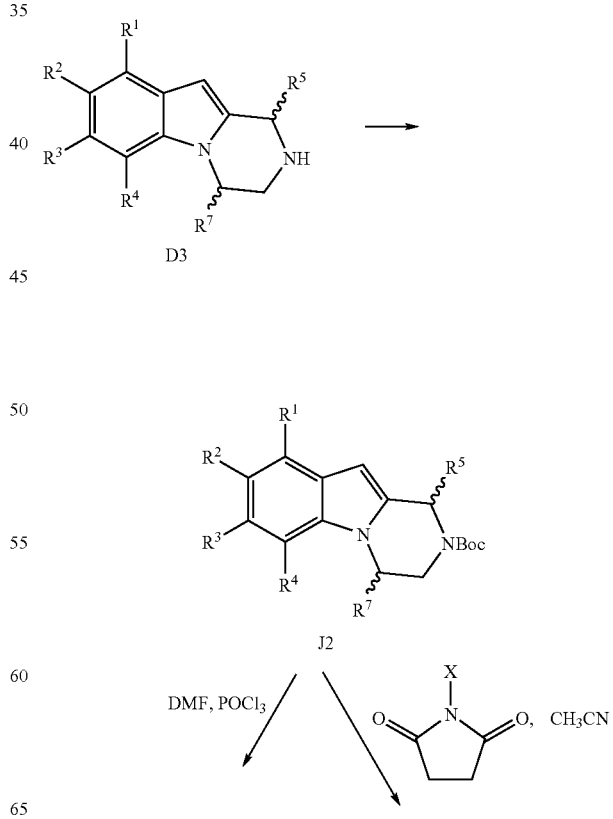

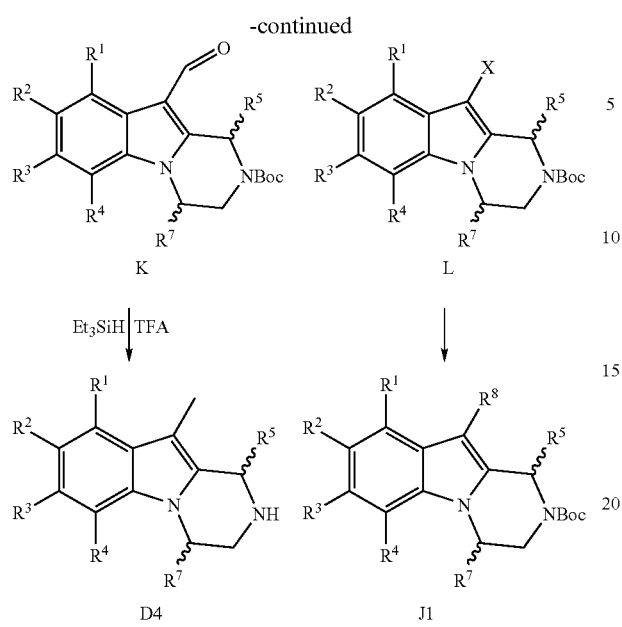

The enantiomers of tetrahydropyrazino[1,2-a]indoles D1 can be obtained either by using a chiral sulfamidate (II) or by separation of the enantiomers by preparative chiral HPLC or by crystallisation with suitable chiral acids, separation of the diastereomeric salts and isolation of the enantiomers from these salts (scheme 12). An alternative access to the enantiomers of tetrahydro-pyrazinoindoles D1 involves the separation of the enantiomers of the precursors C or G, e. g., by preparative chiral HPLC.

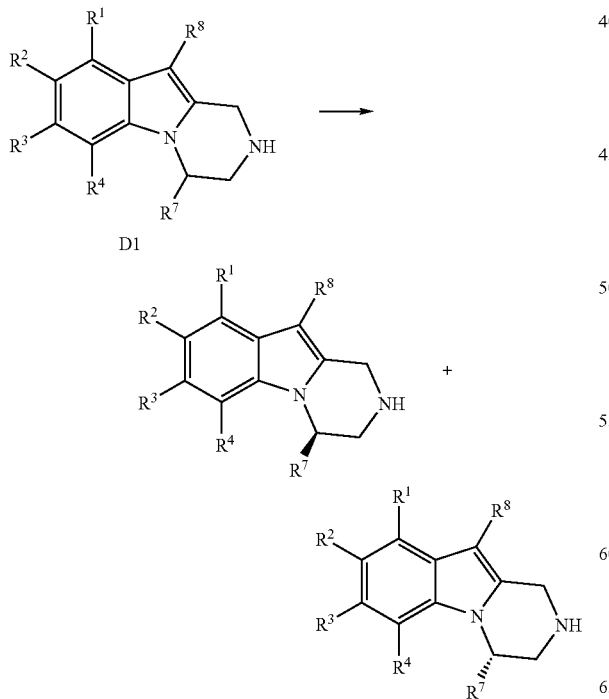

The hexahydro-pyrazino[1,2-a]indoles of formula IA can be prepared from compounds of formula D2 by reduction with suitable reducing agents (e.g. $NaBH_4$) in suitable solvents or solvent mixtures, e.eg., THF/TFA (scheme 13)

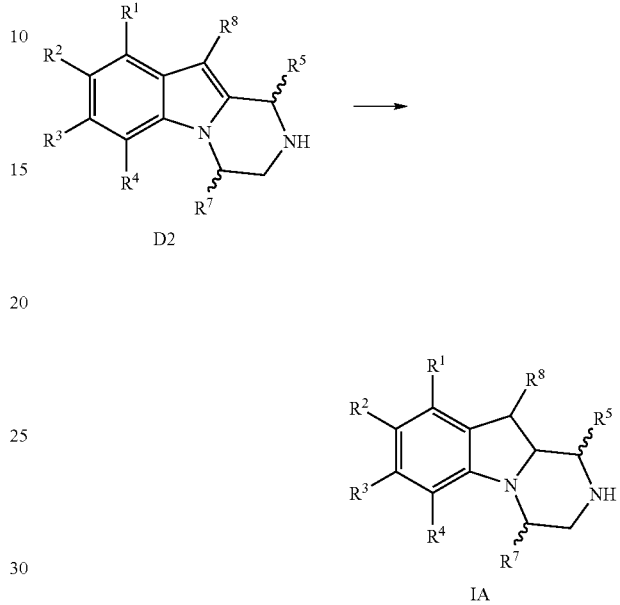

Hexahydro-pyrazino[1.2-a]indoles of formula IB can also be prepared in a two-step process from intermediate E1 where the indole moiety is reduced to produced indoline-amide M, which is then reduced under suitable conditions, e. g., $LiAlH_4$ in diethyl ether (scheme 14).

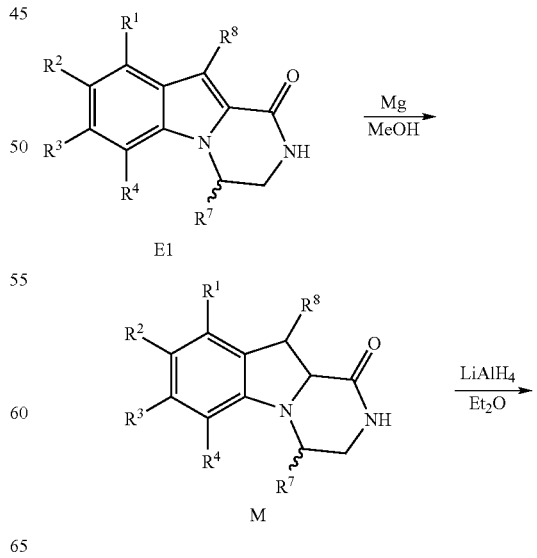

-continued

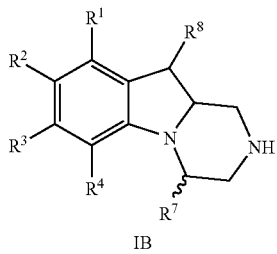

IB

Functional groups $R^1$ to $R^4$ that do not tolerate the methods described for the pyrazino-indole synthesis can be prepared from such functional groups that do by methods known in the art (e.g. March, Advanced Organic Chemistry 4$^{th}$ edition or Comprehensive Organic Functional Group Transformations, 1995). In particular, the transformations outlined in scheme 15 are carried out starting from the protected bromide N (a suitable protective group, PG, is tert-butoxycarbonyl, which is introduced by standard methods; R are one or two non-interfering substituents):

a) Cross-coupling reaction with benzophenone imine using a palladium catalyst and an auxilliary ligand, e. g., 2,2'-bis(diphenylphosphino)1,1'-binaphthyl (BINAP) and subsequent hydrogenation reaction, yields amine P, which then is acylated with acid chloride $R^{11}COCl$ ($R^{11}$=alkyl) to produce amide Q.

b) Cross-coupling reaction with copper cyanide using a palladium catalyst and an auxilliary ligand, e. g., 1,1'-Bis(diphenylphosphino)ferrocene (dppf), yields nitrile R.

c) Lithiation with n-BuLi in THF and subsequent treatment with carbon dioxide affords carboxylic acid S, which is c1) coupled with an amine $R^{12}$—NH—$R^{12}$ ($R^{12}$=H, alkyl) in the presence of a coupling agent, e. g., benzotriazol-1-yl-oxytris(dimethylamino)phosphonium hexafluorophosphate (BOP) and a base, e. g., 4-ethylmorpholine, to yield amide T, or, c2) reduced (e. g., with lithium aluminumhydride in THF) to produce alcohol U, which then is alkylated with halide $R^{13}X$ ($R^{13}$=alkyl, alkoxyalkyl, X=leaving group, e g., Br, I) to afford aryl ether V.

Scheme 15

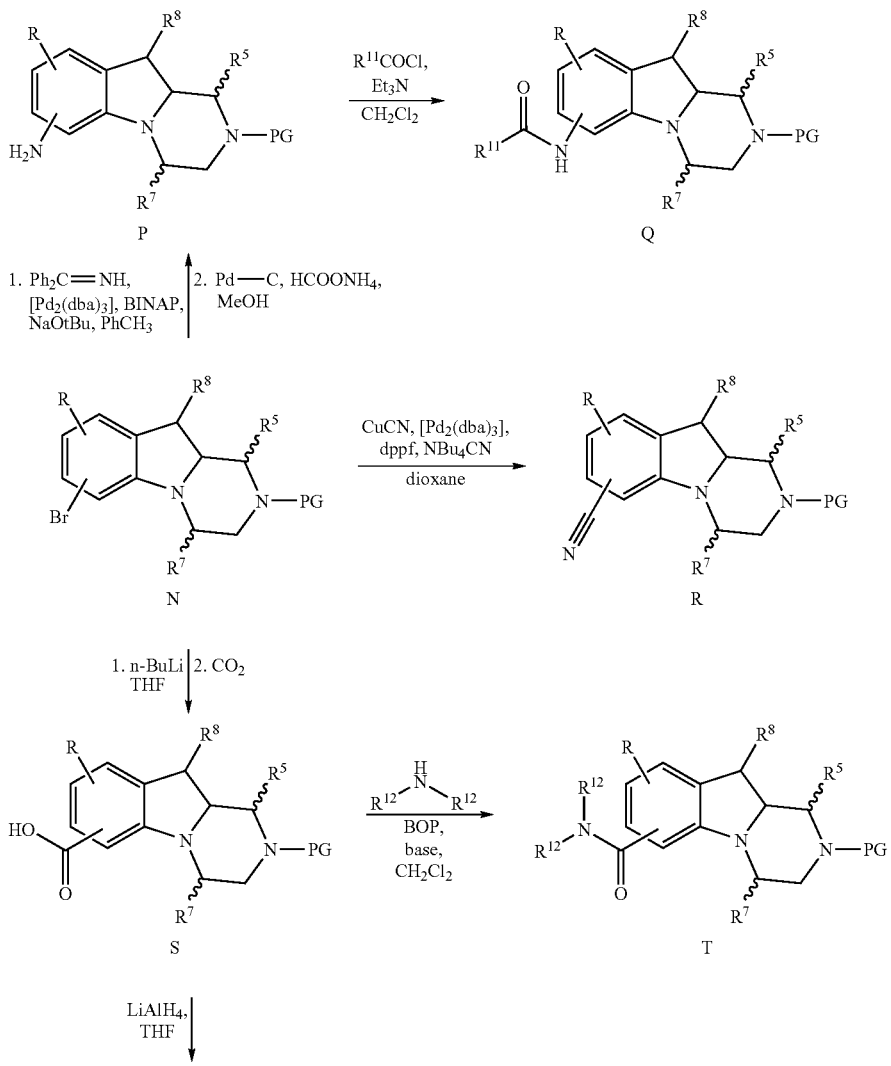

-continued

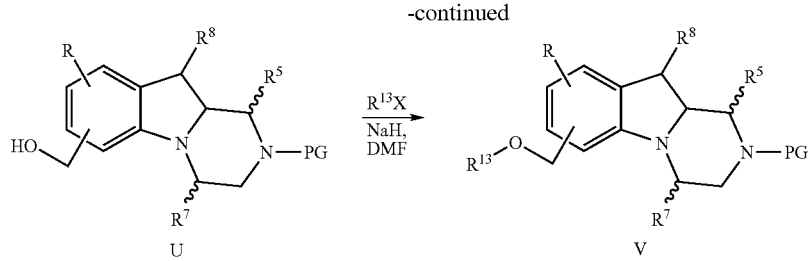

Cleavage of the protective group in compounds P, Q, R, S, T, U, or V (e. g., with acid such as trifluoroacetic acid or hydrogen chloride in a suitable solvent such as ethyl acetate in the case of PG=Boc) yields hexahydropyrazino[1,2-a]indoles IA (scheme 16).

Scheme 16

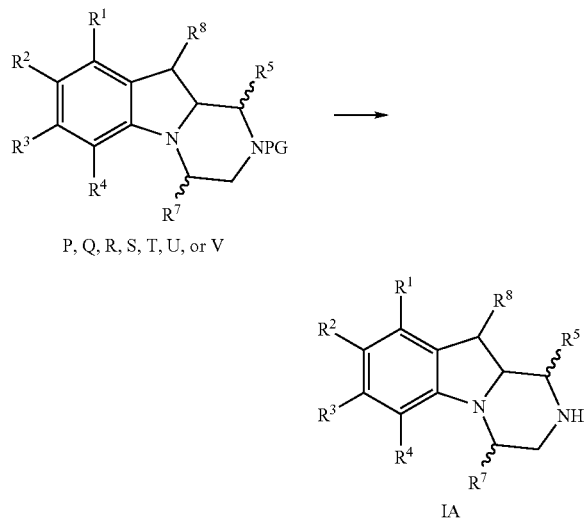

The hexahydro-pyrazino[1.2-a]indoles of formula I can be prepared from compounds of formula IA by methods known in the art (e.g. March, Advanced Organic Chemistry, 4 th. edition, page 411ff, 768ff, 898ff, 900ff, 1212ff.) e.g., alkylation reactions, Mannich reactions, acylation followed by reduction etc. (scheme 17).

Scheme 17

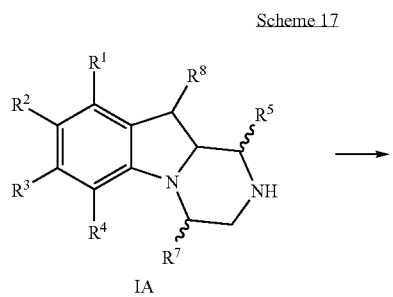

-continued

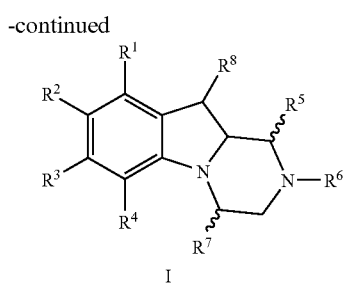

The hitherto unknown Boc-sulfamidate II can be prepared according to scheme 18, by treating a Boc-protected ethanolamine derivatives with thionylchloride in a suitable solvent e.g. THF or ethyl acetate in the presence of a suitable base, e.g. triethylamine or imidazole, and oxidising the intermediate (e.g., with sodium metaperiodate and ruthenium(IV)oxide) in a suitable solvent (e.g., ethyl acetate). The stereochemistry of the carbon atom attached to $R^7$ remains unchanged (e.e. >97%) over this sequence. In the case where $R^7$=hydroxyalkyl, the hydroxyl is protected with a suitable protective group, preferably a silyl ether, most preferably a dimethyl-(1,1,2-trimethylpropyl)-silanyoxymethyl ether. The dimethyl-(1,1,2-trimethylpropyl)-silanyloxymethyl ether is preferably deprotected during the conversion of intermediates C or E1 to tetrahydropyrazino[1,2-a]indole D1, by reaction with lithium aluminum hydride.

Scheme 18:

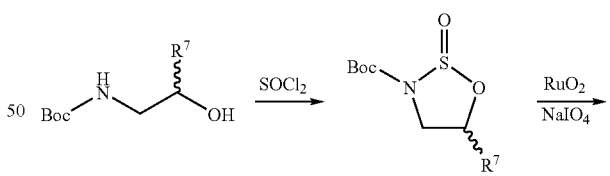

The compounds of formula (I) may be used in the treatment (including prophylactic treatment) of disorders associated with 5-$HT_2$ receptor function. The compounds may act as receptor agonists or antagonists. Preferably, the compounds may be used in the treatment (including prophylactic treatment) of disorders associated with 5-HT$_{2B}$ and/or 5-HT$_{2C}$ receptor function. Preferably, the compounds may be used in the treatment (including prophylactic treatment) of disorders where a 5-HT$_{2C}$ receptor agonist is required.

The compounds of formula (I) may be used in the treatment or prevention of central nervous disorders such as depression, atypical depression, bipolar disorders, anxiety disorders, obsessive-compulsive disorders, social phobias or panic states, sleep disorders, sexual dysfunction, psychoses, schizophrenia, migraine and other conditions associated with cephalic pain or other pain, raised intracranial pressure, epilepsy, personality disorders, age-related behavioural disorders, behavioural disorders associated with dementia, organic mental disorders, mental disorders in childhood, aggressivity, age-related memory disorders, chronic fatigue syndrome, drug and alcohol addiction, obesity, bulimia, anorexia nervosa or premenstrual tension; damage of the central nervous system such as by trauma, stroke, neurodegenerative diseases or toxic or infective CNS diseases such as encephalitis or meningitis; cardiovascular disorders such as thrombosis; gastrointestinal disorders such as dysfunction of gastrointestinal motility; diabetes insipidus; and sleep apnea.

A further aspect of the invention is a compound according to formula I for use as therapeutically active substance.

According to an other aspect of the present invention, there is provided the use of a compound of formula (I) in the manufacture of a medicament comprising a compound according to formula I for the treatment of disorders of the central nervous system, damage to the central nervous system, cardiovascular disorders, gastrointestinal disorders, diabetes insipidus, and sleep apnea.

According to a preferred aspect of this invention the disorders of the central nervous system are selected from depression, atypical depression, bipolar disorders, anxiety disorders, obsessive-compulsive disorders, social phobias or panic states, sleep disorders, sexual dysfunction, psychoses, schizophrenia, migraine and other conditions associated with cephalic pain or other pain, raised intracranial pressure, epilepsy, personality disorders, age-related behavioural disorders, behavioural disorders associated with dementia, organic mental disorders, mental disorders in childhood, aggressivity, age-related memory disorders, chronic fatigue syndrome, drug and alcohol addiction, obesity, bulimia, anorexia nervosa and premenstrual tension.

According to a preferred aspect of this invention the damage to the central nervous system is by trauma, stroke, neurodegenerative diseases or toxic or infective CNS diseases, particularly wherein the toxic or infective CNS disease is encephalitis or meningitis.

A further preferred embodiment of the present invention is the above mentioned use, wherein the cardiovascular disorder is thrombosis.

Also preferred is the mentioned use of the compounds according to formula I, wherein the gastrointestinal disorder is dysfunction of gastrointestinal motility.

Further preferred is the use of a compound of formula I in the manufacture of a medicament comprising a compound of formula I for the treatment of diabetes.

Particularly preferred is the use of a compound of formula I in the manufacture of a medicament comprising a compound of formula I for the treatment of obesity.

Further preferred is a method of treatment of any of the above mentioned disorders comprising administering to a patient in need of such treatment an effective dose of a compound of formula (I). Also preferred is the use or method as mentioned before, wherein said treatment is prophylactic treatment.

A further preferred embodiment of the present invention is a process for the preparation of a compound of formula I, wherein $R^1$ to $R^8$ are defined as before, $R^b$ is alkyl and PG means a protecting group, comprising any one of the following steps:

a) preparation of a compound according to formula D1 by reacting a compound of formula C in the presence of a reducing agent, particularly preferred in the presence of lithium aluminium hydride; or

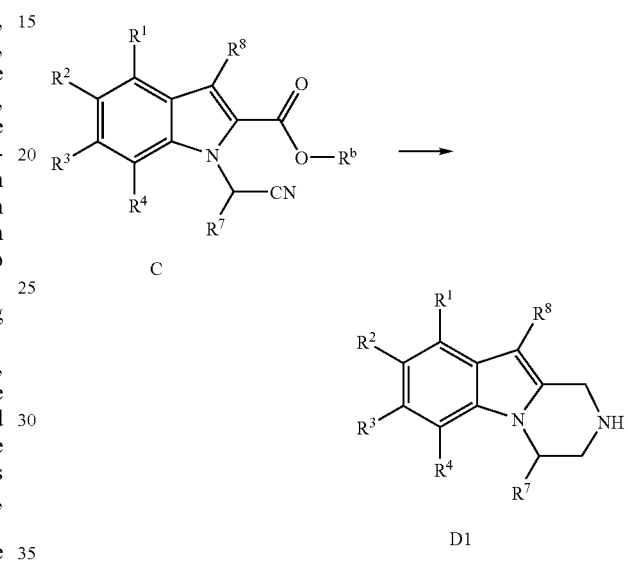

b) preparation of a compound according to formula E1 by reacting a compound according to formula D1 in the presence of a reducing agent, particularly preferred in the presence of lithium aluminium hydride or borane-dimethylsulfide-complex; or c) preparation of a compound according to formula D2 by deprotection of a compound according to formula J2.

Particularly preferred protecting groups (PG) are those, where N-PG signifies a carbamate or amide group. In a preferred embodiment deprotection can be performed as follows: a compound of formula J2, where PG is equal to Boc is deprotected with a mixture of dichloromethane and trifluoroacetic acid at room temperature; or

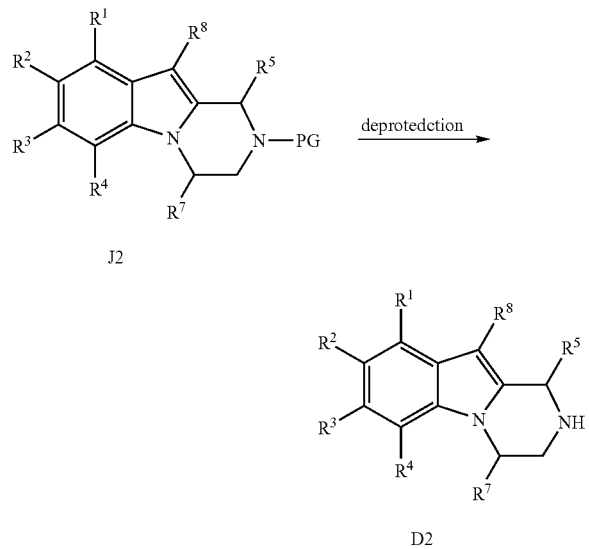

J2 d) preparation of a compound according to formula IA by reacting a compound of formula D2 in the presence of a reducing agent, particularly preferred in the presence of sodium borohydride in a mixture of tetrahydrofuran and trifluoroacetic acid; or

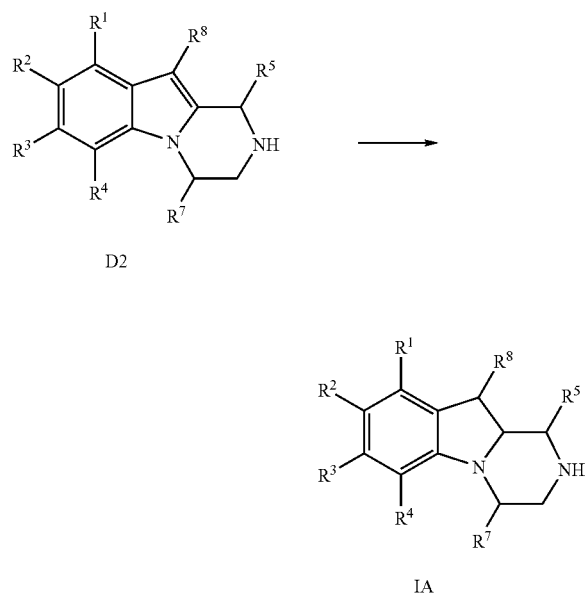

e) preparation of a compound according to formula IB by reacting a compound of formula M in the presence of a reducing agent, particularly preferred in the presence of lithium aluminum hydride; or

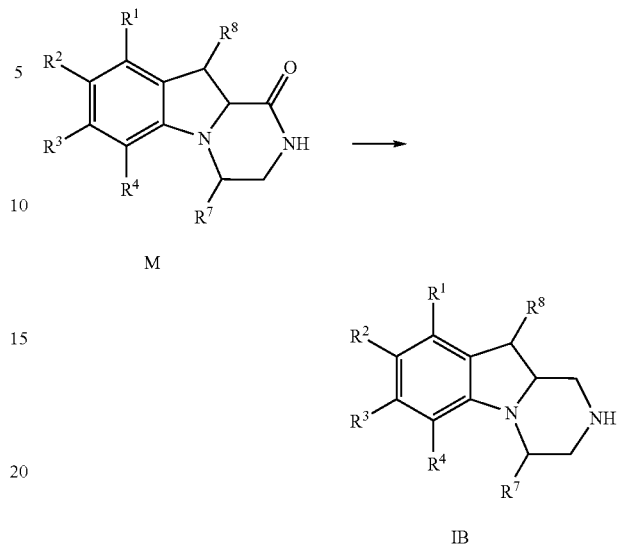

f) preparation of a compound according to formula I by reacting a compound of formula IA in the presence of an alkylation or acylation agent where acylation is followed by a reduction step.

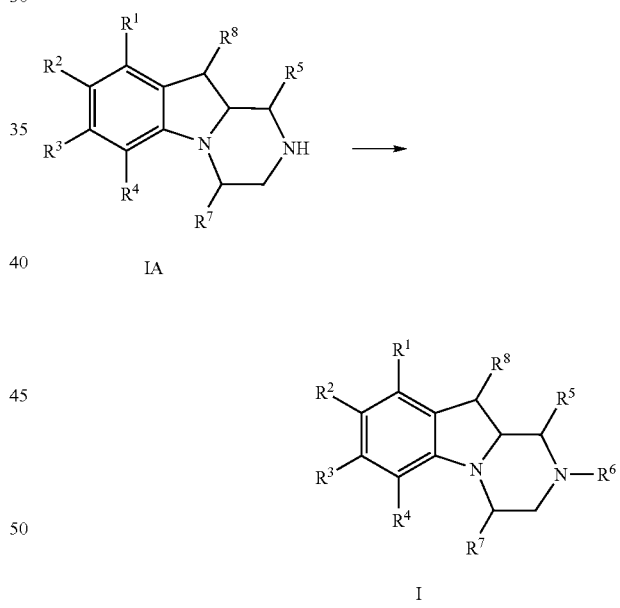

Alkylation agent means alkyl- or cycloakyl-halogenides, functionalised alkylhalogenides like hydroxylkylhalogenides, carbamoylhalogenides, alkoxycarbonylhalogenides, aryloxycarbonylalkylhalogenides or heterocyclylalkylhalogenides or the respective mesylates, tosylates or triflates instead of the halogenides. Examples of alkylation agents are 2-(bromoethoxy)-tert-butyl-dimethylsilane, methyl bromoacetate and 2-bromoacetamide. Acylation agent means the activated derivatives (e.g. acid chlorides) of alkyl- or cycloalkyl-carboxylic acids, heterocyclylcarboxylic acids or heterocyclylalkylcarboxylic acids. Examples of acylation agents are acetyl chloride and cyclopropylcarboxylic acid chloride; or g) preparation of a compound according to formula I by reacting a compound of formula B, wherein $R^a$ is alkyl in the presence of a compound of formula (II), wherein PG is a protective group preferably tert-butoycarbonyl (Boc);

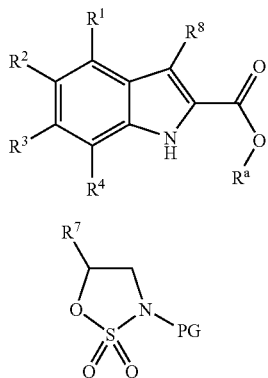

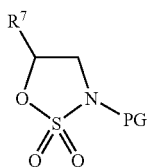

or h) preparation of a compound according to formula I by reacting a compound of formula F2 in the presence of a compound of formula (II) as defined before,

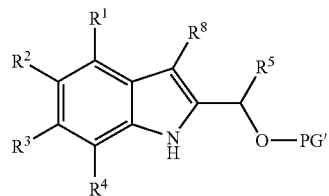

wherein PG' is hydrogen or an OH-protecting group preferably trimethylsilyl, tert-butyldimethylsilyl, acetyl, methoxymethyl or 2-tetrahydropyranyl; or i) preparation of a compound according to formula I by reacting a compound of formula H in the presence of a compound of formula (II) as defined before

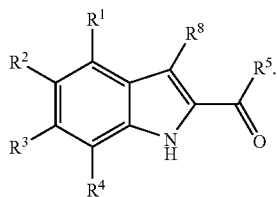

Another preferred aspect of this invention are the following intermediates:
(R)-9-Bromo-1,2,3,4,10,10a-hexahydro-pyrazino[1,2-a]indole;
(S)-9-Bromo-1,2,3,4,10,10a-hexahydro-pyrazino[1,2-a]indole;
(4R)-7-Chloro-4-methyl-1,2,3,4-tetrahydro-pyrazino[1,2a]indole and
(4S)-7-chloro-4-methyl-1,2,3,4-tetrahydro-pyrazino[1,2a]indole.

Particularly preferred intermediates are:
(S)-5-Methyl-2,2-dioxo-[1,2,3]oxathiazolidine-3-carboxylic acid tert-butyl ester
(RS)-5-Ethyl-2,2-dioxo-[1,2,3]oxathiazolidine-3-carboxylic acid tert-butyl ester
2,2-Dioxo-[1,2,3]oxathiazolidine-3-carboxylic acid tert-butyl ester
(R)-5-[Dimethyl-(1,1,2-trimethyl-propyl)-silanyloxymethyl]-2,2-dioxo-[1,2,3]oxathiazolidine-3-carboxylic acid tert-butyl ester.

According to a further aspect of the invention there is provided a pharmaceutical composition comprising a compound of formula (I) in combination with a pharmaceutically acceptable carrier or excipient and a method of making such a composition comprising combining a compound of formula (I) with a pharmaceutically acceptable carrier or excipient.

A further aspect of the present invention is the above pharmaceutical composition comprising further a therapeutically effective amount of a lipase inhibitor. Particularly preferred is the above pharmaceutical composition, wherein the lipase inhibitor is orlistat.

According to a further aspect of the invention there is provided a method of treatment of obesity in a human in need of such treatment which comprises administration to the human a therapeutically effective amount of a compound according to formula I and a therapeutically effective amount of a lipase inhibitor, particularly preferred, wherein the lipase inhibitor is orlistat. Also subject of the present invention is the mentioned method, wherein the administration is simultaneous, separate or sequential.

A further preferred embodiment of the present invention is the use of a compound of the formula I in the manufacture of a medicament for the treatment and prevention of obesity in a patient who is also receiving treatment with a lipase inhibitor, particularly preferred, wherein the lipase inhibitor is orlistat.

The processes as described above may be carried out to give a compound of the invention in the form of a free base or as an acid addition salt. If the compound of the invention is obtained as an acid addition salt, the free base can be obtained by basifying a solution of the acid addition salt. Conversely, if the product of the process is a free base, an acid addition salt, particularly a pharmaceutically acceptable acid addition salt, may be obtained by dissolving the free base in a suitable organic solvent and treating the solution with an acid, in accordance with conventional procedures for preparing acid addition salts from basic compounds.

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) transdermal or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropylmethylcellulose); fillers (e.g. lactose, microcrystalline cellulose or calcium phosphate); lubricants (e.g. magnesium stearate, talc or silica); disintegrants (e.g. potato starch or sodium starch glycollate); or wetting agents (e.g. sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before useSuch liquid preparations may be prepared by conventional .

means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

For buccal administration the composition may take the form of tablets or lozenges formulated in conventional manner.

The active compounds of the invention may be formulated for parenteral administration by injection, including using conventional catheterization techniques or infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g. sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g. dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., obesity) is 0.1 to 500 mg of the active ingredient per unit dose which could be administered, for example, 1 to 4 times per day.

The invention will now be described in detail with reference to the following examples. It will be appreciated that the invention is described by way of example only and modification of detail may be made without departing from the scope of the invention.

Assay Procedures

1. Binding to Serotonin Receptors

The binding of compounds of formula (I) to serotonin receptors was determined in vitro by standard methods. The preparations were investigated in accordance with the assays given hereinafter.

Method (a): For the binding to the 5-HT$_{2C}$ receptor the 5-HT$_{2C}$ receptors were radiolabeled with [$^3$H]-5-HT. The affinity of the compounds for 5-HT$_{2C}$ receptors in a CHO cell line was determined according to the procedure of D. Hoyer, G. Engel and H. O. Kalkman, *European J. Pharmacol.*, 1985, 118, 13–23.

Method (b): For the binding to the 5-HT$_{2B}$ receptor the 5-HT$_{2B}$ receptors were radiolabeled with [$^3$H]-5-HT. The affinity of the compounds for human 5-HT$_{2B}$ receptors in a CHO cell line was determined according to the procedure of K. Schmuck, C. Ullmer, P. Engels and H. Lubbert, *FEBS Lett.*, 1994, 342, 85–90.

Method (c): For the binding to the 5-HT$_{2A}$ receptor the 5-HT$_{2A}$ receptors were radiolabeled with [$^{125}$I]-DOI. The affinity of the compounds for 5-HT$_{2A}$ receptors in a CHO cell line was determined according to the procedure of D. J. McKenna and S. J. Peroutka, *J. Neurosci.*, 1989, 9, 3482–90.

The thus determined activity of the compound of the Example is shown in Table 1.

TABLE 1

| Compound | Method (a) Ki (2C) | Method (b) Ki (2B) | Method (c) Ki (2A) |
|---|---|---|---|
| Example 3 | 26 nM | 110 | 230 |

Preferred compounds of formula I as described above have Ki (2C) values below 10000 nM; especially preferred compounds have Ki (2C) values below 1000 nM, particularly preferred compounds have Ki (2C) values below 100 nM. Most preferred compounds have Ki (2C) values below 30 nM.

2. Functional Activity

The functional activity of compounds of formula (I) was assayed using a Fluorimetric Imaging Plate reader (FLIPR). CHO cells expressing the human 5-HT$_{2C}$ or human 5-HT$_{2A}$ receptors were counted and plated into standard 96 well microtitre plates on the day before testing to give a confluent monolayer. The cells were then dye loaded with the calcium sensitive dye, Fluo-3-AM. Unincorporated dye was removed using an automated cell washer to leave a total volume of 100 µL/well of assay buffer (Hanks balanced salt solution containing 20 mM Hepes and 2.5 mM probenecid). The drug (dissolved in 50 µL of the assay buffer) was added at a rate of 70 µL/sec to each well of the FLIPR 96 well plate during fluorescence measurements. The measurements were taken at 1 sec intervals and the maximum fluorescent signal was measured (approx 10–15 secs after drug addition) and compared with the response produced by 10 µM 5-HT (defined as 100%) to which it was expressed as a percentage response (relative efficacy). Dose response curves were constructed using Graphpad Prism (Graph Software Inc.).

TABLE 2

| | h5-HT$_{2c}$ | | h5-HT$_{2A}$ | | h5-HT$_{2B}$ | |
|---|---|---|---|---|---|---|
| Compound | EC$_{50}$ (nM) | Relative Efficacy (%) | EC$_{50}$ (nM) | Relative Efficacy (%) | EC$_{50}$ (nM) | Relative Efficacy (%) |
| Example 8 | 0.4 nM | 97% | 19 nM | 60% | 3.4 nM | 62% |

The compounds of formula (I) have activity at the h5-HT2c receptor in the range of 10,000 to 0.01 nM.

Preferred compounds of formula I as described above have activity at the h5-HT2c receptor below 10000 nM; especially preferred compounds below 1000 nM, particularly preferred compounds below 100 nM. Most preferred compounds have activity at the h5-HT2c receptor below 30 nM.

3. Efficacy

The efficacy of 5-$HT_{2c}$ agonists was assessed for ability to induce a specific syndrome.

The 5-$HT_{2c}$ syndrome is a rapid screening method to asses the in vivo efficacy of 5-$TH_{2c}$ agonists through their ability to induce three specific behaviours in rats. The animals are dosed with either a positive control (mCPP), test compound or vehicle, either s.c. or p.o. The animals are observed on an open bench, typically 30, 60 and 180 minutes and the degree of syndrome is assessed over a two minute period on a scale of 0–3 depending on the presence and severity of splayed limbs, hunched posture and retro-pulsion, the three specific behaviours which constitute the syndrome. Data is analysed using Kruskal-Wallis Analysis of Variance followed with appropriate post-hoc tests. All statistical analysis are conducted using Excel version 7-0 (Microsoft Corp.) and Statistica version 5.0 (Stasoft, Inc.).

The thus determined activity of the Example indicated that after a dose of 1 mg/kg s.c. the compound maintains a significant pharmacological efficacy for at least 180 minutes.

4. Regulation of Feeding Behaviour

The in vivo activity of compounds of formula (1) was assayed for ability to regulate feeding behaviour by assaying food consumption in food deprived animals as follows.

Test compounds are assessed following acute administration. Each study utilises a between-subjects design (typically n=8) and compares the effects of doses of the test agent to those of vehicle and a positive control.

The anorectic drug d-fenfluramine normally serves as a positive control. The route of drug administration, drug volume and injection-test-interval are dependent upon the compounds used. A palatable wet mash, made by adding powdered lab chow and water in a ration of 1:2 and mixing to a smooth consistency, is presented in 120 mL glass jars for 60 minutes each day. Intake is measured by weighing before and after each session. Care is taken to collect all spillage. Animals are allowed to habituate to the wet mash meal for 10 days. After drug administration, animals are allowed to consume the wet mash. Food consumption is assayed at pre-determined time points (typically, 1, 2 and 4 hours after administration). Food intake data are subjected to one-way analysis of variance (ANOVA) with drug as a between-subjects factor. A significant main effect is followed up by the performance of Dunnett's test in order to asses which treatment mean(s) are significantly different from the control mean. All statistical analyses were performed using Statistica Software, Version 5.0 (Statsofr Inc.) and Microsoft Excel 7.0 (Microsoft Corp.).

The thus determined activity of the Example indicated that the compounds maintain significant hypophagia 3 hours after a dose of 1 mg/kg s.c.

EXAMPLES

Example 1

Mixture of (2S,10aR) and (2R,10aR)-2-(9-bromo-3,4,10,10a-tetrahydro-1H-pyrazino[1,2-a]indol-2-yl)-cyclobutanone (10aR)-9-Bromo-1,2,3,4,10,10a-hexahydro-pyrazino[1,2-a]indole (0.10 g, 0.39 mmol) was suspended in methanol (1.5 mL). A solution of [1-cyclobutene-1,2-diylbis(oxy)]bis[trimethyl-silane, (0.10 g, 0.43 mmol) in methanol (0.5 mL) was added, the mixture was stirred for 1 d and the solvent was evaporated. Chromatography on silica gel (dichloromethane/methanol 99:1) yielded the desired product (78 mg, 61%), MS: m/e=321.3 ($M^+$).

Example 2

Mixture of (2S,10aS) and (2R,10aS)-2-(9-bromo-3,4,10,10a-tetrahydro-1H-pyrazino[1,2-a]indol-2-yl)-cyclobutanone The title compound, MS: m/e=321.2 ($M^+$), was prepared in accordance with the general method of example 1 from (10aS)-9-bromo-1,2,3,4,10,10a-hexahydro-pyrazino[1,2-a]indole and [1-cyclobutene-1,2-diylbis(oxy)]bis[trimethyl-silane.

Example 3

(10aR)-3-(9-Bromo-3,4,10,10a-tetrahydro-1H-pyrazino[1,2-a]indol-2-ylmethyl)-oxazolidin-2-one (10aR)-9-Bromo-1,2,3,4,10,10a-hexahydro-pyrazino[1,2-a]indole (0.10 g, 0.39 mmol) and 2-oxazolidinone (34 mg, 0.43 mmol) were dissolved in dichloromethane (5 mL). Formaldehyde (32 μL of a 36.5% solution in water) was added and the solution was stirred for 3 h at room temperature. The solvent was removed after drying with $MgSO_4$. Chromatography on silica gel (dichloromethane/ethylacetate 3:1) yielded the desired product (114 mg, 82%), MS: m/e=352.3 ($M+H^+$).

Example 4

(10aS)-3-(9-Bromo-3,4,10,10a-tetrahydro-1H-pyrazino[1,2-a]indol-2-ylmethyl)-oxazolidin-2-one The title compound, MS: m/e=352.3 ($M+H^+$) was prepared in accordance with the general method of example 3 from (10aS)-9-bromo-1,2,3,4,10,10a-hexahydro-pyrazino[1,2-a]indole and 2-oxazolidinone.

Example 5

(10aR)-2-(9-Bromo-3,4,10,10a-tetrahydro-1H-pyrazino[1,2-a]indol-2-yl)-ethanol (10aR)-9-Bromo-1,2,3,4,10,10a-hexahydro-pyrazino[1,2-a]indole (0.10 g, 0.39 mmol) and 2-(bromoethoxy)-tert-butyl-dimethylsilane (88 mg, 0.39 mmol) were dissolved in acetonitrile (2 mL). Potassium carbonate (63 mg, 0.46 mmol) was added and the solution was boiled with stirring for 2 d. The solvent was removed and the residue was partitioned between dichloromethane and brine. The organic phases were pooled, dried with $MgSO_4$ and the solvent was evaporated. Chromatography on silica gel (dichloromethane/methanol 98:2) yielded the intermediate silyl-protected alcohol (124 mg, 76%), MS: m/e=413.3 (M+H$^+$).

The intermediate was dissolved in a mixture of ethanol (3 mL) and hydrochloric acid (conc. 0.1 mL) and stirred for 20 h at room temperature. Removal of the solvent was followed by partitioning between ethylacetate and saturated sodium bicarbonate. Organic phases were pooled, dried with MgSO$_4$ and the solvent was evaporated. Chromatography on silica gel (ethylacetate) yielded the desired product (50 mg, 58%), MS: m/e=297.2 (M+H$^+$).

Example 6

(10aR)-(9-Bromo-3,4,10,10a-tetrahydro-1H-pyrazino[1,2-a]indol-2-yl)-acetic acid methyl ester (10aR)-9-Bromo-1,2,3,4,10,10a-hexahydro-pyrazino[1,2-a]indole (0.07 g, 0.27 mmol) and methyl bromoacetate (43 mg, 0.27 mmol) were dissolved in acetonitrile (2 mL). Potassium carbonate (44 mg, 0.32 mmol) was added and the solution was boiled with stirring for 15 h. The solvent was removed and the residue was partitioned between dichloromethane and brine. Organic phases were pooled, dried with MgSO$_4$ and the solvent was evaporated. Chromatography on silica gel (dichloromethane/methanol 98:2) gave (10aR)-(9-bromo-3,4,10,10a-tetrahydro-1H-pyrazino[1,2-a]indol-2-yl)-acetic acid methyl ester (57 mg, 63%), MS: m/e=325.2 (M+H$^+$).

Example 7

(10aR)-2-(9-Bromo-3,4,10,10a-tetrahydro-1H-pyrazino[1,2-a]indol-2-yl)-acetamide

The title compound, MS: m/e=310.1 (M+H$^+$) was prepared in accordance with the general method of example 6 from (10aR)-9-bromo-1,2,3,4,10,10a-hexahydro-pyrazino[1,2-a]indole and 2-bromoacetamide.

Example 8

(4R,10aR)-7-Chloro-4-methyl-1,2,3,4,10,10a-hexahydro-pyrazino[1,2-a]indole

Compound 8 can be prepared as described in Example 9. MS: m/e=222.1(M$^+$), $\alpha_D^{20}$=−73.2

Example 9

(4R,10aS)-7-Chloro-4-methyl-1,2,3,4,10,10a-hexahydro-pyrazino[1,2-a]indole (4R)-7-Chloro-4-methyl-1,2,3,4-tetrahydro-pyrazino[1,2-a]indole (0.180 g; 0.816 mmol) is dissolved in a tetrahydrofuran/trifluoroacetic acid mixture (1:2; 7.5 ml) and cooled to 0° C. Sodium borohydride (62 mg; 1.63 mmol) was added and the solution was stirred for 2 h. The reaction mixture was poured in an aqueous NaOH solution, basified to ph 14 and extracted twice with ethyl-acetate. Organic phases were pooled, dried with MgSO$_4$ and the solvent was evaporated. Chromatography on silica gel (dichloromethane/methanol 9:1) gave (4R,10aR)-7-chloro-4-methyl-1,2,3,4,10,10a-hexahydro-pyrazino[1,2-a]indole (81 mg, 45%) and (4R,10aS)-7-chloro-4-methyl-1,2,3,4,10,10a-hexahydro-pyrazino[1,2-a]indole (17 mg, 9%).

Example 10

(4S,10aS)-7-Chloro-4-methyl-1,2,3,4,10,10a-hexahydro-pyrazino[1,2-a]indole

Example 10 can be prepared as described in Example 11. MS: m/e=222.1(M+), $\alpha_D^{20}$=+73.4

Example 11

(4S,10aR)-7-Chloro-4-methyl-1,2,3,4,10,10a-hexahydro-pyrazino[1,2-a]indole (4S)-7-Chloro-4-methyl-1,2,3,4-tetrahydro-pyrazino[1,2-a]indole (0.152 g; 0.689 mmol) is dissolved in a tetrahydrofuran/trifluoroacetic acid mixture (1:2; 7.5 ml) and cooled to 0° C. Sodium borohydride (52 mg; 1.38 mmol) is added and the solution was stirred for 2 h. The reaction mixture was poured in an aqueous NaOH solution (pH was put to 14) and extracted twice with ethyl-acetate. Organic phases were pooled, dried with MgSO$_4$ and the solvent was evaporated. Chromatography on silica gel (dichloromethane/methanol 9:1) gave (4S,10aS)-7-Chloro-4-methyl-1,2,3,4,10,10a-hexahydro-pyrazino[1,2-a]indole (113 mg, 74%) and (4S,10aR)-7-Chloro-4-methyl-1,2,3,4,10, 10a-hexahydro-pyrazino[1,2-a]indole (12 mg, 8%).

Intermediates (10aR)-9-Bromo-1,2,3,4,10,10a-hexahydro-pyrazino[1,2-a]indole and (10aS)-9-bromo-1,2,3,4,10,10a-hexahydro-pyrazino[1,2-a]indole Sodiumhydride (4.0 g, 92 mmol) was suspended in dimethylformamide (20 mL) and a solution of 4-bromo-1H-Indole-2-carboxylic acid ethyl ester (16.4 g, 61 mmol) in dimethylformamide (70 mL) was added. The mixture was stirred for 1 h at room temperature and after cooling to 0° C. chloroacetonitrile (7.7 mL, 122 mmol) was added. After 1 h at room temperature the mixture was added to an ice/water mixture (800 mL) and extracted with ethylacetate. The organic phases were pooled washed with brine, dried with MgSO$_4$ and the solvent was removed in vacuo. Chromatography on silica gel (ethyl acetate/n-hexane 4:1) yielded 4-bromo-1-cyanomethyl-1H-indole-2-carboxylic acid ethyl ester (13.4 g, 71%) as a colorless solid, MS: m/e=306.0 (M$^+$).

Lithium aluminiumhydride (4.0 g, 106 mmol) was suspended in diethylether (600 mL) and 4-bromo-1-cyanomethyl-1H-indole-2-carboxylic acid ethyl ester (13.0 g, 42 mmol) was added in portions. The mixture was boiled for 15 h, cooled to room temperature and added to saturated potassium sodium tartrate solution. Thorough washing of the filter-cake with ethyl acetate followed the filtration over Celite® to remove solids. The phases of the filtrate were separated and the water phase was extracted with ethylacetate. The organic phases were pooled, washed with brine, dried with MgSO$_4$ and the solvent was evaporated. Chromatography on silica gel (dichloromethane/methanol 95:5) yielded 9-bromo-1,2,3,4-tetrahydro-pyrazino[1,2-a]indole (3.6 g, 34 %) as a colorless solid, MS: m/e=250.0 (M$^+$).

9-Bromo-1,2,3,4-tetrahydro-pyrazino[1,2-a]indole (3.5 g, 13.9 mmol) was dissolved in THF (15 mL) and trifluoroacetic acid (30 mL) and cooled to 0° C. Sodium borohydride (1 g, 27.9 mmol) was added in portions, the mixture was stirred for 90 min at room temperature and added to an ice/water mixture (150 mL). After addition of sodium hydroxide solution (28%, 35 mL) to render the mixture basic it was extracted with dichloromethane. Organic phases were pooled, washed with brine, dried with MgSO₄ and the solvent was evaporated. Chromatography on silica gel (dichloromethane/methanol/ammonia 180:10:1) yielded 9-bromo-1,2,3,4,10,10a-hexahydro-pyrazino[1,2-a]indole (2.4 g, 68%) as a yellowish solid, MS: m/e=252.0 (M⁺).

9-Bromo-1,2,3,4,10,10a-hexahydro-pyrazino[1,2-a]indole (4.8 g, 18.8 mmol) was dissolved in ethanol (42 mL) and separated into the enantiomers by chromatography on a preparative Chiralpak AD® column with heptane/ethanol (95:5) as eluent. This yielded after evaporation of the solvent (10aS)-9-bromo-1,2,3,4,10,10a-hexahydro-pyrazino[1,2-a]indole (2.3 g, 48%) $\alpha_D^{20}$=−56.5 and (10aR)-9-bromo-1,2,3,4,10,10a-hexahydro-pyrazino[1,2-a]indole (2.2 g, 46%) $\alpha_D^{20}$=+49.0.

Intermediates (4R)-7-Chloro-4-methyl-1,2,3,4-tetrahydro-pyrazino[1,2a]-indole and (4S)-7-chloro-4-methyl-1,2,3,4-tetrahydro-pyrazino[1,2a]-indole Sodiumhydride (0.89 g, 20.1 mmol) was suspended in dimethylformamide (15 mL) and a solution of 6-chloro-1H-indole-2-carboxylic acid ethyl ester (2.00 g, 8.9 mmol) in dimethylformamide (8 mL) was added at 0° C. The mixture was stirred for 1 h at 0° C. then 2-bromo-propionitrile (3.6 g, 23.95 mmol) was added. After 1 h at room temperature the mixture was heated at 75° C. for 18 hours. The reaction mixture was then added to an ice/water mixture (100 mL) and extracted with ethylacetate. The organic phases were pooled washed with brine, dried with Na₂SO₄ and the solvent was removed in vacuo. Chromatography on silica gel (ether/n-hexane 1:4) yielded 6-chloro-1-(cyano-methyl-methyl)-1H-indole-2-carboxylic acid ethyl ester (2.06 g, 67%) as a colorless solid, MS: m/e=277.2 (M+H⁺).

6-Chloro-1-(cyano-methyl-methyl)-1H-indole-2-carboxylic acid ester ethyl (2.05 g; 7.4 mmol) was dissolved in tetrahydrofuran (25 mL). At 35° C. borane-dimethylsulfide complex (2M in THF; 11.1 ml; 22.2 mmol) was added and the mixture was heated to reflux for 25 minutes, cooled to 0° C. and hydrochloric acid solution (25%; 3.5 ml; 27.7 mmol) was added carefully (strong hydrogen evolution). The mixture was heated at reflux for 30 minutes then cooled to room temperature. The reaction mixture was then added to a chilled aqueous potassium carbonate solution (100 mL). The organic phases were extracted with ethylacetate.

The phases were separated and the water phase was extracted with ethylacetate. Organic phases were pooled, washed with brine, dried with Na₂SO₄ and the solvent was evaporated.

The crude residue was dissolved in dry methanol (50 ml), potassium carbonate (2.05 g; 14.8 mmol) was added and the reaction mixture was stirred at RT over night. The reaction mixture was then added to an ice/water mixture (100 mL) and extracted with ethylacetate. The organic phases were pooled washed with brine, dried with Na₂SO₄ and the solvent was removed in vacuo. Chromatography on silica gel (dichloromethane/methanol 95:5) yielded 7-chloro-4-methyl-3,4-dihydro-2H-pyrazino[1,2a]-indole-1-one (1.21 g, 69%) as an off-white foam, MS: m/e=234.1 (M⁺).

7-Chloro-4-methyl-3,4-dihydro-2H-pyrazino[1,2a]-indole-1-one (1.02 g, 4.34 mmol) was dissolved in THF (30 mL). Borane-dimethylsulfide complex (2M in THF; 20 ml; 40 mmol) was added and the mixture was heated to reflux for 3 hours. Then the reaction mixture was cooled to 0° C. and an aqueous hydrochloric acid solution (25%; 1.2 ml; 9.6 mmol) was added carefully (strong hydrogen evolution) The mixture was heated at reflux for 30 minutes, cooled to room temperature then added to a chilled aqueous potassium carbonate solution (100 mL). The organic phases were extracted with ethylacetate.

The phases were separated and the water phase was extracted with ethylacetate. Organic phases were pooled, washed with brine, dried with Na₂SO₄ and the solvent was evaporated. Chromatography on silica gel (dichloromethane/methanol 95:5) yielded 7-chloro-4-methyl-1,2,3,4-tetrahydro-pyrazino[1,2a]-indole (0.626 g, 65%) a yellow gum, MS: m/e=220.1 (M⁺).

7-chloro-4-methyl-1,2,3,4-tetrahydro-pyrazino[1,2a]-indole (548 mg, 2.48 mmol) was dissolved in ethanol (20 mL) and separated into the enantiomers by chromatography on a preparative Chiralpak AD® column with heptane/ethanol (9:1) as eluent. This yielded after evaporation of the solvent (4R)-7-chloro-4-methyl-1,2,3,4-tetrahydro-pyrazino[1,2a]-indole (183 mg, 33%) and (4S)-7-chloro-4-methyl-1,2,3,4-tetrahydro-pyrazino[1,2a]-indole (155 mg, 28%).

Example 12

(4R,10aR)-4-Methyl-7-trifluoromethyl-1,2,3,4,10,10a-hexahydro-pyrazino[1,2-a]indole hydrochloride a) (S)-5-Methyl-2,2-dioxo-[1,2,3]oxathiazolidine-3-carboxylic acid tert-butyl ester To a solution of 11.15 g (S)-carbamic acid, (2-hydroxypropyl)-, 1,1-dimethylethyl ester, in 100 mL tetrahydrofuran was added at −78° C. 80 mL of a 1.6 M solution of n-butyllithium in n-hexane during 15 min. The resulting mixture was warmed to −15° C. and stirred for 45 min. A solution of 7.5 g thionyl chloride in 50 mL tetrahydrofuran was added during 5 min. The mixture was then warmed to −15° C. and stirred for 90 min. The reaction mixture was partitioned between ethyl acetate and 10% citric acid. The phases were separated and the organic phase was washed with sodium bicarbonate and brine, dried over magnesium sulfate, evaporated and purified by chromatography on silica gel with 3:1 hexane:ethyl acetate. The intermediate sulfamidite was taken up in 60 mL ethyl acetate and 100 mL of a 10% solution of sodium metaperiodate was added. The mixture was cooled to 0° C. and 0.21 g ruthenium dioxide dihydrate was added and the mixture was stirred at this temperature for 45 min. The phases were separated and the organic phase was purified by chromatography on silica gel with 2:1 hexane:ethyl acetate to yield 5.3 g of the title compound as white crystals after recrystallization from ethanol (m.p.:111.6-115° C.) $\alpha_D^{20}$=+37.1.

b) (R)-1-(2-tert-Butoxycarbonylamino-1-methyl-ethyl)-6-trifluoromethyl-1H-indole-2-carboxylic acid ethyl ester Sodium hydride (0.75 g, 17 mmol) was suspended in N,N-dimethylformamide (15 mL) and a solution of 6-trifluoromethyl-1H-indole-2-carboxylic acid ethyl ester (3.6 g, 14 mmol) in N,N-dimethylformamide (15 mL) was added with cooling at 5° C. After 1 h (S)-5-methyl-2,2-dioxo-[1,2,3]oxathiazolidine-3-carboxylic acid tert-butyl ester (4.0 g, 17 mmol) was added and the solution was allowed to reach room temperature over the weekend. The solution was partitioned between ice water (600 mL) and diethylether (2-×250 mL). The organic layer was washed with ice water and brine, dried (MgSO₄), and evaporated. Chromatography on silica gel with n-hexane/diethylether (4:1) yielded the title product as yellow oil (5.1 g, 88%). ISP-MS: m/e=415.3 (M+H+), $\alpha_D^{20}$=–29.6 c) (R)-4-Methyl-7-trifluoromethyl-3,4-dihydro-2H-pyrazino[1,2-a]indol-1-one (R)-1-(2-tert-Butoxycarbonylamino-1-methyl-ethyl)-6-trifluoromethyl-1H-indole-2-carboxylic acid ethyl ester (4.9 g, 12 mmol) was dissolved in dichloromethane (40 mL) and treated with trifluoroacetic acid (18.3 mL) at 0° C. After removal of the ice bath, the solution was stirred for 30 min, and evaporated under reduced pressure. The residue was dissolved in methanol (40 mL), then after addition of saturated sodium bicarbonate solution (90 mL) the mixture was stirred for 20 h at room temperature. Water (100 mL) was added and the mixture was extracted with dichloromethane (2×100 mL). The organic layer was separated, washed with brine, dried (MgSO4), and evaporated. Chromatography on silica gel with hexane/ethyl acetate (1:1) yielded the title compound as a white solid (2.9 g, 90%). M.p.: 201–204° C., EI-MS: m/e=268.2 (M+), $\alpha_D^{20}$=+7.5 d) (R)-4-Methyl-7-trifluoromethyl-1,2,3,4-tetrahydro-pyrazino[1,2-a]indole (R)-4-Methyl-7-trifluoromethyl-3,4-dihydro-2H-pyrazino[1,2-a]indol-1-one (2.75 g; 10 mmol) was dissolved in diethylether (200 mL) and lithium aluminium hydride (0.78 g, 21 mmol) was added in portions with cooling. The solution was stirred for 2 h at reflux temperature, cooled and hydrolyzed by sequential addition of water (3.0 mL), sodium hydroxide solution (15%, 6.0 mL) and water (6.0 mL). Diethylether was added (100 mL), the mixture was filtered and the filtrate evaporated. The residue was stirred with hexane (20 mL) and diethylether (1 mL) to give the title compound as white solid (2.55 g, 97%). M.p.: 123–125° C., ISP-MS: m/e=255.1 (M+), $\alpha_D^{20}$=–110.0 e) (4R,10aR)-4-Methyl-7-trifluoromethyl-1,2,3,4,10,10a-hexahydro-pyrazino[1,2-a]indole hydrochloride (R)-4-Methyl-7-trifluoromethyl-1,2,3,4-tetrahydro-pyrazino[1,2-a]indole (1.0 g; 4.0 mmol) was dissolved in a tetrahydrofurane/trifluoroacetic acid mixture (1:2; 15 mL) and cooled to 0° C. Sodium borohydride (300 mg; 8.0 mmol) was added in portions and the solution was stirred for 2 h. The reaction mixture was poured into ice water (60 mL) and the pH was adjusted to 14 with concentrated NaOH solution. The mixture was extracted with dichloromethane (3-×75 mL). Organic phases were pooled, dried with MgSO4 and the solvent was evaporated. Chromatography on silica gel (dichloromethane/methanol 9:1) gave the title compound (0.86 g, 85%) as yellowish oil. The compound was precipitated as HCl salt from diethylether solution. White solid, m.p. 221–224° C.; ISP-MS: m/e=257.1 (M+H+), $\alpha_D^{20}$=–48.1.

Example 13

(4R,10aS)-4-Methyl-7-trifluoromethyl-1,2,3,4,10, 10a-hexahydro-pyrazino[1,2-a]indole hydrochloride The title compound was obtained as a side product in example 12 e) in 6.3% yield (64 mg yellowish oil) and precipitated as HCl salt from diethylether. White solid, m.p. 245–250 ° C. dec.; ISP-MS: m/e=257.2 (M+H+), $\alpha_D^{20}$=–101.6.

Example 14

(4R,10aS)-6-Ethyl-4-methyl-1,2,3,4,10,10a-hexahydro-pyrazino[1,2-a]indole a) 7-Ethyl-indole-1-carboxylic acid tert-butyl ester 7-Ethylindole (106.0 g, 0.73 mol) was dissolved in acetonitrile (1 l) and di-tert-butyl dicarbonate (191.0 g, 0.87 mol) and 4-(dimethylamino)pyridine (4.43 g, 36.0 mmol) were added successively. After 4.5 h the reaction mixture was concentrated and the residue was purified by column chromatography over silica gel (0.032–0.060 mm) with n-hexane/tert-butyl methyl ether (9/1) as eluant to yield the desired product as colorless oil (179 g, 100%). EI-MS: m/e=245.2 ([M])

b) 7-Ethyl-indole-1,2-dicarboxylic acid 1-tert-butyl ester 2-ethyl ester 2,2,6,6-Tetramethylpiperidine (2.21 g, 15.6 mmol) was dissolved in 30 mL tetrahydrofuran and cooled down to –75° C. n-Butyllithium (9 mL, 14.3 mmol, 1.6M solution in n-hexane) was added while maintaining the temperature below –70° C. After 50 min., a solution of 3.2 g (13.0 mmol) 7-ethyl-indole-1-carboxylic acid tert-butyl ester in 15 mL tetrahydrofuran was added and the temperature again kept below –70° C. After 50 min., ethyl chloroformate (1.4 mL (14.3 mmol) was added and the temperature was allowed to rise to –50° C. After 1 h the reaction mixture was poured into 30 mL saturated aq. ammonium chloride solution and the phases separated. The aqueous phase was extracted once with 50 mL diethyl ether and the combined organic extractions were washed successively with saturated aq. ammonium chloride solution and water, dried over magnesium sulfate, filtered and evaporated. The crude reaction product was flash-chromatographed over silica gel (0.030–0.060 mm) with n-hexane/tert-butyl methyl ether (39/1) as eluant to give the product as a yellow oil (2.3 g, 56.2%). EI-MS: m/e=317.2 ([M])

c) 7-Ethyl-1H-indole-2-carboxylic acid ethyl ester

7-Ethyl-indole-1,2-dicarboxylic acid 1-tert-butyl ester 2-ethyl ester (76.6 g, 0.24 mol was dissolved in 450 mL dichloromethane and cooled to 0° C. Trifluoroacetic acid (150.0 mL, 1.96 mol) was added within 30 min. and after an additional 45 min. the reaction mixture was concentrated at a rotary evaporator. The residue was dissolved in 300 mL dichloromethane and poured cautiously onto 500 mL saturated aq. sodium bicarbonate solution. The phases were separated and the aqueous phase was extracted twice with dichloromethane. The combined organic extracts were washed with brine, dried over magnesium sulfate, filtered and concentrated on a rotary evaporator. The residue was suspended in 400 mL n-hexane and put in an ultrasonic bath for 15 min. The suspension was filtered and the filter cake was washed with 100 mL n-hexane. This procedure was repeated to give the desired product as a light brown solid (40.2 g, 76.6%). EI-MS: m/e=217.1 ([M])

d) (R)-6-Ethyl-4-methyl-3,4-dihydro-2H-pyrazino[1,2-a]indol-1-one

Potassium tert-butylate (2.17 g, 19.3 mmol) was added to a solution of 7-ethyl-1H-indole-2-carboxylic acid ethyl ester (4.00 g, 18.4 mmol) in N,N-dimethylformamide (100 mL) at 0° C., then after 1 h (S)-5-methyl-2,2-dioxo-[1,2,3]oxathiazolidine-3-carboxylic acid tert-butyl ester (4.81 g, 20.2 mmol) was added and the solution was allowed to reach room temperature over 16 h. The solution was partitioned between 1 M aq. HCl solution (100 mL) and hexane/ethyl acetate 1:1 (200 mL). The organic layer was washed with sat. aq. NaHCO$_3$ solution and brine, dried (MgSO$_4$), and evaporated. The residue was dissolved in dichloromethane (80 mL) and treated with trifluoroacetic acid (20 mL) at 0° C. After removal of the ice bath, the solution was stirred for 30 min, then evaporated under reduced pressure. The residue was dissolved in methanol (100 mL), then after addition of K$_2$CO$_3$ (25.4 g, 184 mmol) the mixture was stirred for 16 h at room temperature. Then water (200 mL) and ethyl acetate (200 mL) were added, the organic layer was separated, washed with brine, dried (MgSO$_4$), and evaporated. Chromatography (70 g SiO$_2$, hexane/ethyl acetate gradient) yielded a foam which was precipitated with hexane to produce the title compound (1.20 g, 29%). White solid. EI-MS: m/e=228.3 (M$^+$). The optical purity was determined by gas chromatography, using a chiral BGB-176-SE column (15×0.25 mm), to be 96.2% e.e.

e) (4R,10aS)-6-Ethyl-4-methyl-3,4,10,10a-tetrahydro-2H-pyrazino[1,2-a]indol-1-one Magnesium turnings (87 mg, 3.6 mmol) were added to a solution of (R)-6-Ethyl-4-methyl-3,4-dihydro-2H-pyrazino[1,2-a]indol-1-one (82 mg, 0.36 mmol) in methanol (4 mL). After hydrogen gas started to evolve, the reaction mixture was kept at 10–20° C. and stirred for 2 h to dissolve the magnesium completely. Then the reaction mixture was poured onto 3 mL ice-cold 1 M aq. HCl, neutralized with 1 M aq. potassium phosphate solution (pH 6.85), and extracted with ethyl acetate. The organic layer was washed with brine, dried (MgSO$_4$), and evaporated to yield the title compound (80 mg, 97%). White solid. ISP-MS: m/e=231.2 ([M+H]$^+$).

f) (4R,10aS)-6-Ethyl-4-methyl-1,2,3,4,10,10a-hexahydro-pyrazino[1,2-a]indole

Lithium aluminium hydride (37 mg, 0.97 mmol) was added to a solution of (4R,10aS)-6-ethyl-4-methyl-3,4,10,10a-tetrahydro-2H-pyrazino[1,2-a]indol-1-one (56 mg, 0.24 mmol) in tetrahydrofuran (3 mL) and the resulting suspension was heated to reflux for 1 h. After cooling the reaction was quenched by careful addition of 1 M aqueous sodium potassium tartrate solution (5 mL). Then methanol (5 mL) and ethyl acetate (5 mL) were added, the organic layer was separated, washed with brine, dried (MgSO$_4$), and evaporated. Chromatography on 20 g SiO$_2$ (CH$_2$Cl$_2$/MeOH/NH$_4$OH 95:5:0.1) yielded the title compound (20 mg, 38%). White solid. ISP-MS: m/e=217.3 ([M+H]$^+$).

Example 15

(4R,10aR)-6-Ethyl-4-methyl-1,2,3,4,10,10a-hexahydro-pyrazino[1,2-a]indole a) (R)-6-Ethyl-4-methyl-1,2,3,4-tetrahydro-pyrazino[1,2-a]indole Lithium aluminium hydride (532 mg) was added in portions to a solution of (R)-6-ethyl-4-methyl-3,4-dihydro-2H-pyrazino[1,2-a]indol-1-one (800 mg, 3.50 mmol) in tetrahydrofuran (30 mL) and the resulting suspension was heated to reflux for 1 h. After cooling the reaction was quenched by careful addition of 1 M aqueous sodium potassium tartrate solution (50 mL). Then methanol (50 mL) and ethyl acetate (50 mL) were added, the organic layer was separated, washed with brine, dried (MgSO$_4$), and evaporated to yield the title compound (750 mg, 100%). White solid. ISP-MS: m/e=215.3 ([M+H]$^+$).

b) (4R,10aR)-6-Ethyl-4-methyl-1,2,3,4,10,10a-hexahydro-pyrazino[1,2-a]indole

This compound was prepared in accordance with the general method of example 12e) from (R)-6-ethyl-4-methyl-1,2,3,4-tetrahydro-pyrazino[1,2-a]indole. White solid. ISP-MS: m/e=217.4 ([M+H]$^+$).

Example 16

(4R,10aR)-8-Bromo-4-methyl-7-trifluoromethyl-1,2,3,4,10,10a-hexahydro-pyrazino[1,2-a]indole hydrochloride a) (4R,10aR)-4-Methyl-7-trifluoromethyl-3,4,10,10a-tetrahydro-1H-pyrazino[1,2-a]indole-2-carboxylic acid tert-butyl ester (4R,10aR)-4-Methyl-7-trifluoromethyl-1,2,3,4,10,10a-hexahydro-pyrazino[1,2-a]indole (0.64 g, 2.5 mmol) were dissolved in dichloromethane (15 mL) and di-tert-butyl dicarbonate (0.65 g, 3 mmol) dissolved in dichloromethane (2 mL) was added. The mixture was stirred for 1 h and solvent was removed in vacuo. Chromatography on silica gel (n-hexane/diethylether 6:1) yielded the tide product as a colorless oil (0.86 g, 96%). ISP-MS: m/e=357.3 (M+H$^+$).

b) (4R,10aR)-8-Bromo-4-methyl-7-trifluoromethyl-3,4,10,10a-tetrahydro-1H-pyrazino[1,2-a]indole-2-carboxylic acid tert-butyl ester 4-Methyl-7-trifluoromethyl-3,4,10,10a-tetrahydro-1H-pyrazino[1,2-a]indole-2-carboxylic acid tert-butyl ester (0.83 g; 2.4 mmol) was dissolved in dimethylformamide (7 mL) and N-bromosuccinimide (0.43 g, 2.5 mmol) was added in portions. The mixture was stirred for 1 h, added to ice water (500 mL) and extracted with diethylether (2×150 mL). Organic phases were pooled, washed with water, dried with MgSO$_4$ and the solvent was removed in vacuo. Chromatography on silica gel (n-hexane/diethylether 4:1) yielded the title product as a colorless wax (0.99 g, 98%). ISP-MS: m/e=435.3, 437.3 (M+H$^+$).

c) (4R,10aR)-8-Bromo-4-methyl-7-trifluoromethyl-1,2,3,4,10,10a-hexahydro-pyrazino[1,2-a]indole hydrochloride 8-Bromo-4-methyl-7-trifluoromethyl-3,4,10,10a-tetrahydro-1H-pyrazino[1,2-a]indole-2-carboxylic acid tert-butyl ester (0.35 g, 0.8 mmol) were dissolved in dichloromethane (12 mL) and trifluoroacetic acid was added (3 mL). The mixture was stirred for 1 h, added to 1 N sodium hydroxide solution (50 mL) and extracted with dichloromethane (3×40 mL). Organic phases were pooled, washed with brine, dried with MgSO$_4$ and the solvent was removed in vacuo. Chromatography on silica gel (dichloromethane/methanol 19:1) yielded the title compound as a colorless oil which was precipitated as HCl salt from diethylether (0.2 g; 73%). ISP-MS: m/e=335.2, 337.2 (M+H$^+$), $\alpha_D^{20}$=−48.6.

Example 17

(4R,10aR)-4,6,7-Trimethyl-1,2,3,4,10,10a-hexahydro-pyrazino[1,2-a]indole hydrochloride a) (R)-1-(2-tert-Butoxycarbonylamino-1-methyl-ethyl)-6,7-dimethyl-1H-indole-2-carboxylic acid ethyl ester The title compound, ISP-MS: m/e=375.4 (M+H$^+$), was prepared in accordance with the general method of example 12b) from 6,7-dimethyl-1H-indole-2-carboxylic acid ethyl ester and (S)-5-methyl-2,2-dioxo-[1,2,3]oxathiazolidine-3-carboxylic acid tert-butyl ester.

b) (R)-4,6,7-Trimethyl-3,4-dihydro-2H-pyrazino[1,2-a]indol-1-one

The title compound, ISP-MS: m/e=229.2 (M+H$^+$) and $\alpha_D^{20}$=−49.8, was prepared in accordance with the general method of example 12c) from (R)-1-(2-tert-butoxycarbonylamino-1-methyl-ethyl)-6,7-dimethyl-1H-indole-2-carboxylic acid ethyl ester.

c) (R)-4,6,7-Trimethyl-1,2,3,4-tetrahydro-pyrazino[1,2-a]indole

The title compound was prepared in accordance with the general method of example 12d) from (R)-4,6,7-trimethyl-3,4-dihydro-2H-pyrazino[1,2-a]indol-1-one.

d) (4R,10aR)-4,6,7-Trimethyl-1,2,3,4,10,10a-hexahydro-pyrazino[1,2-a]indole hydrochloride The title compound, ISP-MS: m/e=217.3 (M+H$^+$) and $\alpha_D^{20}$=−8.1, was prepared in accordance with the general method of example 12e) from (R)-4,6,7-trimethyl-1,2,3,4-tetrahydro-pyrazino[1,2-a]indole.

Example 18

(4R,10aR)-7-Bromo-4-methyl-1,2,3,4,10,10a-hexahydro-pyrazino[1,2-a]indole hydrochloride (1:1.25)

a) (R)-6-Bromo-1-(2-tert-butoxycarbonylamino-1-methyl-ethyl)-1H-indole-2-carboxylic acid ethyl ester The title compound, ISP-MS: m/e=425.3, 427.3 (M+H$^+$), was prepared in accordance with the general method of example 12b) from 6-bromo-1H-indole-2-carboxylic acid ethyl ester and (S)-5-methyl-2,2-dioxo-[1,2,3]oxathiazolidine-3-carboxylic acid tert-butyl ester.

b) (R)-7-Bromo-4-methyl-3,4-dihydro-2H-pyrazino[1,2-a]indol-1-one

The title compound, ISP-MS: m/e=279.1, 281.1 (M+H$^+$) and $\alpha_D^{20}$=−8.9, was prepared in accordance with the general method of example 12c) from (R)-6-bromo-1-(2-tert-butoxycarbonylamino-1-methyl-ethyl)-1H-indole-2-carboxylic acid ethyl ester.

c) (R)-7-Bromo-4-methyl-1,2,3,4-tetrahydro-pyrazino[1,2-a]indole

The title compound, ISP-MS: m/e=265.2, 267.2 (M+H$^+$) and $\alpha_D^{20}$=−115.7, was prepared in accordance with the general method of example 12d) from (R)-7-bromo-4-methyl-3,4-dihydro-2H-pyrazino[1,2-a]indol-1-one.

d) (4R,10aR)-7-Bromo-4-methyl-1,2,3,4,10,10a-hexahydro-pyrazino[1,2-a]indole hydrochloride The title compound, ISP-MS: m/e=267.2, 269.2 (M+H$^+$) and $\alpha_D^{20}$=−44.9, was prepared in accordance with the general method of example 12e) from (R)-7-bromo-4-methyl-1,2,3,4-tetrahydro-pyrazino[1,2-a]indole.

Example 19

(4R,10aR)-4,8-Dimethyl-7-trifluoromethyl-1,2,3,4,10,10a-hexahydro-pyrazino[1,2-a]indole hydrochloride a) (4R,10aR)-4,8-Dimethyl-7-trifluoromethyl-3,4,10,10a-tetrahydro-1H-pyrazino[1,2-a]indole-2-carboxylic acid tert-butyl ester (4R,10aR)-8-Bromo-4-methyl-7-trifluoromethyl-3,4,10,10a-tetrahydro-1H-pyrazino[1,2-a]indole-2-carboxylic acid tert-butyl ester (0.38 g, 0.8 mmol) and methyl iodide (0.25 g, 1.6 mmol) were dissolved in tert-butylmethylether (3 mL). A solution of methyl lithium in diethylether (0.66 mL, 1.6 M) was added with cooling (0° C.) and stirring. The mixture was stirred for ½ h at 0° C., water (25 mL) was added and the mixture was extracted with diethylether (2×20 mL). Organic phases were pooled, dried with MgSO$_4$ and the solvent was removed in vacuo. Chromatography on silica gel (n-hexane/diethylether 4:1) yielded the title product as light yellow oil (0.20 g, 63%).

b) (4R,10aR)-4,8-Dimethyl-7-trifluoromethyl-1,2,3,4,10,10a-hexahydro-pyrazino[1,2-a]indole hydrochloride The title compound, ISP-MS: m/e=271.3 (M+H$^+$) and $\alpha_D^{20}$=−43.3, was prepared in accordance with the general method of example 16c) from (4R,10aR)-4,8-dimethyl-7-trifluoromethyl-3,4,10,10a-tetrahydro-1H-pyrazino[1,2-a]indole-2-carboxylic acid tert-butyl ester.

Example 20

(4R,10aR)-9-Chloro-4-methyl-1,2,3,4,10,10a-hexahydro-pyrazino[1,2-a]indole hydrochloride a) (R)-1-(2-tert-Butoxycarbonylamino-1-methyl-ethyl)-4-chloro-1H-indole-2-carboxylic acid ethyl ester The title compound, m.p.: 115–119° C., ISP-MS: m/e=381.3 (M+H$^+$) and $\alpha_D^{20}$=−8.0, was prepared in accordance with the general method of example 12b) from 4-chloro-1H-indole-2-carboxylic acid ethyl ester and (S)-5-methyl-2,2-dioxo-[1,2,3]oxathiazolidine-3-carboxylic acid tert-butyl ester.

b) (R)-9-Chloro-4-methyl-3,4-dihydro-2H-pyrazino[1,2-a]indol-1-one

The title compound, m.p.: 180–184° C., EI-MS: m/e=234.1 (M$^{30}$) and $\alpha_D^{20}$=+20.2 prepared in accordance with the general method of example 12c) from (R)-1-(2-tert-butoxycarbonylamino-1-methyl-ethyl)-4-chloro-1H-indole-2-carboxylic acid ethyl ester.

c) (R)-9-Chloro-4-methyl-1,2,3,4-tetrahydro-pyrazino[1,2-a]indole hydrochloride

The title compound, ISP-MS: m/e=221.2 (M+H$^+$) and $\alpha_D^{20}$=−110.6, was prepared in accordance with the general method of example 12d) from (R)-9-chloro-4-methyl-3,4-dihydro-2H-pyrazino[1,2-a]indol-1-one and precipitated as HCl salt from diethylether.

d) (4R,10aR)-9-Chloro-4-methyl-1,2,3,4,10,10a-hexahydro-pyrazino[1,2-a]indole hydrochloride The title compound, ISP-MS: m/e=223.2 (M+H$^+$) and $\alpha_D^{20}$=−57.4, was prepared in accordance with the general method of example 12e) from (R)-9-chloro-4-methyl-1,2,3,4-tetrahydro-pyrazino[1,2-a]indole.

Example 21

(4R,10aS)-4,8-Dimethyl-7-trifluoromethyl-1,2,3,4,10,10a-hexahydro-pyrazino[1,2-a]indole hydrochloride a) 5-Methyl-6-trifluoromethyl-indole-1-carboxylic acid tert-butyl ester The title compound, EI-MS: m/e=299.1 (M$^+$), was prepared in accordance with the general method of example 14a) from 5-methyl-6-trifluoromethyl-1H-indole b) 5-Methyl-6-trifluoromethyl-indole-1,2-dicarboxylic acid 1-tert-butyl ester 2-ethyl ester The title compound, EI-MS: m/e=371.1 (M⁺), was prepared in accordance with the general method of example 14b) from 5-methyl-6-trifluoromethyl-indole-1-carboxylic acid tert-butyl ester c) 5-Methyl-6-trifluoromethyl-1H-indole-2-carboxylic acid ethyl ester The title compound, m.p.: 176–178° C. and EI-MS: m/e=271.1 (M⁺), was prepared in accordance with the general method of example 14c) from 5-methyl-6-trifluoromethyl-indole-1,2-dicarboxylic acid 1-tert-butyl ester 2-ethyl ester d) (R)-1-(2-tert-Butoxycarbonylamino-1-methyl-ethyl)-5-methyl-6-trifluoromethyl-1H-indole-2-carboxylic acid ethyl ester The title compound, m.p.: 103–105° C., EI-MS: m/e=428.1 (M⁺) and $\alpha_D^{20}$=–40.3, was prepared in accordance with the general method of example 12b) from 5-methyl-6-trifluoromethyl-1H-indole-2-carboxylic acid ethyl ester and (S)-5-methyl-2,2-dioxo-[1,2,3]oxathiazolidine-3-carboxylic acid tert-butyl ester.

e) (R)-4,8-Dimethyl-7-trifluoromethyl-3,4-dihydro-2H-pyrazino[1,2-a]indol-1-one

The title compound, ISP-MS: m/e=283.1 (M+H⁺) and $\alpha_D^{20}$=+4.3, was prepared in accordance with the general method of example 12c) from (R)-1-(2-tert-butoxycarbonylamino-1-methyl-ethyl)-5-methyl-6-trifluoromethyl-1H-indole-2-carboxylic acid ethyl ester.

f) (4R,10aS)-4,8-Dimethyl-7-trifluoromethyl-1,2,3,4,10,10a-hexahydro-pyrazino[1,2-a]indole hydrochloride m.p.: 200–205° C., ISP-MS: m/e=271.3 (M+H⁺) and $\alpha_D^{20}$=–103.1, (R)-4,8-Dimethyl-7-trifluoromethyl-3,4-dihydro-2H-pyrazino[1,2-a]indol-1-one.

Example 22

(4R,10aR)-7-Chloro-8-fluoro-4-methyl-1,2,3,4,10,10a-hexahydro-pyrazino[1,2-a]indole hydrochloride a) (R)-1-(2-tert-Butoxycarbonylamino-1-methyl-ethyl)-6-chloro-5-fluoro-1H-indole-2-carboxylic acid ethyl ester The title compound, ISP-MS: m/e=399.4 (M+H⁺), was prepared in accordance with the general method of example 12b) from 6-chloro-5-fluoro-1H-indole-2-carboxylic acid ethyl ester and (S)-5-methyl-2,2-dioxo-[1,2,3]oxathiazolidine-3-carboxylic acid tert-butyl ester.

b) (R)-7-Chloro-8-fluoro-4-methyl-3,4-dihydro-2H-pyrazino[1,2-a]indol-1-one

The title compound, ISP-MS: m/e=253.1 (M+H⁺) and $\alpha_D^{20}$=–6.7, was prepared in accordance with the general method of example 12c) from (R)-1-(2-tert-butoxycarbonylamino-1-methyl-ethyl)-6-chloro-5-fluoro-1H-indole-2-carboxylic acid ethyl ester.

c) (R)-7-Chloro-8-fluoro-4-methyl-1,2,3,4-tetrahydro-pyrazino[1,2-a]indole

The title compound, ISP-MS: m/e=239.2 (M+H⁺) and $\alpha_D^{20}$=–121.7, was prepared in accordance with the general method of example 12d) from (R)-7-chloro-8-fluoro-4-methyl-3,4-dihydro-2H-pyrazino[1,2-a]indol-1-one.

d) (4R,10aR)-7-Chloro-8-fluoro-4-methyl-1,2,3,4,10,10a-hexahydro-pyrazino[1,2-a]indole hydrochloride The title compound, ISP-MS: m/e=241.3 (M+H⁺) and $\alpha_D^{20}$=–48.2, was prepared in accordance with the general method of example 12e) from (R)-7-chloro-8-fluoro-4-methyl-1,2,3,4-tetrahydro-pyrazino[1,2-a]indole.

Example 23

(4R,10aS)-8-Bromo-4-methyl-7-trifluoromethyl-1,2,3,4,10,10a-hexahydro-pyrazino[1,2-a]indole hydrochloride a) (4R,10aS)-4-Methyl-7-trifluoromethyl-3,4,10,10a-tetrahydro-1H-pyrazino[1,2-a]indole-2-carboxylic acid tert-butyl ester The title compound, ISP-MS: m/e=357.3 (M+H⁺), was prepared in accordance with the general method of example 16a) from (4R,10aS)-4-methyl-7-trifluoromethyl-1,2,3,4,10,10a-hexahydro-pyrazino[1,2-a]indole.

b) (4R,10aS)-8-Bromo-4-methyl-7-trifluoromethyl-3,4,10,10a-tetrahydro-1H-pyrazino[1,2-a]indole-2-carboxylic acid tert-butyl ester The title compound, ISP-MS: m/e=435.3, 437.3 (M+H⁺), was prepared in accordance with the general method of example 16b) from (4R,10aS)-4-methyl-7-trifluoromethyl-3,4,10,10a-tetrahydro-1H-pyrazino[1,2-a]indole-2-carboxylic acid tert-butyl ester.

c) (4R,10aS)-8-Bromo-4-methyl-7-trifluoromethyl-1,2,3,4,10,10a-hexahydro-pyrazino[1,2-a]indole hydrochloride The title compound, ISP-MS: m/e=335.1, 337.1 (M+H⁺) and $\alpha_D^{20}$=–79.1, was prepared in accordance with the general method of example 16c) from (4R,10aS)-8-Bromo-4-methyl-7-trifluoromethyl-3,4,10,10a-tetrahydro-1H-pyrazino[1,2-a]indole-2-carboxylic acid tert-butyl ester.

Example 24

(4R,10aR)-4-Methyl-1,2,3,4,10,10a-hexahydro-pyrazino[1,2-a]indole-7-carbonitrile hydrochloric acid a) (4R,10aR)-7-Bromo-4-methyl-3,4,10,10a-tetrahydro-1H-pyrazino[1,2-a]indole-2-carboxylic acid tert-butyl ester The title compound, ISP-MS: m/e=367.1, 369.1 (M+H⁺) and $\alpha_D^{20}$=–36.9, was prepared in accordance with the general method of example 16a) from (4R,10aR)-7-bromo-4-methyl-1,2,3,4,10,10a-hexahydro-pyrazino[1,2-a]indole.

b) (4R,10aR)-7-Cyano-4-methyl-3,4,10,10a-tetrahydro-1H-pyrazino[1,2-a]indole-2-carboxylic acid tert-butyl ester (4R,10aR)-7-Bromo-4-methyl-3,4,10,10a-tetrahydro-1H-pyrazino[1,2-a]indole-2-carboxylic acid tert-butyl ester (0.1 g) was dissolved in dioxane (2 mL) and copper(I)cyanide (0.1 g), tris-(dibenzylideneacetone)dipalladium chloroform complex (12 mg), 1,1'-bis(diphenylphosphino)ferrocene (24 mg) and tetraethylammonium cyanide (43 mg) were added. The mixture was heated to reflux for 18 h, cooled, filtered and the filter cake was washed with ethyl acetate. Saturated sodium bicarbonate solution (30 mL) was added to the filtrate, the phases were separated, the water phase was extracted with ethyl acetate (2-×20 mL) and the organic phases washed twice with saturated bicarbonate solution. Organic phases were pooled, dried with $MgSO_4$ and the solvent removed in vacuo. Chromatography on silica gel (n-hexane/ethyl acetate 6:1) yielded the title compound as light yellow wax (34 mg; 40%). ISP-MS: m/e=314.2 (M+H⁺).

c) (4R,10aR)-4-Methyl-1,2,3,4,10,10a-hexahydro-pyrazino[1,2-a]indole-7-carbonitrile hydrochloric acid The title compound, ISP-MS: m/e=214.3 (M+H$^+$), was prepared in accordance with the general method of example 16c) from (4R,10aR)-7-cyano-4-methyl-3,4,10,10a-tetrahydro-1H-pyrazino[1,2-a]indole-2-carboxylic acid tert-butyl ester.

Example 25

(4R,10aR)-9-Chloro-6-fluoro-4-methyl-1,2,3,4,10,10a-hexahydro-pyrazino[1,2-a]indole hydrochloride a) (5-Chloro-2-fluoro-phenyl)-hydrazine 5-Chloro-2-fluoroaniline (25 g, 172 mmol) was added to conc. hydrochloric acid (150 mL, 37%). The mixture was cooled (−10° C.) and a solution of sodium nitrite (11.9 g, 172 mmol) in water (193 mL) was added slowly (<−5° C.). This done, a solution of tin(II)chloride (118 g, 618 mmol) in conc. hydrochloric acid (116 mL) was added slowly (−6° C.). The mixture was stirred for 1 h, filtered through Celite® and the filter cake washed extensively with water. The filtrate was adjusted to pH 14 with conc. sodium hydroxide solution and the suspension extracted with diethylether. Organic phases were pooled, washed with brine, dried with MgSO$_4$ and the solvent was removed in vacuo to yield the title compound as yellow solid (22.9 g, 83%), EI-MS: m/e=160.0 (M$^+$).

b) 2-[(5-Chloro-2-fluoro-phenyl)-hydrazono]-propionic acid ethyl ester (5-Chloro-2-fluoro-phenyl)-hydrazine (22.5 g, 140 mmol) was dissolved in dichloromethane (80 mL). Ethyl pyruvate (16.3 mL, 140 mmol) was added slowly to this solution at room temperature. The mixture was stirred for another1 h at room temperature, added to water and extraxcted with dichloromethane. Organic phases were pooled, washed subsequently with hydrochloric acid (1 N) and brine and dried with MgSO$_4$. Solvents were removed in vacuo and the residue was triturated with n-hexane to yield the title product as beige solid (22.8 g, 62.9%), ISP-MS: m/e=259.1 (M+H$^+$).

c) 4-Chloro-7-fluoro-1H-indole-2-carboxylic acid ethyl ester

2-[(5-Chloro-2-fluoro-phenyl)-hydrazono]-propionic acid ethyl ester (13.2 g, 51 mmol) was dissolved in toluene, p-toluenesulfonic acid (10 g, 51 mmol) was added and the mixture was heated to reflux for 24 h with separation of water. The mixture was cooled, neutralized with saturated sodium bicarbonate (400 mL) and extracted thrice with ethyl acetate. Organic phases were pooled, washed with brine, dried with MgSO$_4$ and the solvent was removed in vacuo. The residue was triturated with hexane to yield the title product as yellowish solid (2.9 g, 23%); EI-MS: m/e=241.1 (M$^+$).

d) (R)-1-(2-tert-Butoxycarbonylamino-1-methyl-ethyl)-4-chloro-7-fluoro-1H-indole-2-carboxylic acid ethyl ester The title compound, ISP-MS: m/e=399.4 (M+H$^+$) and $\alpha_D^{20}$=−54.7, was prepared in accordance with the general method of example 12b) from 4-chloro-7-fluoro-1H-indole-2-carboxylic acid ethyl ester and (S)-5-methyl-2,2-dioxo-[1,2,3]oxathiazolidine-3-carboxylic acid tert-butyl ester.

e) (R)-9-Chloro-6-fluoro-4-methyl-3,4-dihydro-2H-pyrazino[1,2-a]indol-1-one

The title compound, ISP-MS: m/e=253.1 (M+H$^+$) and $\alpha_D^{20}$=+22.7, was prepared in accordance with the general method of example 12c) from (R)-1-(2-tert-butoxycarbonylamino-1-methyl-ethyl)-4-chloro-7-fluoro-1H-indole-2-carboxylic acid ethyl ester.

f) (4R,10aR)-9-Chloro-6-fluoro-4-methyl-1,2,3,4,10,10a-hexahydro-pyrazino[1,2-a]indole hydrochloride (R)-9-Chloro-6-fluoro-4-methyl-3,4-dihydro-2H-pyrazino[1,2-a]indol-1-one 4.7 mmol) was dissolved in methanol and magnesium (0.69 g, 28.5 mmol) was added with stirring. Stirring was continued for 3 h at room temperature, the mixture was poured onto ice water and hydrochloric acid (1 N, 23 mL) was added. The pH was adjusted to neutral with potassium phosphate buffer (1 M, pH 6.85) and the mixture was extracted with ethyl acetate. Organic phase were pooled, washed with brine, dried with MgSO$_4$ and the solvent was removed in vacuo to yield a mixture of (4R,10aR)- and (4R,10aS)-9-chloro-6-fluoro-4-methyl-3,4,10,10a-tetrahydro-2H-pyrazino[1,2-a]indol-1-one. Without further purification this mixture (1.2 g) was dissolved in diethylether (50 mL), lithium aluminium hydride (460 mg, 12.0 mmol) was added and the mixture was heated to reflux for 4 h. The solution was cooled and hydrolyzed by sequential addition of water (6.0 mL), sodium hydroxide solution (15%, 12.0 mL) and water (12.0 mL). Diethylether was added (300 mL), the mixture was filtered and the filtrate was evaporated after drying with MgSO$_4$. Chromatography on silica gel (dichloromethane/methanol 97:3) separated the title compound (0.23 g; 20%) from the isomeric (4R,10aS)-9-chloro-6-fluoro-4-methyl-1,2,3,4,10,10a-hexahydro-pyrazino[1,2-a]indole. The title compound was characterized as its HCl salt which precipitated from diethylether, ISP-MS: m/e=241.3 (M+H$^+$) and $\alpha_D^{20}$=−18.4.

Example 26

(4R,10aR)-6,7-Difluoro-4-methyl-1,2,3,4,10,10a-hexahydro-pyrazino[1,2-a]indole hydrochloride a) 2-[(2,3-Difluoro-phenyl)-hydrazono]-propionic acid ethyl ester The title compound, EI-MS: m/e=242.1 (M$^+$), was prepared in accordance with the general method of example 25b) from 2,3-difluorophenyl hydrazine and ethyl pyruvate.

b) 6,7-Difluoro-1H-indole-2-carboxylic acid ethyl ester

The title compound, EI-MS: m/e=225.1 (M$^+$), was prepared in accordance with the general method of example 25c) from 2-[(2,3-difluoro-phenyl)-hydrazono]-propionic acid ethyl ester.

c) (R)-1-(2-tert-Butoxycarbonylamino-1-methyl-ethyl)-6,7-difluoro-1H-indole-2-carboxylic acid ethyl ester The title compound, ISP-MS: m/e=383.3 (M+H$^+$), was prepared in accordance with the general method of example 12b) from 6,7-difluoro-1H-indole-2-carboxylic acid ethyl ester and (S)-5-methyr-2,2-dioxo-[1,2,3]oxathiazolidine-3-carboxylic acid tert-butyl ester.

d) (R)-6,7-Difluoro-4-methyl-3,4-dihydro-2H-pyrazino[1,2-a]indol-1-one

The title compound, EI-MS: m/e=236.1 (M$^+$), was prepared in accordance with the general method of example 12c) from (R)-1-(2-tert-butoxycarbonylamino-1-methyl-ethyl)-6,7-difluoro-1H-indole-2-carboxylic acid ethyl ester.

e) (4R,10aR)-6,7-Difluoro-4-methyl-1,2,3,4,10,10a-hexahydro-pyrazino[1,2-a]indole hydrochloride The title compound, EI-MS: m/e=224.2 (M$^+$) and $\alpha_D^{20}$=−27.3, was prepared in accordance with the general method of example 25f) from (R)-6,7-difluoro-4-methyl-3,4-dihydro-2H-pyrazino[1,2-a]indol-1-one and separated from its (4R,10aS)-isomer by chromatography on silica gel.

Example 27

(4R,10aS)-6,7-Difluoro-4-methyl-1,2,3,4,10,10a-hexahydro-pyrazino[1,2-a]indole hydrochloride The title compound, EI-MS: m/e=224.2 (M$^+$) and $\alpha_D^{20}$=−37.8, was prepared in accordance with the general method of example 25f) from (R)-6,7-difluoro-4-methyl-3,4-dihydro-2H-pyrazino[1,2-a]indol-1-one and separated from its (4R,10aR)-isomer by chromatography on silica gel.

Example 28

(4R,10aR)-7-Chloro-6-fluoro-4-methyl-1,2,3,4,10,10a-hexahydro-pyrazino[1,2-a]indole hydrochloride a) (3-Chloro-2-fluoro-phenyl)-hydrazine The title compound, EI-MS: m/e=200.0 (M$^+$), was prepared in accordance with the general method of example 25a) from 3-chloro-2-fluoroaniline.

b) 2-[(3-Chloro-2-fluoro-phenyl)-hydrazono]-propionic acid ethyl ester

The title compound, EI-MS: m/e=258.1 (M$^+$), was prepared in accordance with the general method of example 25b) from (3-Chloro-2-fluoro-phenyl)-hydrazine and ethyl pyruvate.

c) 6-Chloro-7-fluoro-1H-indole-2-carboxylic acid ethyl ester

The title compound, EI-MS: m/e=241.0 (M$^+$), was prepared in accordance with the general method of example 25c) from 2-[(3-chloro-2-fluoro-phenyl)-hydrazono]-propionic acid ethyl ester.

d) (R)-1-(2-tert-Butoxycarbonylamino-1-methyl-ethyl)-6-chloro-7-fluoro-1H-indole-2-carboxylic acid ethyl ester The title compound, ISP-MS: m/e=399.4 (M+H$^+$), was prepared in accordance with the general method of example 12b) from 6-chloro-7-fluoro-1H-indole-2-carboxylic acid ethyl ester and (S)-5-methyl-2,2-dioxo-[1,2,3]oxathiazolidine-3-carboxylic acid tert-butyl ester.

e) (R)-7-Chloro-6-fluoro-4-methyl-3,4-dihydro-2H-pyrazino[1,2-a]indol-1-one

The title compound, EI-MS: m/e=252.1 (M$^+$), was prepared in accordance with the general method of example 12c) from (R)-1-(2-tert-butoxycarbonylamino-1-methyl-ethyl)-6-chloro-7-fluoro-1H-indole-2-carboxylic acid ethyl ester.

f) (4R,10aR)-7-Chloro-6-fluoro-4-methyl-1,2,3,4,10,10a-hexahydro-pyrazino[1,2-a]indole hydrochloride The title compound, ISP-MS: m/e=241.3 (M+H$^+$) and $\alpha_D^{20}$=−39.1, was prepared in accordance with the general method of example 25f) from (R)-7-chloro-6-fluoro-4-methyl-3,4-dihydro-2H-pyrazino[1,2-a)indol-1-one and separated from its (4R,10aS)-isomer by chromatography on silica gel.

Example 29

(4RS,10aRS)-7-Bromo-4-ethyl-1,2,3,4,10,10a-hexahydro-pyrazino[1,2-a]indole a) (RS)-5-ethyl-2,2-dioxo-[1,2,3]oxathiazolidine-3-carboxylic acid tert-butyl ester The title compound was prepared in accordance to the general method of example 12a) from (RS)-(2-hydroxybutyl)-carbamic acid tert-butyl ester. White solid, m.p. 116–118° C. (dec.).

b) (RS)-7-Bromo-4-ethyl-3,4-dihydro-2H-pyrazino[1,2-a]indol-1-one

The title compound (ISP-MS: m/e=293.2, 295.2 ([M+H]$^+$)) was produced in accordance with the general method of example 14d) from 6-bromo-1H-indole-2-carboxylic acid ethyl ester and (RS)-5-ethyl-2,2-dioxo-[1,2,3]oxathiazolidine-3-carboxylic acid tert-butyl ester. White solid.

c) (RS)-7-Bromo-4-ethyl-1,2,3,4-tetrahydro-pyrazino[1,2-a]indole

The title compound, ISP-MS: m/e=279.1, 281.2 ([M+H]$^+$), was produced in accordance with the general method of example 12d) from (RS)-7-bromo-4-ethyl-3,4-dihydro-2H-pyrazino[1,2-a]indol-1-one. Colorless oil.

d) (4RS,10aRS)-7-Bromo-4-ethyl-1,2,3,4,10,10a-hexahydro-pyrazino[1,2-a]indole

The title compound, m/e=281.1, 283.1 ([M+H]$^+$), was produced from (RS)-7-bromo-4-ethyl-1,2,3,4-tetrahydro-pyrazino[1,2-a]indole in accordance with the general method of example 12e) and separated from the isomeric (4RS,10aSR)-7-Bromo-4-ethyl-1,2,3,4,10,10a-hexahydro-pyrazino[1,2-a]indole, by chromatography on silica gel. Colorless oil.

Example 30

(4RS,10aSR)-7-Bromo-4-ethyl-1,2,3,4,10,10a-hexahydro-pyrazino[1,2-a]indole

The title compound, m/e=281.1, 283.1 ([M+H]$^+$), was produced as described in example 29d). Colorless gum.

Example 31

(4RS,10aRS)-6,7,8-Tribromo-4-ethyl-1,2,3,4,10,10a-hexahydro-pyrazino[1,2-a]indole Bromine (0.2 M solution in acetic acid, 0.36 mL, 72 µmol) was added dropwise to a solution of (4RS,10aRS)-7-bromo-4-ethyl-1,2,3,4,10,10a-hexahydro-pyrazino[1,2-a]indole (20 mg, 71 [mol) and sodium acetate (5.8 mg, 72 µmol) in acetic acid (0.5 mL) at room temperature. After 5 min the reaction mixture was diluted with ethyl acetate, washed with 1 M aq. sodium hydroxide solution and brine, dried (MgSO$_4$), and evaporated. Chromatography on SiO$_2$ (CH$_2$Cl$_2$/MeOH/NH$_4$OH 95:5:0.25) yielded the title compound (16 mg, 50%). Colorless gum, m/e=437.1, 439.1, 441.1, 443.1 ([M+H]$^+$).

Example 32

(4RS,10aRS)-7,8-Dibromo-4-ethyl-1,2,3,4,10,10a-hexahydro-pyrazino[1,2-a]indole a) (4RS,10aRS)-7-Bromo-4-ethyl-3,4,10,10a-tetrahydro-1H-pyrazino[1,2-a]indole-2-carboxylic acid tert-butyl ester The title compound, m/e=380.1, 382.1 (M$^+$), was produced in accordance with the general method of example 16a) from (4RS,10aRS)-7-bromo-4-ethyl-1,2,3,4,10,10a-Xexahydro-pyrazino[1,2-a]indole. Colorless waxy solid.

b) (4RS,10aRS)-7,8-Dibromo-4-ethyl-3,4,10,10a-tetrahydro-1H-pyrazino[1,2-a]indole-2-carboxylic acid tert-butyl ester The title compound, m/e=459.2,461.2,463.2 ([M+H]$^+$), was produced in accordance with the general method of example 16b) from (4RS,10aRS)-7-bromo-4-ethyl-3,4,10,10a-tetrahydro-1H-pyrazino[1,2-a]indole-2-carboxylic acid tert-butyl ester. Colorless gum.

c) (4RS,10aRS-7,8-Dibromo-4-ethyl-1,2,3,4,10,10a-hexahydro-pyrazino[1,2-a]indole The title compound, m/e=359.0, 361.0, 363.0 ([M+H]$^+$), was produced in accordance with the general method of example 16c) from (4RS,10aRS)-7,8-Dibromo-4-ethyl-3,4,10,10a-tetrahydro-1H-pyrazino[1,2-a]indole-2-carboxylic acid tert-butyl ester. Colorless gum.

Examples 33 and 34

(4R,10aR)-7-Bromo-4-ethyl-1,2,3,4,10,10a-hexahydro-pyrazino[1,2-a]indole and (4S,10aS)-7-Bromo-4-ethyl-1,2,3,4,10,10a-hexahydro-pyrazino[1,2-a]indole (4R,10aR)-7-Bromo-4-ethyl-1,2,3,4,10,10a-hexahydro-pyrazino[1,2-a]indole (100 mg, 0.36 mmol) was subjected to chromatographic separation using a Chiralcel® OD-H column and heptane/2-propanol 95:5 as the eluant. This yielded (4R,10aR)-7-bromo-4-ethyl-1,2,3,4,10,10a-hexahydro-pyrazino[1,2-a]indole (35 mg, 35%; colorless oil; m/e=281.1, 283.1 ([M+H]$^+$); $\alpha_D^{20}$: −16.5, $\alpha_{365}^{20}$: +92, and its enantiomer, (4S,10aS)-7-Bromo-4-ehtyl-1,2,3,4,10,10a-hexahydro-pyrazino[1,2-a]indole (30 mg, 30%, colorless oil, m/e=281.1, 283.1 ([M+H]$^+$); $\alpha_D^{20}$: +19.9, $\alpha_{365}^{20}$: −92).

Example 35

(4RS,10aSR)-4-Ethyl-1,2,3,4,10,10a-hexahydro-pyrazino[1,2-a]indole

The title compound, m/e=202.2 (M$^+$), was produced in accordance with the general method of example 25f) from (RS)-7-bromo-4-ethyl-3,4-dihydro-2H-pyrazino[1,2-a]indol1-one and separated from the isomeric (4RS,10aRS)-4-ethyl-1,2,3,4,10,10a-hexahydro-pyrazino[1,2-a]indole by chromatography on silica gel. Colorless gum.

Example 36

(4RS,10aRS)-4-Ethyl-1,2,3,4,10,10a-hexahydro-pyrazino[1,2-a]indole

The title compound, m/e=202.2 (M$^+$), was produced as described in example 35. Colorless gum.

Example 37

(4R,10aR)-8-Bromo-6-ethyl-4-methyl-1,2,3,4,10,10a-hexahydro-pyrazino[1,2-a]indole Bromine (0.2 M solution in acetic acid, 0.48 mL, 96 µmol) was added dropwise at room temperature to a solution of (4R,10aR)-6-ethyl-4-methyl-1,2,3,4,10,10a-hexahydro-pyrazino[1,2-a]indole (21 mg, 97 mol) and sodium acetate (8.0 mg, 97 µmol) in acetic acid (0.5 mL). After 30 min the reaction mixture was diluted with dichloromethane and extracted with 2 M aq. potassium hydroxide solution, dried (MgSO$_4$), and evaporated. Chromatography on SiO$_2$ (CH$_2$Cl$_2$/MeOH/NH$_4$OH 95:5:0.1) yielded the title compound (9 mg, 31%). Yellow oil. ISP-MS: m/e=295.3, 297.3 ([M+H]$^+$).

Example 38

(4R,10S,10aR)-4,6,10-Trimethyl-1,2,3,4,10,10a-hexahydro-pyrazino[1,2-a]indole a) (R)-4,6,10-Trimethyl-3,4-dihydro-2H-pyrazino[1,2-a]indol-1-one The title compound, m/e=229.2 ([M+H]$^+$), was produced in accordance with the general method of example 14d) from 3,7-dimethyl-1H-indole-2-carboxylic acid ethyl ester and (S)-5-methyl-2,2-dioxo-[1,2,3]oxathiazolidine-3-carboxylic acid tert-butyl ester. White solid.

b) (R)-4,6,10-Trimethyl-1,2,3,4-tetrahydro-pyrazino[1,2-a]indole oxalate (R)-4,6,10-Trimethyl-3,4-dihydro-2H-pyrazino[1,2-a]indol-1-one (200 mg, 0.88 mmol) was reacted with lithium aluminum hydride in accordance with the general method of example 15a). The crude material obtained was dissolved in ether (10 mL) and treated with oxalic acid solution (20% in ethanol, 7 mL). The precipitate was collected by filtration and dried to afford the title compound (196 mg, 74%). White solid. Anal. calc. for C$_{16}$H$_{20}$N$_2$O$_4$: C 63.14, H 6.62, N 9.20; found: C 62.86, H 6.87, N 8.92.

c) (4R,10S,10aR)-4,6,10-Trimethyl-1,2,3,4,10,10a-hexahydro-pyrazino[1,2-a]indole The title compound, m/e=216.2 (M$^+$), was produced in accordance with the general method of example 12e) from (R)-4,6,10-trimethyl-1,2,3,4-tetrahydro-pyrazino[1,2-a]indole oxalate and separated from the isomeric (4R,10R,10aR)-4,6,10-trimethyl-1,2,3,4,10,10a-hexahydro-pyrazino[1,2-a]indole by chromatography on silica gel. Colorless oil.

Example 39

(4R,10R,10aR)-4,6,10-Trimethyl-1,2,3,4,10,10a-hexahydro-pyrazino[1,2-a]indole The title compound, m/e=216.2 (M$^+$), was produced as described in example 38c). Colorless oil.

Examples 40 and 41

(4R,10aR)-8-Fluoro-4,7-dimethyl-1,2,3,4,10,10a-hexahydro-pyrazino[1,2-a]indole hydrochloride and

(4R,10aS)-8-Fluoro-4,7-dimethyl-1,2,3,4,10,10a-hexahydro-pyrazino[1,2-a]indole hydrochloride a) (Z)-2-Azido-3-(3-fluoro-4-methyl-phenyl)-acrylic acid ethyl ester To ethanol (200 ml) was added portionwise 6.7 g sodium metal in such a way that the temperature stayed below 50° C. After all sodium had dissolved, the temperature was brought to −5° C. and a solution of 3-fluoro-4-methylbenzaldehyde (10.0 g, 0.072 mol) and azido acetic acid ethyl ester (37.4 g, 0.29 mol) in 100 ml ethanol was added while maintaining the temperature below 5° C. After 3 h the orange-red solution was poured on saturated aqueous ammonium chloride solution and ethyl acetate (300 ml) and water (100 ml) was added. The phases were separated, the aqueous phase was reextracted three times with ethyl acetate (300 ml each) and the combined organic layers were washed with brine (400 ml) and dried over magnesium sulfate. The crude reaction product was purified by column chromatography over silical gel (0.030–0.063 mm) with n-hexane/tert-butyl methyl ether (50/1) as eluent to yield the title product as a yellow oil (9.8 g, 54.2%). EI-MS: m/e=249.1 (M)

b) 5-Fluoro-6-methyl-1H-indole-2-carboxylic acid ethyl ester (Z)-2-Azido-3-(3-fluoro-4-methyl-phenyl)-acrylic acid ethyl ester (9.7 g, 0.039 mol) was dissolved in 80 ml p-xylene and divided into four portions which were refluxed for 1 h. The oil bath was removed and the yellow solutions were cooled to 15° C. The resulting suspensions were filtered, washed with n-hexane and the solid material collected. The combined mother liquors were evaporated and the resulting oil was purified on silical gel (0.030–0.063 mm) with n-hexane/tert-butyl methyl ether (50/1) as eluent. The purified fractions together with the first precipitates were combined and chromatographed again to yield the desired product as a colorless solid (3.2 g, 37.2%). EI-MS: m/e=249.1 (M).

c) (R)-1-(2-tert-Butoxycarbonylamino-1-methyl-ethyl)-5-fluoro-6-methyl-1H-indole-2-carboxylic acid ethyl ester The title compound was produced in accordance with the general method of example 12b) from 5-fluoro-6-methyl-1H-indole-2-carboxylic acid ethyl ester and (S)-5-methyl-2,2-dioxo-[1,2,3]oxathiazolidine-3-carboxylic acid tert-butyl ester.

Leight beige solid. ISP-MS: m/e=379.4 (M+H$^+$).

d) (R)-8-Fluoro-4,7-dimethyl-3,4-dihydro-2H-pyrazino[1,2-a]indol-1-one

The title compound was produced in accordance with the general method of example 12c) from (R)-1-(2-tert-butoxycarbonylamino-1-methyl-ethyl)-5-fluoro-6-methyl-1H-indole-2-carboxylic acid ethyl ester.

Colorless solid. EI-MS: m/e=232.1 (M).

(e) 4R,10aR)-8-Fluoro-4,7-dimethyl-1,2,3,4,10,10a-hexahydro-pyrazino[1,2-a]indole hydrochloride and (4R,10aS)-8-Fluoro-4,7-dimethyl-1,2,3,4,10,10a-hexahydro-pyrazino[1,2-a]indole hydrochloride The title compounds were produced in accordance with the general method of example 25f) from (R)-8-fluoro-4,7-dimethyl-3,4-dihydro-2H-pyrazino[1,2-a]indol-1-one.

(4R,10aR) Isomer: Light brown solid. EI-MS: m/e 220.2 (M).

(4R,10aS) Isomer: Light brown solid. EI-MS: m/e=220.2 (M).

Examples 42 and 43

(4R,10aR)-6-Fluoro-4,7-dimethyl-1,2,3,4,10,10a-hexahydro-pyrazino[1,2-a]indole; hydrochloride and (4R,10aS)-6-Fluoro-4,7-dimethyl-1,2,3,4,10,10a-hexahydro-pyrazino[1,2-a]indole; hydrochloride a) 7-Fluoro-6-methyl-1H-indole-2-carboxylic acid ethyl ester This compound (2.4 g, 27.9%) was obtained in accordance to step b, Examples 41 and 42. Colorless solid. EI-MS: m/e=249.1 (M).

b) (R)-1-(2-tert-Butoxycarbonylamino-1-methyl-ethyl)-7-fluoro-6-methyl-1H-indole-2-carboxylic acid ethyl ester The title compound was produced in accordance with the general method of example 12b) from 7-fluoro-6-methyl-1H-indole-2-carboxylic acid ethyl ester and (S)-5-methyl-2,2-dioxo-[1,2,3]oxathiazolidine-3-carboxylic acid tert-butyl ester.

Leight beige solid. ISP-MS: m/e=379.4 (M+H$^+$).

c) (R)-6-Fluoro-4,7-dimethyl-3,4-dihydro-2H-pyrazino[1,2-a]indol-1-one

The title compound was produced in accordance with the general method of example 12c) from (R)-1-(2-tert-butoxycarbonylamino-1-methyl-ethyl)-7-fluoro-6-methyl-1H-indole-2-carboxylic acid ethyl ester.

Colorless solid. EI-MS: 232.1 (M).

d) (4R,10aR)-6-Fluoro-4,7-dimethyl-1,2,3,4,10,10a-hexahydro-pyrazino[1,2-a]indole hydrochloride and (4R,10aS)-6-Fluoro-4,7-dimethyl-1,2,3,4,10,10a-hexahydro-pyrazino[1,2-a]indole hydrochloride.

The title compounds were produced in accordance with the general method of example 25f) from (R)-6-fluoro-4,7-dimethyl-3,4-dihydro-2H-pyrazino[1,2-a]indol-1-one.

(4R,10aR) Isomer: Off-white solid. EI-MS: m/e=220.2 (M).

(4R,10aS) Isomer: Light brown solid. EI-MS: m/e=220.2 (M).

Example 44

(4R,10aR)-8-Fluoro-4-methyl-1,2,3,4,10,10a-hexahydro-pyrazino[1,2-a]indole hydrochloride a) (R)-1-(2-tert-Butoxycarbonylamino1-methyl-ethyl)-5-fluoro-1H-indole-2-carboxylic acid ethyl ester The title compound was produced in accordance with the general method of example 12b) from 5-fluoro-1H-indole-2-carboxylic acid ethyl ester and (S)-5-methyl-2,2-dioxo-[1,2,3]oxathiazolidine-3-carboxylic acid tert-butyl ester.

Colorless solid. ISP-MS: m/e=387.3 (M+Na$^+$).

b) (R)-8-Fluoro-4-methyl-3,4-dihydro-2H-pyrazino[1,2-a]indol-1-one

The title compound was produced in accordance with the general method of example 12c) from (R)-1-(2-tert-butoxycarbonylamino-1-methyl-ethyl)-5-fluoro-1H-indole-2-carboxylic acid ethyl ester.

Colorless solid. ISP-MS: m/e=219.2 (M+H$^+$).

c) (R)-8-Fluoro-4-methyl-1,2,3,4-tetrahydro-pyrazino[1,2-a]indole

The title compound was prepared in accordance with the general method of example 12d) from (R)-8-fluoro-4-methyl-3,4-dihydro-2H-pyrazino[1,2-a]indol-1-one.

Yellow oil. ISP-MS: m/e=205.2 (M+H$^+$).

d) (4R,10aR)-8-Fluoro-4-methyl-1,2,3,4,10,10a-hexahydro-pyrazino[1,2-a]indole hydrochloride The title compound was prepared in accordance with the general method of example 12e) from (R)-8-fluoro-4-methyl-1,2,3,4-tetrahydro-pyrazino[1,2-a]indole.

Brown solid. ISP-MS: m/e=207.2 (M+H$^+$).

Examples 45 and 46

(4R,10aR)-4,6-Dimethyl-1,2,3,4,10,10a-hexahydro-pyrazino[1,2-a]indole hydrochloride and (4R,10aS)-4,6-Dimethyl-1,2,3,4,10,10a-hexahydro-pyrazino[1,2-a]indole hydrochloride a) (R)-1-(2-tert-Butoxycarbonylamino-1-methyl-ethyl)-7-methyl-1H-indole-2-carboxylic acid ethyl ester The title compound was produced in accordance with the general method of example 12b) from 7-methyl-1H-indole-2-carboxylic acid ethyl ester and (S)-5-methyl-2,2-dioxo-[1,2,3]oxathiazolidine-3-carboxylic acid tert-butyl ester.

Colorless solid. ISP-MS: m/e=383.3 (M+Na$^+$).

b) (R)-4,6-Dimethyl-3,4-dihydro-2H-pyrazino[1,2-a]indol-1-one

The title compound was produced in accordance with the general method of example 12c) from (R)-1-(2-tert-butoxycarbonylamino-1-methyl-ethyl)-7-methyl-i H-indole-2-carboxylic acid ethyl ester.

Colorless powder. ISP-MS: m/e=215.3 (M+H$^+$).

c) (4R,10aR)-4,6-Dimethyl-1,2,3,4,10,10a-hexahydro-pyrazino[1,2-a]indole hydrochloride and (4R,10aS)-4,6-Dimethyl-1,2,3,4,10,10a-hexahydro-pyrazino[1,2-a]indole hydrochloride The title compounds were produced in accordance with the general method of example 25f) from (R)-4,6-dimethyl-3,4-dihydro-2H-pyrazino[1,2-a]indol-1-one.

(4R,10aR) Isomer: Light brown solid. ISP-MS: m/e=203.2 (M+H$^+$).

(4R,10aS) Isomer: Brown solid. ISP-MS: m/e=203.3 (M+H$^+$).

Example 47

(4R,10aR)-7-Bromo-9-fluoro-4-methyl-1,2,3,4,10,10a-hexahydro-pyrazino[1,2-a]indole hydrochloride a) 6-Bromo-4-fluoro-1H-indole-2-carboxylic acid ethyl ester The title compound was produced in accordance with the general method of examples 40 and 41, steps a and b), starting from 4-bromo-2-fluorobenzaldehyde and azido acetic acid ethyl ester. Colorless powder.

$^1$H-NMR (CDCl$_3$): δ [ppm]=1.35 (t, 3H), 4.36 (q, 2H), 7.15 (d, 1H), 7.17 (s, 1H), 7.47 (s, 1H), 12.4 (s, br, 1H).

b) (R)-6-Bromo-1-(2-tert-butoxycarbonylamino-1-methyl-ethyl)-4-fluoro-1H-indole-2-carboxylic acid ethyl ester The title compound was produced in accordance with the general method of example 12b) from 6-bromo-4-fluoro-1H-indole-2-carboxylic acid ethyl ester and (S)-5-methyl-2,2-dioxo-[1,2,3]oxathiazolidine-3-carboxylic acid tert-butyl ester.

Colorless solid. ISP-MS: m/e=465.0 and 467.2 (M+Na$^+$).

c) (R)-7-Bromo-9-fluoro-4-methyl-3,4-dihydro-2H-pyrazino[1,2-a]indol-1-one

The title compound was produced in accordance with the general method of example 12c) from (R)-6-bromo-1-(2-tert-butoxycarbonylamino-1-methyl-ethyl)-4-fluoro-1H-indole-2-carboxylic acid ethyl ester.

Colorless powder. ISP-MS: m/e=297.2 and 299.0 (M+H$^+$).

c) (R)-7-Bromo-9-fluoro-4-methyl-1,2,3,4-tetrahydro-pyrazino[1,2-a]indole

The title compound was produced in accordance with the general method of example 12d) from (R)-7-bromo-9-fluoro-4-methyl-3,4-dihydro-2H-pyrazino[1,2-a]indol-1-one.

Colorless solid. ISP-MS: m/e=283.0 and 285.0 (M+H$^+$).

c) (4R,10aR)-7-Bromo-9-fluoro-4-methyl-1,2,3,4,10,10a-hexahydro-pyrazino[1,2-a]indole hydrochloride The title compound was prepared in accordance with the general method of example 12e) from (R)-7-bromo-9-fluoro-4-methyl-1,2,3,4-tetrahydro-pyrazino[1,2-a]indole.

Light brown solid. ISP-MS: m/e=285.0 and 287.1 (M+H$^+$).

Example 48

(4R,10aR)-6-Fluoro-4-methyl-1,2,3,4,10,10a-hexahydro-pyrazino[1,2-a]indole a) (R)-1-(2-tert-Butoxycarbonylamino-1-methyl-ethyl)-7-fluoro-1H-indole-2-carboxylic acid ethyl ester The title compound was produced in accordance with the general method of example 12b) from 7-fluoro-1H-indole-2-carboxylic acid ethyl ester and (S)-5-methyl-2,2-dioxo-[1,2,3]oxathiazolidine-3-carboxylic acid tert-butyl ester.

Colorless powder. ISP-MS: m/e=387.3 (M+Na$^+$).

b) (R)-6-Fluoro-4-methyl-3,4-dihydro-2H-pyrazino[1,2-a]indol-1-one

The title compound was produced in accordance with the general method of example 12c) from (R)-1-(2-tert-butoxycarbonylamino-1-methyl-ethyl)-7-fluoro-1H-indole-2-carboxylic acid ethyl ester.

Colorless crystals. ISP-MS: m/e=219.2 (M+H$^+$).

c) (R)-6-Fluoro-4-methyl-1,2,3,4-tetrahydro-pyrazino[1,2-a]indole

The title compound was produced in accordance with the general method of example 12d) from (R)-6-fluoro-4-methyl-3,4-dihydro-2H-pyrazino[1,2-a]indol-1-one.

Yellow oil. ISP-MS: m/e=205.2 (M+H$^+$).

d) (4R,10aR)-6-Fluoro-4-methyl-1,2,3,4,10,10a-hexahydro-pyrazino[1,2-a]indole

The title compound was prepared in accordance with the general method of example 12e) from (R)-6-fluoro-4-methyl-1,2,3,4-tetrahydro-pyrazino[1,2-a]indole.

Light brown solid. ISP-MS: m/e=207.2 (M+H$^+$).

Example 49

(4R,10aR)-6,9-Difluoro-4-methyl-1,2,3,4,10,10a-hexahydro-pyrazino[1,2-a]indole; hydrochloride a) (R)-1-(2-tert-Butoxycarbonylamino-1-methyl-ethyl)-4,7-difluoro-1H-indole-2-carboxylic acid ethyl ester The title compound was produced in accordance with the general method of example 12b) from 4,7-difluoro-1H-indole-2-carboxylic acid ethyl ester and (S)-5-methyl-2,2-dioxo-[1,2,3]oxathiazolidine-3-carboxylic acid tert-butyl ester.

Colorless crystals. ISP-MS: m/e=383.3 (M+H$^+$).

b) (R)-6,9-Difluoro-4-methyl-3,4-dihydro-2H-pyrazino[1,2-a]indol-1-one

The title compound was produced in accordance with the general method of example 12c) from (R)-1-(2-tert-butoxycarbonylamino-1-methyl-ethyl)-4,7-difluoro-1H-indole-2-carboxylic acid ethyl ester.

Colorless powder. ISP-MS: m/e=237.1 (M+H$^+$).

c) (4R,10aR)-6,9-Difluoro-4-methyl-1,2,3,4,10,10a-hexahydro-pyrazino[1,2-a]indole hydrochloride The title compound was produced in accordance with the general method of example 25f) from (R)-6,9-difluoro-4-methyl-3,4-dihydro-2H-pyrazino[1,2-a]indol-1-one.

Light brown solid. ISP-MS: m/e=225.2 (M+H$^+$).

Examples 50 and 51

(4R,10aR)-7,9-Dichloro-4-methyl-1,2,3,4,10,10a-hexahydro-pyrazino[1,2-a]indole hydrochloride and (4R,10aS)-7,9-Dichloro-4-methyl-1,2,3,4,10,10a-hexahydro-pyrazino[1,2-a]indole hydrochloride a) (R)-1-(2-tert-Butoxycarbonylamino-1-methyl-ethyl)-4,6-dichloro-1H-indole-2-carboxylic acid ethyl ester The title compound was produced in accordance with the general method of example 12b) from 4,6-dichloro-1H-indole-2-carboxylic acid ethyl ester and (S)-5-methyl-2,2-dioxo-[1,2,3]oxathiazolidine-3-carboxylic acid tert-butyl ester.

Yellow solid. ISP-MS: m/e=415.3 (M+H$^+$).

b) (R)-7,9-Dichloro-4-methyl-3,4-dihydro-2H-pyrazino[1,2-a]indol-1-one

The title compound was produced in accordance with the general method of example 12c) from (R)-1-(2-tert-butoxycarbonylamino-1-methyl-ethyl)-4,6-dichloro-1H-indole-2-carboxylic acid ethyl ester.

Colorless powder. ISP-MS: m/e=269.2 (M+H$^+$).

c) (4R,10aR)-7,9-Dichloro-4-methyl-1,2,3,4,10,10a-hexahydro-pyrazino[1,2-a]indole hydrochloride and (4R,10aS)-7,9-Dichloro-4-methyl-1,2,3,4,10,10a-hexahydro-pyrazino[1,2-a]indole hydrochloride.

The title compounds were produced in accordance with the general method of example 25f) from (R)-7,9-dichloro-4-methyl-3,4-dihydro-2H-pyrazino[1,2-a]indol-1-one.

(4R,10aR) Isomer: Light yellow solid. ISP-MS: m/e=257.1 (M+H$^+$).

(4R,10aS) Isomer: Light brown solid. ISP-MS: m/e=257.1 (M+H$^+$).

Example 52

(4R,10aR)-4,7,9-Trimethyl-1,2,3,4,10,10a-hexahydro-pyrazino[1,2-a]indole a) (R)-1-(2-tert-Butoxycarbonylamino-1-methyl-ethyl)-4,6-dimethyl-1H-indole-2-carboxylic acid ethyl ester The title compound was produced in accordance with the general method of example 12b) from 4,6-dimethyl-1H-indole-2-carboxylic acid ethyl ester and (S)-5-methyl-2,2-dioxo-[1,2,3]oxathiazolidine-3-carboxylic acid tert-butyl ester.

Brown solid. ISP-MS: m/e=375.4 (M+H$^+$).

b) (R)-4,7,9-Trimethyl-3,4-dihydro-2H-pyrazino[1,2-a]indol-1-one

The title compound was produced in accordance with the general method of example 12c) from (R)-1-(2-tert-butoxycarbonylamino-1-methyl-ethyl)-4,6-dimethyl-1H-indole-2-carboxylic acid ethyl ester.

Colorless powder. EI-MS: m/e=228.3 (M).

c) (4R,10aR)-4,7,9-Trimethyl-1,2,3,4,10,10a-hexahydro-pyrazino[1,2-a]indole

The title compound was produced in accordance with the general method of example 25f) from (R)-4,7,9-trimethyl-3,4-dihydro-2H-pyrazino[1,2-a]indol-1-one.

Brown solid. ISP-MS: m/e=2117.3 (M+H$^+$).

Example 53

(4R,10aS)-6-Bromo-4-methyl-1,2,3,4,10,10a-hexahydro-pyrazino[1,2-a]indole hydrochloride a) (R)-7-Bromo-1-(2-tert-butoxycarbonylamino-1-methyl-ethyl)-1H-indole-2-carboxylic acid ethyl ester The title compound was produced in accordance with the general method of example 12b) from 7-bromo-1H-indole-2-carboxylic acid ethyl ester and (S)-5-methyl-2,2-dioxo-[1,2,3]oxathiazolidine-3-carboxylic acid tert-butyl ester.

Yellow oil. ISP-MS: m/e=425.3 and 427.3 (M+H$^+$).

b) (R)-6-Bromo-4-methyl-3,4-dihydro-2H-pyrazino[1,2-a]indol-1-one

The title compound was produced in accordance with the general method of example 12c) from (R)-7-bromo-1-(2-tert-butoxycarbonylamino-1-methyl-ethyl)-1H-indole-2-carboxylic acid ethyl ester.

Colorless crystals. ISP-MS: m/e=279.1 and 281.1 (M+H$^+$).

c) (R)-6-Bromo-4-methyl-1,2,3,4-tetrahydro-pyrazino[1,2-a]indole hydrochloride

The title compound was produced in accordance with the general method of example 12d) from (R)-6-bromo-4-methyl-3,4-dihydro-2H-pyrazino[1,2-a]indol-1-one.

Beige powder. EI-MS: m/e=264.1 and 266.1 (M).

d) (4R,10aS)-6-Bromo-4-methyl-1,2,3,4,10,10a-hexahydro-pyrazino[1,2-a]indole hydrochloride The title compound was produced in accordance with the general method of example 12e) from (R)-6-bromo-4-methyl-1,2,3,4-tetrahydro-pyrazino[1,2-a]indole hydrochloride.

Light brown solid. ISP-MS: m/e=267.2 and 269.2 (M+H$^+$).

Example 54

(4R,10aR)-7-Fluoro-4,6-dimethyl-1,2,3,4,10,10a-hexahydro-pyrazino[1,2-a]indole hydrochloride The title compound was prepared in accordance with the general method of example 12e) from (R)-7-fluoro-4,6-dimethyl-1,2,3,4-tetrahydro-2H-pyrazino[1,2-a]indole. Off-white solid, ISP MS: 221.3 (M+H)$^+$ a) 6-Fluoro-7-methyl-1H-indole-2-carboxylic acid ethyl ester 3-Fluoro-2-methyl-phenylhydrazine (8.4 g, 0.06 mol) was dissolved in ethanol and the solution cooled to 0° C. (ice-bath). Ethyl pyruvate (6.9ml, 0.062 mol) was added dropwise and the solution stirred 15 h at room temperature. The solvent was evaporated under reduced pressure, and the residue stirred with hexane. The mixture of hydrazones that formed upon cooling in an ice-bath was filtered and dried under vacuum. Yield: 9.1 g, 64%. The hydrazone mixture (7.6 g,0.032 mol) was dissolved in toluene (45 ml), anhydrous p-toluenesulfonic acid (8.2 g, 0.048 mol) added and the mixture heated 1 h at reflux. The mixture was cooled to room temperature, poured into half-saturated aqueous sodium hydrogen carbonate and extracted twice with ethyl acetate. The combined organic phases were washed with brine, dried over magnesium sulfate and evaporated. The residue was purified by column chromatography on silica gel (8:1 to 6:1 hexane/ethyl acetate eluant) to afford the product as a light brown solid (1.68 g, 24%). EI MS: 221.1 ($M^+$)

b) (R)-1-(2-tert-Butoxycarbonylamino-1-methyl-ethyl)-6-fluoro-7-methyl-1H-indole-2-carboxylic acid ethyl ester The title compound, ISP-MS: m/e=(M+H$^+$), was prepared in accordance with the general method of example 12b) from 6-fluoro7-methyl-1H-indole-2-carboxylic acid ethyl ester and (S)-5-methyl-2,2-dioxo-[1,2,3]oxathiazolidine-3-carboxylic acid tert-butyl ester. Yellow solid, ISP MS: 379.4 $(M+H)^+$ c) (R)-7-Fluoro-4,6-dimethyl-3,4-dihydro-2H-pyrazino[1,2-a]indol-1-one.

The title compound was prepared in accordance with the general method of example 12c) from (R)-1-(2-tert-butoxycarbonylamino-1-methyl-ethyl)-6-fluoro-7-methyl-1H-indole-2-carboxylic acid ethyl ester. White solid, ISP-MS: 233.1 $(M+H)^+$ d) (R)-7-Fluoro-4,6-dimethyl-1,2,3,4-tetrahydro-2H-pyrazino[1,2-a]indole The title compoundwas prepared in accordance with the general method of example 12d) from (R)-7-fluoro-4,6-dimethyl-3,4-dihydro-2H-pyrazino[1,2-a]indol-1-one. Off-white solid, EI-MS: 218.1 ($M^+$)

Example 55

(4R,10aS)-7-Chloro-4,8-dimethyl-1,2,3,4,10,10a-hexahydro-pyrazino[1,2-a]indole

The title compound, ISP-MS: m/e=237.2 ([M+H]$^+$), was produced in accordance with the general method of example 12e) from (R)-7-Chloro-4,8-dimethyl-1,2,3,4-tetrahydro-pyrazino[1,2-a]indole (see Example 56).

Example 56

(4R,10aR)-7-Chloro-4,8-dimethyl-1,2,3,4,10,10a-hexahydro-pyrazino[1,2-a]indole

The title compound, ISP-MS: m/e=237.2 ([M+H]$^+$), was produced in accordance with the general method of example 12e) from (R)-7-Chloro-4,8-dimethyl-1,2,3,4-tetrahydro-pyrazino[1,2-a]indole.

a) (R)-7-Chloro-4,8-dimethyl-1,2,3,4-tetrahydro-pyrazino [1,2-a]indole.

The title compound, ISP-MS: m/e=235.2 ([M+H]$^+$), was produced in accordance with the general method of example 12d) from (R)-7-chloro-4,8-dimethyl-3,4-dihydro-2H-pyrazino[1,2-a]indol-1-one. Yellow foam.

b) (R)-7-Chloro-4,8-dimethyl-3,4-dihydro-2H-pyrazino[1,2-a]indol-1-one.

The title compound (ISP-MS: m/e=249.2 ($M^+$+H)) was produced in accordance with the general method of example 14d) from 6-chloro-5-methyl-1H-indole-2-carboxylic acid ethyl ester and (S)-5-methyl-2,2-dioxo-[1,2,3]oxathiazolidine-3-carboxylic acid tert-butyl ester. Yield: 34%. Yellow solid.

Example 57

(4R,10aR)-4-Methyl-6-trifluoromethoxy-1,2,3,4,10,10a-hexahydro-pyrazino[1,2-a]indole The title compound, ISP-MS: m/e=273.2 ([M+H]$^+$), was produced in accordance with the general method of example 12e) from (R)-4-methyl-6-trifluoromethoxy-1,2,3,4-tetrahydro-pyrazino[1,2-a]indole.

a) (R)-4-Methyl-6-trifluoromethoxy-1,2,3,4-tetrahydro-pyrazino[1,2-a]indole

The title compound was produced in accordance with the general method of example 12d) from (R)-4-methyl-6-trifluoromethoxy-3,4-dihydro-2H-pyrazino[1,2-a]indol-1-one (light yellow solid, Mp: 58–60° C.; EI-MS: m/e=270.1 ($M^+$).

b) (R)-4-Methyl-6-trifluoromethoxy-3,4-dihydro-2H-pyrazino[1,2-a]indol-1-one

Sodium hydride (280mg of a 60% dispersion in mineral oil, 7 mmol) was added to a solution of 7-trifluoromethoxy-1H-indole-2-carboxylic acid ethyl ester (1.53 g, 5.6 mmol) and (S)-5-methyl-2,2-dioxo-[1,2,3]oxathiazolidine-3-carboxylic acid tert-butyl ester (1.53 g, 6.45 mmol) in N,N-dimethylformamide (15 mL) at 0° C. The solution was allowed to reach room temperature and stirred 36 h. Further amounts of sodium hydride (56 mg) and (S)-5-methyl-2,2-dioxo-[1,2,3]oxathiazolidine-3-carboxylic acid tert-butyl ester (306 mg) were added to complete the reaction. To the solution was added 10% aq. citric acid solution and the mixture stirred 1 h at room temperature. The organics were extracted with ethyl acetate (2×), the combined organic phases washed with sat. aq. NaHCO$_3$ solution and brine, dried (Na$_2$SO$_4$), and evaporated. The residue was dissolved in dichloromethane (25 mL), cooled to 0° C. and treated with trifluoroacetic acid (12 mL). After removal of the ice bath, the solution was stirred for 30 min and evaporated under reduced pressure. The residue was taken up in methanol (20 mL) and K$_2$CO$_3$ (2.52 g, 19.5 mmol) added, and the mixture stirred 15 h at room temperature. The mixture was filtered, the filtrate diluted with ethyl acetate, washed with water, dried (Na$_2$SO$_4$) and evaporated. The residue was purified by column chromatography on silica gel (hexane/ethyl acetate gradient) to afford the product as a pale yellow foam (89 mg, 64%). ISP-MS: m/e=285.1 ($M^+$+H).

c) 7-Trifluoromethoxy-1H-indole-2-carboxylic acid ethyl ester

The title compound (EI-MS: m/e=273.1 ($M^+$)) was produced in accordance with the general method of example 1c to 1e) from 7-trifluoromethoxy-1H-indole. Light brown amorphous solid.

d) 7-Trifluoromethoxy-1H-indole

Potassium hydroxide (17.9 g, 321 mmol) was boiled for 2 h in t-butanol (500 mL). (2-Trifluoromethoxy-6-trimethylsilanylethynyl-phenyl)-carbamic acid ethyl ester (52.8 g, 153 mmol) dissolved in t-butanol (500 mL) was added and boiling was continued for 2 h. The solvent was removed in vacuo and the residue was partitioned between diethyl ether and water. The organic phases were washed with brine, pooled and dried with $MgSO_4$. Evaporation of the solvent yielded 31.8 g of a brownish oil, which was purified by chromatography on silica gel with hexane/ethylacetate (9:1). This yielded the title compound, (30.2 g, 98%) as a yellow oil. (EI-MS: m/e=201.0 ($M^+$))

e) (2-Trifluoromethoxy-6-trimethylsilanylethynyl-phenyl)-carbamic acid ethyl ester Bis(triphenylphosphine)palladium(II) dichloride (1.1 g, 1.6 mmol) and copper(I) iodide (0.3 g, 1.6 mmol) were added to triethylamine (600 mL) and heated with stirring for 20 min. The mixture was cooled to room temperature and (2-iodo-6-trifluoromethoxy-phenyl)-carbamic acid ethyl ester (60.2 g, 160 mmol) was added. After stirring for 30 min at room temperature trimethylsilylacetylene (21.1 g, 152 mmol) was added and the mixture was stirred for another 2 h at room temperature. Triethylamine was removed in vacuo and the residue was partitioned between water and diethyl ether. The organic phases were washed with 1N HCl, brine, pooled and dried with $MgSO_4$. Evaporation of the solvent yielded 57 g of brownish solid, which was purified by chromatography on silica gel with hexane/ethyl acetate (9:1). This yielded the title compound, (52.8 g, 95%) as a beige amorphous solid. (EI-MS: m/e=345.0 ($M^+$))

f) (2-Iodo-6-trifluoromethoxy-phenyl)-carbamic acid ethyl ester (2-Trifluoromethoxy-phenyl)-carbamic acid ethyl ester (42.4 g, 0.17 mol) was dissolved in THF (800 mL) and cooled to −70° C. sec-BuLi in cyclohexane (280 mL, 1.3 M) was added dropwise at this temperature with stirring. Stirring was continued for 1 h after addition was complete. A solution of iodine (43.2 g, 0.17 mol) in THF (160 mL) was added dropwise at −70° C. Stirring was continued for 1 h after addition was complete and the mixture was hydrolysed with saturated ammonium chloride solution. Water was added and the mixture was extracted with diethyl ether. The organic phases were washed with 40% sodium bisulfite, water, brine, pooled and dried with $MgSO_4$. Evaporation of the solvent yielded the title compound, (60.2 g, 94%) as a colorless amorphous solid. (EI-MS: m/e=374.9 ($M^+$))

g) (2-Trifluoromethoxy-phenyl)-carbamic acid ethyl ester 2-(Trifluoromethoxy)aniline (50 g, 0.282 mol) was dissolved in DME (1000 mL) and cooled to −5° C. Sodium hydride (12.3 g, 55%, 0.282 mol) was added in portions and the suspension was allowed to warm to room temperature. Ethyl chloroformate (23.5 mL, 0.245 mol) was added drop by drop and the mixture was stirred for 2 h at room temperature and for 1.5 h at reflux after addition was complete. Hydrolysis was with water (110 mL). The phases were separated and the water phase was extracted with ethyl acetate. The organic phases were washed with brine, pooled and dried with $MgSO_4$. Evaporation of the solvent yielded 70.6 g of a brown oil, which was purified by chromatography on silica gel with hexane/ethyl acetate (6:1). This yielded the title compound, (44.2 g, 62%) as a beige yellow oil. (EI-MS: m/e=249.1 ($M^+$))

Example 58 and 59

(4R,10aR)-6-Fluoro-4,9-dimethyl-1,2,3,4,10,10a-hexahydro-pyrazino[1,2-a]indole hydrochloride and (4R,10aS)-6-Fluoro-4,9-dimethyl-1,2,3,4,10,10a-hexahydro-pyrazino[1,2-a]indole hydrochloride a) (2-Fluoro-5-methyl-phenyl)-hydrazine The title compound was prepared in accordance with the general method of example 25a) from 2-fluoro-5-methylaniline.

Light yellow solid. EI-MS: m/e=140.2 (M).

b) 2-[(2-Fluoro-5-methyl-phenyl)-hydrazono]-propionic acid ethyl ester

The title compound was prepared in accordance with the general method of example 25b) from (2-fluoro-5-methyl-phenyl)-hydrazine and ethyl pyruvate.

Light yellow solid. EI-MS: m/e=238.2 (M).

c) 7-Fluoro-4-methyl-1H-indole-2-carboxylic acid ethyl ester

The title compound was prepared in accordance with the general method of example 25c) from 2-[(2-fluoro-5-methyl-phenyl)-hydrazono]-propionic acid ethyl ester.

Light yellow solid. EI-MS: m/e=221.2 (M).

d) (R)-1-(2-tert-Butoxycarbonylamino-1-methyl-ethyl)-7-fluoro-4-methyl-1H-indole-2-carboxylic acid ethyl ester The title compound was prepared in accordance with the general method of example 12b) from 7-fluoro-4-methyl-1H-indole-2-carboxylic acid ethyl ester and (S)-5-methyl-2,2-dioxo-[1,2,3]oxathiazolidine-3-carboxylic acid tert-butyl ester.

Light yellow solid. ISP-MS: m/e=401.4 ($M+Na^+$).

e) (R)-6-Fluoro-4,9-dimethyl-3,4-dihydro-2H-pyrazino[1,2-a]indol1-one

The title compound was prepared in accordance with the general method of example 12c) from (R)-1-(2-tert-butoxycarbonylamino-1-methyl-ethyl)-7-fluoro-4-methyl-1H-indole-2-carboxylic acid ethyl ester.

Light yellow crystals. EI-MS: m/e=232.2 (M).

f) (4R,10aR)-6-Fluoro-4,9-dimethyl-1,2,3,4,10,10a-hexahydro-pyrazino[1,2-a]indole hydrochloride and (4R,10aS)-6-Fluoro-4,9-dimethyl-1,2,3,4,10,10a-hexahydro-pyrazino[1,2-a]indole hydrochloride The title compounds were prepared in accordance with the general method of example 25f) from (R)-6-fluoro-4,9-dimethyl-3,4-dihydro-2H-pyrazino[1,2-a]indol-1-one.

(4R,10aR) Isomer: Light yellow crystals. EI-MS: m/e=220.3 (M).

(4R,10aS) Isomer: White crystalline solid. EI-MS: m/e=220.3 (M).

Example 60

(4R,10aR)-4-Methyl-1,2,3,4,10,10a-hexahydro-pyrazino[1,2-a]indole-6-carbonitrile hydrochloride The title compound was produced in accordance with the general method of example 24a)-c) from (4R,10aR)-6-bromo-4-methyl-1,2,3,4,10,10a-hexahydro-pyrazino[1,2-a]indole.

Light yellow crystals. ISP-MS: m/e=214.3 ($M+H^+$).

Example 61 and 62

(4R,10aR)-6-Chloro-4,8-dimethyl-1,2,3,4,10,10a-hexahydro-pyrazino[1,2-a]indole hydrochloride and (4R,10aS)-6-Chloro-4,8-dimethyl-1,2,3,4,10,10a-hexahydro-pyrazino[1,2-a]indole hydrochloride a) (R)-1-(2-tert-Butoxycarbonylamino-1-methyl-ethyl)-7-chloro-5-methyl-1H-indole-2-carboxylic acid ethyl ester The title compound was prepared in accordance with the general method of example 12b) from 7-chloro-5-methyl-1H-indole-2-carboxylic acid ethyl ester and (S)-5-methyl-2,2-dioxo-[1,2,3]oxathiazolidine-3-carboxylic acid tert-butyl ester.

Colorless oil. EI-MS: m/e=394.3 (M).

b) (R)-6-Chloro-4,8-dimethyl-3,4-dihydro-2H-pyrazino[1,2-a]indol-1-one

The title compound was prepared in accordance with the general method of example 12c) from (R)-1-(2-tert-butoxycarbonylamino-1-methyl-ethyl)-7-chloro-5-methyl-1H-indole-2-carboxylic acid ethyl ester.

White crystalline solid. EI-MS: m/e=248.2 (M).

c) (4R,10aR)-6-Chloro-4,8-dimethyl-1,2,3,4,10,10a-hexahydro-pyrazino[1,2-a]indole hydrochloride and (4R,10aS)-6-Chloro-4,8-dimethyl-1,2,3,4,10,10a-hexahydro-pyrazino[1,2-a]indole hydrochloride The title compounds were prepared in accordance with the general method of example 25f) from (R)-6-chloro-4,8-dimethyl-3,4-dihydro-2H-pyrazino[1,2-a]indol-1-one.

(4R,10aR) Isomer: Light yellow crystals. ISP-MS: m/e=237.1 (M+H$^+$).

(4R,10aS) Isomer: White crystalline solid. ISP-MS: m/e=237.1 (M+H$^+$).

Example 63

(4R,10aR)-4,6,9-Trimethyl-1,2,3,4,10,10a-hexahydro-pyrazino[1,2-a]indole a) (R)-1-(2-tert-Butoxycarbonylamino-1-methyl-ethyl)-4,7-dimethyl-1H-indole-2-carboxylic acid ethyl ester The title compound was prepared in accordance with the general method of example 12b) from 4,7-dimethyl-1H-indole-2-carboxylic acid ethyl ester and (S)-5-methyl-2,2-dioxo-[1,2,3]oxathiazolidine-3-carboxylic acid tert-butyl ester.

b) (R)-4,6,9-Trimethyl-3,4-dihydro-2H-pyrazino[1,2-a]indol-1-one

The title compound was prepared in accordance with the general method of example 12c) from (R)-1-(2-tert-butoxycarbonylamino-1-methyl-ethyl)-4,7-dimethyl-1H-indole-2-carboxylic acid ethyl ester.

c) (R)-4,6,9-Trimethyl-1,2,3,4-tetrahydro-pyrazino[1,2-a]indole

The title compound was prepared in accordance with the general method of example 12d) from (R)-4,6,9-trimethyl-3,4-dihydro-2H-pyrazino[1,2-a]indol-1-one.

d) (4R,10aR)-4,6,9-Trimethyl-1,2,3,4,10,10a-hexahydro-pyrazino[1,2-a]indole

The title compound, ISP-MS: m/e=217.3 (M+H$^+$) and $\alpha_D^{20}$=−71.5, was prepared in accordance with the general method of example 12e) from (R)-4,6,9-trimethyl-1,2,3,4-tetrahydro-pyrazino[1,2-a]indole.

Example 64

(4R,10aS)-4,6,7-Trimethyl-1,2,3,4,10,10a-hexahydro-pyrazino[1,2-a]indole a) (4R,10aS)-4,6,7-Trimethyl-3,4,10,10a-tetrahydro-2H-pyrazino[1,2-a]indol-1one The title compound was prepared in accordance with the general method of example 14e) from (R)-4,6,7-trimethyl-3,4-dihydro-2H-pyrazino[1,2-a]indol-1-one.

b) (4R,10aS)-4,6,7-Trimethyl-1,2,3,4,10,10a-hexahydro-pyrazino[1,2-a]indole

The title compound, ISP-MS: m/e=217.3 (M+H$^+$), $\alpha_D^{20}$=−5.2, was prepared in accordance with the general method of example 14f)) from (4R,10aS)-4,6,7-trimethyl-3,4,10,10a-tetrahydro-2H-pyrazino[1,2-a]indol-1one.

Example 65

(4R,10aS)-4,6,9-Trimethyl-1,2,3,4,10,10a-hexahydro-pyrazino[1,2-a]indole a) (4R,10aS)-4,6,9-Trimethyl-3,4,10,10a-tetrahydro-2H-pyrazino[1,2-a]indol-1one The title compound was prepared in accordance with the general method of example 14e) from (R)-4,6,9-trimethyl-3,4-dihydro-2H-pyrazino[1,2-a]indol-1-one.

b) (4R,10aS)-4,6,9-Trimethyl-1,2,3,4,10,10a-hexahydro-pyrazino[1,2-a]indole

The title compound, ISP-MS: m/e=217.4 (M+H$^+$), $\alpha_D^{20}$=+57.4, was prepared in accordance with the general method of example 14f)) from (4R,10aS)-4,6,9-trimethyl-3,4,10,10a-tetrahydro-2H-pyrazino[1,2-a]indol-1one.

Example 66

(4R,10aR)-7-Chloro-4,6-dimethyl-1,2,3,4,10,10a-hexahydro-pyrazino[1,2-a]indole a) (3-Chloro-2-methyl-phenyl)-hydrazine The title compound was prepared in accordance with the general method of example 25a) from 3-chloro-2-methylaniline.

b) 2-[(3-Chloro-2-methyl-phenyl)-hydrazono]-propionic acid ethyl ester

The title compound was prepared in accordance with the general method of example 25b) from a) (3-chloro-2-methyl-phenyl)-hydrazine and ethyl pyruvate.

c) (R)-1-(2-tert-Butoxycarbonylamino-1-methyl-ethyl)-6-chloro-7-methyl-1H-indole-2-carboxylic acid ethyl ester The title compound was prepared in accordance with the general method of example 12b) from 6-chloro-7-methyl-1H-indole-2-carboxylic acid ethyl ester and (S)-5-methyl-2,2-dioxo-[1,2,3]oxathiazolidine-3-carboxylic acid tert-butyl ester.

d) (R)-7-Chloro-4,6-dimethyl-3,4-dihydro-2H-pyrazino[1,2-a]indol-1-one

The title compound was prepared in accordance with the general method of example 12c) from (R)-1-(2-tert-butoxycarbonylamino-1-methyl-ethyl)-6-chloro-7-methyl-1H-indole-2-carboxylic acid ethyl ester.

e) (R)-7-Chloro-4,6-dimethyl-1,2,3,4-tetrahydro-pyrazino[1,2-a]indole

The title compound was prepared in accordance with the general method of example 12d) from (R)-7-chloro-4,6-dimethyl-3,4-dihydro-2H-pyrazino[1,2-a]indol-1-one.

f) (4R,10aR)-7-Chloro-4,6-dimethyl-1,2,3,4,10,10a-hexahydro-pyrazino[1,2-a]indole The title compound, ISP-MS: m/e=237.2 (M+H$^+$), was prepared in accordance with the general method of example 12e) (R)-7-chloro-4,6-dimethyl-1,2,3,4-tetrahydro-pyrazino[1,2-a]indole.

Example 67

(4R,10aS)-7-Chloro-4,6-dimethyl-1,2,3,4,10,10a-hexahydro-pyrazino[1,2-a]indole a) (4R,10aS)-7-Chloro-4,6-dimethyl-3,4,10,10a-tetrahydro-2H-pyrazino[1,2-a]indol-1-one The title compound was prepared in accordance with the general method of example 14e) from (R)-7-chloro-4,6-dimethyl-3,4-dihydro-2H-pyrazino[1,2-a]indol-1-one.

b) (4R,10aS)-7-Chloro-4,6-dimethyl-1,2,3,4,10,10a-hexahydro-pyrazino[1,2-a]indole The title compound, ISP-MS: m/e=237.2 (M+H$^+$), $\alpha_D^{20}$=+32.6, was prepared in accordance with the general method of example 14f) (4R,10aS)-7-chloro-4,6-dimethyl-3,4,10,10a-tetrahydro-2H-pyrazino[1,2-a]indol-1-one.

Example 68

Mixture of (4S,10aS) and (4R,10aR)-7-Chloro-4-ethyl-1,2,3,4,10,10a-hexahydro-pyrazino[1,2-a]indole a) (RS)-7-Chloro-4-ethyl-3,4-dihydro-2H-pyrazino[1,2-a]indol-1-one The title compound, brownish solid with m.p. 153–155° C., was produced in accordance with the general method of example 14d) from 6-chloro-1H-indole-2-carboxylic acid ethyl ester and (RS)-5-ethyl-2,2-dioxo-[1,2,3]oxathiazolidine-3-carboxylic acid tert-butyl ester.

b) Mixture of (4RS,10aSR) and (4SR,10aRS)-7-chloro-4-ethyl-3,4,10,10a-tetrahydro-2H-pyrazino[1,2-a]indol-1-one The title compound was prepared in accordance with the general method of example 14e) from a) (RS)-7-chloro-4-ethyl-3,4-dihydro-2H-pyrazino[1,2-a]indol-1-one.

c) Mixture of (4S,10aS) and (4R,10aR)-7-chloro-4-ethyl-1,2,3,4,10,10a-hexahydro-pyrazino[1,2-a]indole The title compound, ISP-MS: m/e=237.2 (M+H$^+$), was prepared in accordance with the general method of example 14f) from the mixture of (4RS,10aSR) and (4SR,10aRS)-7-chloro-4-ethyl-3,4,10,10a-tetrahydro-2H-pyrazino[1,2-a]indol-1-one and separated from the epimeric mixture by flash chromatography with dichloromethane/methanol (93:7).

Example 69

Mixture of (4S,10aR) and (4R,10aS)-7-chloro-4-ethyl-1,2,3,4,10,10a-hexahydro-pyrazino[1,2-a]indole The title compound, ISP-MS: m/e=237.2 (M+H$^+$), was prepared in accordance with the general method of example 14f) from the mixture of (4RS,10aSR) and (4SR,10aRS)-7-chloro-4-ethyl-3,4,10,10a-tetrahydro-2H-pyrazino[1,2-a]indol-1-one and separated from the epimeric mixture by flash chromatography with dichloromethane/methanol (93:7).

Example 70

(4R,10aR)-7-Chloro-4-ethyl-1,2,3,4,10,10a-hexahydro-pyrazino[1,2-a]indole a) (R)-7-Chloro-4-ethyl-3,4-dihydro-2H-pyrazino[1,2-a]indol-1-one The title compound was isolated from the racemate, (RS)-7-chloro-4-ethyl-3,4-dihydro-2H-pyrazino[1,2-a]indol-1-one, by chiral HPLC on a ChiralPak AD column; light brown solid with m.p. 162–165° C.

b) (4R,10aR)-7-Chloro-4-ethyl-3,4,10,10a-tetrahydro-2H-pyrazino[1,2-a]indol-1-one and (4R,10aS)-7-chloro-4-ethyl-3,4,10,10a-tetrahydro-2H-pyrazino[1,2-a]indol-1-one The tide compounds were prepared as a mixture in accordance with the general method of example 14e) from (R)-7-chloro-4-ethyl-3,4-dihydro-2H-pyrazino[1,2-a]indol-1-one.

c) (4R,10aR)-7-Chloro-4-ethyl-1,2,3,4,10,10a-hexahydro-pyrazino[1,2-a]indole

The title compound, EI-MS: m/e=236.1 (M$^+$) and $\alpha_D^{20}$=−29.9, was prepared in accordance with the general method of example 14f) from the above mixture and separated from its epimer by flash chromatography with dichloromethane/methanol (93:7).

Example 71

(4R,10aS)-7-Chloro-4-ethyl-1,2,3,4,10,10a-hexahydro-pyrazino[1,2-a]indole

The title compound, EI-MS: m/e=236.1 (M$^+$) and $\alpha_D^{20}$=−80.6, was prepared in accordance with the general method of example 14f) from the mixture obtained in example 70b) and separated from its epimer by flash chromatography with dichloromethane/methanol (93:7).

Example 72

(4S,10aS)-7-Chloro-4-ethyl-1,2,3,4,10,10a-hexahydro-pyrazino[1,2-a]indole a) (S)-7-Chloro-4-ethyl-3,4-dihydro-2H-pyrazino[1,2-a]indol-1-one The title compound was isolated from the racemate, (RS)-7-chloro-4-ethyl-3,4-dihydro-2H-pyrazino[1,2-a]indol-1-one, by chiral HPLC on a ChiralPak AD column; yellow solid with m.p. 169–171° C.

b) (4S,10aR)-7-Chloro-4-ethyl-3,4,10,10a-tetrahydro-2H-pyrazino[1,2-a]indol-1-one and (4S,10aS)-7-chloro-4-ethyl-3,4,10,10a-tetrahydro-2H-pyrazino[1,2-a]indol-1-one The title compounds were prepared as a mixture in accordance with the general method of example 14e) from (S)-7-chloro-4-ethyl-3,4-dihydro-2H-pyrazino[1,2-a]indol-1-one.

c) (4S,10aS)-7-Chloro-4-ethyl-1,2,3,4,10,10a-hexahydro-pyrazino[1,2-a]indole

The title compound, ISP-MS: m/e=237.2 (M+H$^+$) and $\alpha_D^{20}$=+28.2, was prepared in accordance with the general method of example 14f) from the above mixture and separated from its epimer by flash chromatography with dichloromethane/methanol (93:7).

Example 73

(4S,10aR)-7-Chloro-4-ethyl-1,2,3,4,10,10a-hexahydro-pyrazino (1,2-a]indole

The title compound, ISP-MS: m/e=37.2 (M+H$^+$) and $\alpha_D^{20}$=+40.6, was prepared in accordance with the general method of example 14f) from the mixture obtained in example 72b) and separated from its epimer by flash chromatography with dichloromethane/methanol (93:7).

Example 74

(4R,10aS)-6-Chloro-4,7-dimethyl-1,2,3,4,10,10a-hexahydro-pyrazino[1,2-a]indole a) (4R,10aS)-6-Chloro-4,7-dimethyl-3,4,10,10a-tetrahydro-2H-pyrazino[1,2-a]indol-1-one The title compound was prepared in accordance with the general method of example 14e) from (R)-6-chloro-4,7-dimethyl-3,4-dihydro-2H-pyrazino[1,2-a]indol-1-one.

b) (4R,10aS)-6-Chloro-4,7-dimethyl-1,2,3,4,10,10a-hexahydro-pyrazino[1,2-a]indole The title compound, EI-MS: m/e=236.1 (M$^+$), $\alpha_D^{20}$=−52.6, was prepared in accordance with the general method of example 14f) from (4R,10aS)-6-chloro-4,7-dimethyl-3,4,10,10a-tetrahydro-2H-pyrazino[1,2-a]indol-1-one.

Example 75

(4R,10aR)-6-Chloro-4,7-dimethyl-1,2,3,4,10,10a-hexahydro-pyrazino[1,2-a]indole a) (2-Chloro-3-methyl-phenyl)-hydrazine The title compound was prepared in accordance with the general method of example 25a) from 2-chloro-3-methylaniline.

b) 2-[(2-Chloro-3-methyl-phenyl)-hydrazono]-propionic acid ethyl ester

The title compound was prepared in accordance with the general method of example 25b) from (2-Chloro-3-methyl-phenyl)-hydrazine and ethyl pyruvate.

c) 7-Chloro-6-methyl-1H-indole-2-carboxylic acid ethyl ester

The title compound was prepared in accordance with the general method of example 25c) from 2-[(2-chloro-3-methyl-phenyl)-hydrazono]-propionic acid ethyl ester.

d) (R)-1-(2-tert-Butoxycarbonylamino-1-methyl-ethyl)-7-chloro-6-methyl-1H-indole-2-carboxylic acid ethyl ester The title compound was prepared in accordance with the general method of example 12b) from 7-chloro-6-methyl-1H-indole-2-carboxylic acid ethyl ester and (S)-5-methyl-2,2-dioxo-[1,2,3]oxathiazolidine-3-carboxylic acid tert-butyl ester.

e) (R)-6-Chloro-4,7-dimethyl-3,4-dihydro-2H-pyrazino[1,2-a]indol-1-one

The title compound was prepared in accordance with the general method of example 12c) from (R)-1-(2-tert-butoxycarbonylamino-1-methyl-ethyl)-7-chloro-6-methyl-1H-indole-2-carboxylic acid ethyl ester.

f) (R)-6-Chloro-4,7-dimethyl-1,2,3,4-tetrahydro-pyrazino[1,2-a]indole

The title compound was prepared in accordance with the general method of example 12d) from (R)-6-chloro-4,7-dimethyl-3,4-dihydro-2H-pyrazino[1,2-a]indol-1-one.

g) (4R,10aR)-6-Chloro-4,7-dimethyl-1,2,3,4,10,10a-hexahydro-pyrazino[1,2-a]indole The title compound, ISP-MS: m/e=237.2 (M+H$^+$) and $\alpha_D^{20}$=−111.6, was prepared in accordance with the general method of example 12e) from (R)-6-chloro-4,7-dimethyl-3,4-dihydro-2H-pyrazino[1,2-a]indol-1-one.

Example 76

(10R,6aS)-10-Methyl-2,3,6,6a,7,8,9,10-octahydro-1H-8,10a-diaza-cyclopenta[c]fluorene hydrochloride a) 2-[((2,3-Dihydro-1H-inden-4-yl)-hydrazono]-propionic acid ethyl ester The title compound, ISP-MS: m/e=247.3 (M+H$^+$), was prepared in accordance with the general method of example 25b) from (2,3-hihydro-1H-inden-4-yl)-hydrazine and ethyl pyruvate.

b) 1,6,7,8-Tetrahydro-1-aza-as-indacene-2-carboxylic acid ethyl ester

The title compound, EI-MS: m/e=229.1 (M$^+$), was prepared in accordance with the general method of example 25c) from 2-[((2,3-dihydro-1H-inden-4-yl)-hydrazono]-propionic acid ethyl ester.

c) (R)-1-(2-tert-Butoxycarbonylamino-1-methyl-ethyl)-1,6,7,8-tetrahydro-1-aza-as-indacene-2-carboxylic acid ethyl ester The title compound was prepared in accordance with the general method of example 12b) from b) 1,6,7,8-tetrahydro-1-aza-as-indacene-2-carboxylic acid ethyl ester and (S)-5-methyl-2,2-dioxo-[1,2,3]oxathiazolidine-3-carboxylic acid tert-butyl ester.

d) (R)-10-Methyl-2,3,9,10-tetrahydro-1H,8H-8,10a-diaza-cyclopenta[c]fluoren-7-one The title compound, EI-MS: m/e=240.2 (M$^+$), was prepared in accordance with the general method of example 12c) from (R)-1-(2-tert-butoxycarbonylamino-1-methyl-ethyl)-1,6,7,8-tetrahydro-1-aza-as-indacene-2-carboxylic acid ethyl ester.

e) (4R,10aS)-10-Methyl-2,3,6,6a,9,10-hexahydro-1H,8H-8,10a-diaza-cyclopenta[c]fluoren-7-one The title compound was prepared in accordance with the general method of example 14e) from (R)-10-methyl-2,3,9,10-tetrahydro-1H,8H-8,10a-diaza-cyclopenta[c]fluoren-7-one.

f) (4R,10aS)-10-Methyl-2,3,6,6a,7,8,9,10-octahydro-1H,8,10a-diaza-cyclopenta[c]fluorene hydrochloride The title compound, ISP-MS: m/e=229.2 (M+H$^+$), $\alpha_D^{20}$=−67.8, was prepared in accordance with the general method of example 14f) from (4R,10aS)-10-methyl-2,3,6,6a,9,10-hexahydro-1H,8H-8,10a-diaza-cyclopenta[c]fluoren-7-one.

Example 77

(4R,10aR)-N-(4-Methyl-1,2,3,4,10,10a-hexahydropyrazino[1,2-a]indol-7-yl)-acetamide; hydrochloride a) (4R,10aR)-7-(Benzhydrylidene-amino)-4-methyl-3,4,10,10a-tetrahydro-1H-pyrazino[1,2-a]indole-2-carboxylic acid tert-butyl ester A mixture of (4R,10aR)-7-bromo-4-methyl-3,4,10,10a-tetrahydro-1H-pyrazino[1,2-a]indole-2-carboxylic acid tert-butyl ester (3.0 g, 8 mmol), benzophenone imine (1.52 g, 8 mmol), tris(dibenzylideneacetone)dipalladium chloroform complex (85 mg, 0.08 mmol), 2,2'-bis(diphenylphosphino)-1,1'-binaphtalene (153 mg, 0.24 mmol) and sodium tert-butylate (1.1 g, 11.4 mmol) in toluene (30 mL) was heated to 80° C. for 3 h. After cooling the mixture was diluted with diethyl ether (300 mL) and filtered through Celite®. The solvents were evaporated and the residue was purified by chromatography on silica gel with ethylacetate/n-hexane (1:4). The title product was isolated as yellowish foam (3.4 g, 89%); ISP-MS: m/e=468.3 (M+H$^+$).

b) (4R,10aR)-7-Amino-4-methyl-3,4,10,10a-tetrahydro-1H-pyrazino[1,2-a]indole-2-carboxylic acid tert-butyl ester A mixture of (4R,10aR)-7-(benzhydrylidene-amino)-4-methyl-3,4,10,10a-tetrahydro-1H-pyrazino[1,2-a]indole-2-carboxylic acid tert-butyl ester (3.35 g, 7.2 mmol), ammonium formiate (6.8 g, 107 mmol) and palladium on carbon (1.5 g, 5%) in methanol (35 mL) was heated to 60° C. for 1 h. After cooling the mixture was diluted with dichloromethane (100 mL) and filtered. The filtrate was washed with water (100 mL), the water phase was extracted with dichloromethane, and organic phases were pooled and dried with MgSO$_4$. The solvents were removed in vacuo and the residue was purified by chromatography on silica gel with ethylacetate/n-hexane (1:1). The title product was isolated as yellow foam (1.15 g, 53%); ISP-MS: m/e=304.4 (M+H$^+$).

c) (4R,10aR)-N-(4-Methyl-1,2,3,4,10,10a-hexahydro-pyrazino[1,2-a]indol-7-yl)-acetamide; hydrochloride A mixture of (4R,10aR)-7-amino-4-methyl-3,4,10,10a-tetrahydro-1H-pyrazino[1,2-a]indole-2-carboxylic acid tert-butyl ester (300 mg, 1 mmol), triethylamine (0.3 mL, 2.2 mmol) and acetyl chloride (0.07 mL, 1 mmol) in dichloromethane (6 mL) was stirred for 30 min. The solvent was removed in vacuo and the residue was purified by chromatography on silica gel with ethylacetate/n-hexane (1:1) to yield 230 mg of the Boc-protected acetamide. This was then deprotected by stirring for 1 h in trifluoroacetic acid (2 mL) at room temperature. Saturated sodium bicarbonate solution (40 mL) was added and the mixture was extracted with dichloromethane. Organic phases were pooled, dried with MgSO$_4$, the solvent was removed in vacuo and the residue was purified by chromatography on silica gel with dichloromethane/methanol (9:1). The title product was isolated and precipitated as hydrochloride salt from ethylacetate. Beige solid (97 mg, 35%); m.p.>250 ° C. dec., EI-MS: m/e=245.3 (M$^+$).

Example 78

(4R,10aR)-(4-Methyl-1,2,3,4,10,10a-hexahydropyrazino[1,2-a]indol-7-yl)-methanol; hydrochloride a) (4R,10aR)-4-Methyl-3,4,10,10a-tetrahydro-1H-pyrazino[1,2-a]indole-2,7-dicarboxylic acid 2-tert-butyl ester (4R,10aR)-7-Bromo-4-methyl-3,4,10,10a-tetrahydro-1H-pyrazino[1,2-a]indole-2-carboxylic acid tert-butyl ester (5.4 g, 15 mmol) was dissolved in tetrahydrofuran (90 mL) and cooled to −78° C. n-Butyllithium (12.8 mL, 1.6 N in n-hexane) was added slowly and the yellow mixture was stirred for another 30 min at −78° C. after addition was finished. Carbon dioxide gas was bubbled through the mixture for 30 min, cooling was removed and the mixture was hydrolyzed by adding it to a mixture of ice and water (200 g). 1 N Sodium hydroxide solution (250 mL) was added and the mixture washed with diethylether (100 mL). The organic phase was extracted twice with 1 N sodium hydroxide solution; the water phases were pooled and acidified to pH 1.7 with 1 N hydrochloric acid. The water phase was extracted with diethylether (3×300 mL), organic phases were pooled and dried with MgSO$_4$. The solvent was evaporated and the residue was triturated with diethylether/n-hexane (1:3). The title product was isolated as colorless solid (4.1 g, 85%); ISN-MS: m/e=331.3 (M$^-$); $\alpha_D^{20}$=−42.8.

b) (4R,10aR)-7-Hydroxymethyl-4-methyl-3,4,10,10a-tetrahydro-1H-pyrazino[1,2-a]indole-2-carboxylic acid tert-butyl ester (4R,10aR)-4-Methyl-3,4,10,10a-tetrahydro-1H-pyrazino[1,2-a]indole-2,7-dicarboxyl acid 2-tert-butyl ester (250 mg, 0.75 mmol) was dissolved in tetrahydrofuran (5 mL). Lithium aluminium hydride (75 mg, 1.5 mmol) was added in portions and the mixture was stirred for 15 min at room temperature. Water (0.2 mL), sodium hydroxide solution (0.4 mL, 15%) and water (0.6 mL) were added sequentially, the mixture was diluted with diethylether (15 mL) and dried with Na$_2$SO$_4$. The solvents were removed in vacuo and the residue was purified by chromatography on silica gel with ethylacetate/n-hexane (2:1). The title product was isolated as light yellow oil (163 mg, 68%); ISP-MS: m/e=319.4 (M+H$^+$).

c) (4R,10aR)-(4-Methyl-1,2,3,4,10,10a-hexahydro-pyrazino[1,2-a]indol-7-yl)-methanol; hydrochloride A mixture of (4R,10aR)-7-hydroxymethyl-4-methyl-3,4,10,10a-tetrahydro-1H-pyrazino[1,2-a]indole-2-carboxylic acid tert-butyl ester (160 mg, 0.5 mmol), trifluoroacetic acid (2 mL) and dichloromethane (3 mL) was stirred for 1 h at room temperature. Saturated sodium bicarbonate solution (50 mL) was added and the mixture was extracted with dichloromethane. Organic phases were pooled, dried with Na$_2$SO$_4$, the solvent was removed in vacuo and the residue was precipitated as hydrochloride salt from ethylacetate to yield the title compound. Beige solid (84 mg, 65%); m.p. 66 ° C. dec., ISP-MS: m/e=219.3 (M+H$^+$).

Example 79

(4R,10aR)-4-Methyl-1,2,3,4,10,10a-hexahydropyrazino[1,2-a]indole-7-carboxylic acid butylamide; hydrochloride a) (4R,10aR)-7-Butylcarbamoyl-4-methyl-3,4,10,10a-tetrahydro-1H-pyrazino[1,2-a]indole-2-carboxylic acid tert-butyl ester (4R,10aR)-4-Methyl-3,4,10,10a-tetrahydro-1H-pyrazino[1,2-a]indole-2,7-dicarboxylic acid 2-tert-butyl ester (300 mg, 0.9 mmol) was dissolved in dichloromethane (5 mL). N-Butylamine (0.45 mL, 4.5 mmol), 4-ethylmorpholine (0.57 mL, 4.5 mmol) and BOP (0.42 g, 0.95 mmol) was added and the mixture was stirred for 16 h at room temperature. The mixture was added to 1 N hydrochloric acid (20 mL) and extracted with diethylether (2×50 mL). Organic phases were pooled, washed with water, 2 N sodium bicarbonate, water and brine to be finally dried with $MgSO_4$. The solvents were removed in vacuo to yield the title compound as colorless foam (346 mg, 98%); ISP-MS: m/e=332.3 (M+H$^+$).

b)  (4R,10aR)-(4-Methyl-1,2,3,4,10,10a-hexahydro-pyrazino[1,2-a]indol-7-yl)-methanol; hydrochloride This compound was prepared in accordance with the general method of example 78c) from (4R,10aR)-7-butyl-carbamoyl-4-methyl-3,4,10,10a-tetrahydro-1H-pyrazino[1,2-a]indole-2-carboxylic acid tert-butyl ester. White solid. M.p. 125° C. dec.; ISP-MS: m/e=288.3 (M+H$^+$); $\alpha_D^{20}$=−43.0.

Example 80

(4R,10aR)-4,8-Dimethyl-1,2,3,4,10,10a-hexahydro-pyrazino[1,2-a]indole trifluoroacetate a)  (R)-1-(2-tert-Butoxycarbonylamino-1-methyl-ethyl)-5-methyl-1H-indole-2-carboxylic acid ethyl ester The title compound was prepared in accordance with the general method of example 12b) from 5-methyl-1H-indole-2-carboxylic acid ethyl ester and (S)-5-methyl-2,2-dioxo-[1,2,3]oxathiazolidine-3-carboxylic acid tert-butyl ester.

b)  (R)-4,8-Dimethyl-3,4-dihydro-2H-pyrazino[1,2-a]indol-1-one

The title compound was prepared in accordance with the general method of example 12c) from (R)-1-(2-tert-butoxycarbonylamino-1-methyl-ethyl)-5-methyl-1H-indole-2-carboxylic acid ethyl ester.

c)  (R)-4,8-Dimethyl-1,2,3,4-tetrahydro-pyrazino[1,2-a]indole

The title compound was prepared in accordance with the general method of example 12d) from (R)-4,8-dimethyl-3,4-dihydro-2H-pyrazino[1,2-a]indol-1-one.

d)  (4R,10aR)-4,8-Dimethyl-1,2,3,4,10,10a-hexahydro-pyrazino[1,2-a]indole trifluoroacetate The title compound, ISP-MS: m/e=203.2 (M+H$^+$) and $\alpha_D^{20}$=−48.5, was prepared in accordance with the general method of example 12e) from (R)-4,8-dimethyl-1,2,3,4-tetrahydro-pyrazino[1,2-a]indole.

Examples 81 and 82

(4R,10a R)-8-Bromo-4,7-dimethyl-1,2,3,4,10,10a-hexahydro-pyrazino[1,2-a]indole and (4R,10a S)-8-Bromo-4,7-dimethyl-1,2,3,4,10,10a-hexahydro-pyrazino[1,2-a]indole a) (4-Bromo-3-methyl-phenyl)-carbamic acid methyl ester To a solution of 10.00 g 4-bromo-3-methylaniline in 50 ml dichloromethane was added 80 ml of a 10% solution of sodium bicarbonate in water. The mixture was cooled to 0° C. and 6.2 ml (7.62 g) methyl chloroformate was added during 10 min. with stirring. The reaction mixture was stirred at room temperature for 1 h. The phases were separated. The organic phase was washed with a 10% solution of citric acid in water, 10% solution of sodium bicarbonate in water and brine, dried with magnesium sulfate and evaporated to yield 12.94 g of (4-bromo-3-methyl-phenyl)-carbamic acid methyl ester as light brown solid melting at 71–72° C.

b)  (4-Bromo-2-iodo-5-methyl-phenyl)-carbamic acid methyl ester

To a solution of 5.00 g (4-bromo-3-methyl-phenyl)-carbamic acid methyl ester in 50 ml acetonitrile were added at 0° C. 4.84 g N-iodosuccinimide and 0.18-ml trifluoromethanesulfonic acid. The mixture was stirred 18 h at room temperature. The solid was collected by filtration, washed with cold acetonitrile and dried to constant weight to yield 5.80 g (4-bromo-2-iodo-5-methyl-phenyl)-carbamic acid methyl ester as white crystals melting at 140–141° C.

c)  (4-Bromo-2-{3-[dimethyl-(1,1,2-trimethyl-propyl)-silanyloxy]-prop-1-ynyl}-5-methyl-phenyl)-carbamic acid methyl ester To a solution of 3.70 g (4-bromo-2-iodo-5-methyl-phenyl)-carbamic acid methyl ester and 0.070 g bis-triphenylphosphine palladium dichloride and 0.038 g cuprous iodide in 25 ml triethylamine was added 2.38 g dimethyl (2-propynyloxy)(1,1,2-trimethylpropyl)-silane and the mixture was heated 2 h at reflux. The reaction mixture was partitioned between water and ethyl acetate. The phases were separated and the organic phase was washed with 1N hydrochloric acid, sodium bicarbonate and brine, dried with magnesium sulfate and purified by chromatography on silica gel with hexane:ethyl acetate=4:1 to yield 1.92 g (4-bromo-2-{3-[dimethyl-(1,1,2-trimethyl-propyl)-silanyloxy]-prop-1-ynyl}-5-methyl-phenyl)-carbamic acid methyl ester as a light brown oil. MS: M+NH$_4^+$=457.0 M+Na$^+$=462.2 d)  5-Bromo-2-[dimethyl-(1,1,2-trimethyl-propyl)-silanyloxymethyl]-6-methyl-1H-indole To a suspension of 0.5144 g lithium hydroxide in 37 ml dimethylsulfoxide and 3.7 ml water was added 1.800 g (4-bromo-2-{3-[dimethyl-(1,1,2-trimethyl-propyl)-silanyloxy]-prop1-ynyl}-5-methyl-phenyl)-carbamic acid methyl ester and the mixture was heated 2 h at 80° C. Water and ethyl acetate were added. The pH was adjusted to 6.00 by addition of hydrochloric acid. The phases were separated and the organic phase was washed with 10% sodium bicarbonate and brine and purified by chromatography on silica gel with hexane:ethyl acetate=9:1 to yield 0.97 g 5-bromo-2-[dimethyl-(1,1,2-trimethyl-propyl)-silanyloxymethyl]-6-methyl-1H-indole as a colorless oil. EI-MS: M=383.1 e)  (R)-(2-{5-Bromo-2-[dimethyl-(1,1,2-trimethyl-propyl)-silanyloxymethyl]-6-methyl-indol-1-yl}-propyl)-carbamic acid tert-butyl ester To a solution of 0.95 g 5-bromo-2-[dimethyl-(1,1,2-trimethyl-propyl)-silanyloxymethyl]-6-methyl-1H-indole in 10 ml N,N-dimethylformamide was added 0.143 g sodium hydride 55–65% in oil and the mixture was stirred 30 min at room temperature. To the resulting mixture was added (S)-5-methyl-2,2-dioxo-[1,2,3]oxathiazolidine-3-carboxylic acid tert-butyl ester (0.703 g) and the mixture was stirred 2 h at room temperature. The reaction mixture was partitioned between water and ethyl acetate. The phases were separated and the organic phase was washed with 10% citric acid and brine, dried over magnesium sulfate and purified by chromatography on silica gel with hexane:ethyl acetate=5:1 to yield 0.789 g (R)-(2-{5-bromo-2-[dimethyl-(1,1,2-trimethyl-propyl)-silanyloxymethyl]-6-methyl-indol-1-yl}-propyl)-carbamic acid tert-butyl ester as a slightly yellow oil. ISP-MS: M+H=541.3 f) (R)-8-Bromo-4,7-dimethyl-1,2,3,4-tetrahydro-pyrazino[1,2-a]indole-2-carboxylic acid tert-butyl ester A mixture of 0.75 g (R)-(2-{5-bromo-2-[dimethyl-(1,1,2-trimethyl-propyl)-silanyloxymethyl]-6-methyl-indol-1-yl}-propyl)-carbamic acid tert-butyl ester and 0.52 g ammonium fluoride in 7.5 ml methanol was stirred 18 h at room temperature. The reaction mixture was partitioned between water and ethyl acetate. The phases were separated and the organic phase was washed with 10% citric acid, 10% sodium bicarbonate and brine, dried over magnesium sulfate and evaporated to dryness. The residue was taken up in 6 ml dichloromethane and 0.59 g manganese dioxide was added. The mixture was stirred 2 h at room temperature. The solids were removed by filtration over dicalite and the filtrate was evaporated to dryness. The residue was taken up in 5 ml dichloromethane and 0.072 ml acetic acid and 1.00 g molecular sieve (powder, 4 Å) were added. To the resulting suspension was added 0.536 g triacetoxyborohydride, and the mixture was stirred 1 h at room temperature. Another 0.536 g triacetoxyborohydride was added and the mixture was stirred 1 h. The solids were removed by filtration over dicalite and the filtrate was purified by chromatography on silica gel with hexane:ethyl acetate=2:1 to yield 0.295 g of the title compound as a yellow solid melting at 113–114° C. after crystallisation from hexane.

g) (R)-8-Bromo-4,7-dimethyl-1,2,3,4-tetrahydro-pyrazino[1,2-a]indole hydrochloride A solution of 0.12 g (R)-8-bromo-4,7-dimethyl-1,2,3,4-tetrahydro-pyrazino[1,2-a]indole-2-carboxylic acid tert-butyl ester in 3 ml of a 2M solution of hydrochloric acid in ethyl acetate was stirred at room temperature under argon for 2 h. The precipitate was collected by filtration and dried to constant weight to yield the title compound (0.065 g) as off-white crystals. m.p.: 241° C. (dec.); ISP-MS: M+H=279.1; HNMR: (250 MHz, DMSO-d6, δ [ppm]) 1.50 (d, J=6.5 Hz, 3H); 2.45 (s, 3H); 3.48–3.74 (m, 2H); 4.36–4.58 (m, 2H); 4.74–4.89 (m, 1H); 6.35 (s, 1H); 7.54 (s, 1H); 7.78 (s, 1H)

h) (4R,10a R)-8-Bromo-4,7-dimethyl-1,2,3,4,10,10a-hexahydro-pyrazino[1,2-a]indole and (4R,10a S)-8-Bromo-4,7-dimethyl-1,2,3,4,10,10a-hexahydro-pyrazino[1,2-a]indole In analogy to example 12e) the title compounds were obtained from (R) 8-bromo-4,7-dimethyl-1,2,3,4-tetrahydro-pyrazino[1,2-a]indole; by reduction with sodium borohydride in the presence of trifluoroacetic acid. The diastereomeric products were separated by chromatography on silica gel. The more polar compound was assigned the trans configuration. The relative stereochemistry was determined on the basis of the proton NMR spectra and the rf. values.
ISP-MS: M+H=281.1 and 283.1

Examples 83 and 84

(4R,10aS) 4,7-Dimethyl-1,2,3,4,10,10a-hexahydro-pyrazino[1,2-a]indole and (4R,10aR) 4,7-Dimethyl-1,2,3,4,10,10a-hexahydro-pyrazino[1,2-a]indole a) (R)-4,7-Dimethyl-1,2,3,4-tetrahydro-pyrazino[1,2-a]indole-2-carboxylic acid tert-butyl ester To a solution of 1.52 g (R)-8-bromo-4,7-dimethyl-1,2,3,4-tetrahydro-pyrazino[1,2-a]indole-2-carboxylic acid tert-butyl ester in 15 ml ethanol was added 0.15 g 10% palladium on charcoal and the mixture was stirred under a hydrogen atmosphere for 6 h. A further 0.15 g 10% palladium on charcoal was added and the mixture was stirred a further 6 h under a hydrogen atmosphere. Again 0.15 g 10% palladium on charcoal was added and the mixture was stirred a further 6 h under a hydrogen atmosphere. The catalyst was removed by filtration over dicalite and the filtrate was evaporated. The residue was purified by chromatography on silica gel with hexane:ethyl acetate=4:1 to yield 0.59 g (R)-4,7-dimethyl-1,2,3,4-tetrahydro-pyrazino[1,2-a]indole-2-carboxylic acid tert-butyl ester as a white foam. MS: (M+H)=301.3.

b) (R)-4,7-Dimethyl-1,2,3,4-tetrahydro-pyrazino[1,2-a]indole hydrochloride

The title compound (MS: M+H=201.2; mp.: 245° C. (dec)) was produced in analogy with method of example 81 from (R)-4,7-dimethyl-1,2,3,4-tetrahydro-pyrazino[1,2-a]indole-2-carboxylic acid tert-butyl ester.HNMR: (250 MHz, DMSO-d6, δ [ppm]) 1.51 (d, J=6.5 Hz, 3H); 2.43 (s, 3H); 3.50–3.74 (m, 2H); 4.36–4.58 (m, 2H); 4.74–4.89 (m, 1H); 6.34 (s, 1H); 6.82 (d, J=7 Hz, 1H); 7.38 (s, 1H); 7.41 (d, J=7 Hz, 1H)

c) (4R,10aS) 4,7-Dimethyl-1,2,3,4,10,10a-hexahydro-pyrazino[1,2-a]indole and (4R,10aR) 4,7-Dimethyl-1,2,3,4,10,10a-hexahydro-pyrazino[1,2-a]indole In analogy to example 12e the title compounds were obtained from (R)-4,7-dimethyl-1,2,3,4-tetrahydro-pyrazino[1,2-a]indole-2-carboxylic acid tert-butyl ester; by reduction with sodium borohydride in the presence of trifluoroacetic acid. The diastereomeric products were separated by chromatography on silica gel. The more polar compound was assigned the trans configuration. The relative stereochemistry was determined on the basis of the proton NMR spectra and the rf. Values.
MS: M+H=203.2

Examples 85 and 86

(4R,10aR)-4,7,8-Trimethyl-1,2,3,4,10,10a-hexahydro-pyrazino[1,2-a]indole and (4R,10aS) 4,7,8-Trimethyl-1,2,3,4,10,10a-hexahydro-pyrazino[1,2-a]indole a) (R)-4,7,8-Trimethyl-1,2,3,4-tetrahydro-pyrazino[1,2-a]indole-2-carboxylic acid tert-butyl ester To a solution of 1.18 g (R)-8-bromo-4,7-dimethyl-1,2,3,4-tetrahydro-pyrazino[1,2-a]indole-2-carboxylic acid tert-butyl ester in 12 ml dioxane were added 0.36 g tetrakistriphenylphosphinpalladium, 1.29 g potassium carbonate and 0.39 trimethylboroxine and the mixture was heated 1 h at reflux. The reaction mixture was partitioned between water and ethyl acetate. The phases were separated and the organic phase was washed with 10% sodium bicarbonate, 10% citric acid and brine, dried over magnesium sulfate and purified by chromatography on silica gel with hexane:ethyl acetate=3:1 to yield 0.62 g (R)-4,7,8-trimethyl-1,2,3,4-tetrahydro-pyrazino[1,2-a]indole-2-carboxylic acid tert-butyl ester as slightly yellow foam. MS: (M+H)=315.4 b) (R)-4,7,8-Trimethyl-1,2,3,4-tetrahydro-pyrazino[1,2-a]indole

The title compound (MS: M+H=215.3) was produced in analogy with the method of example 81 from (R)-4,7,8-trimethyl-1,2,3,4-tetrahydro-pyrazino[1,2-a]indole-2-carboxylic acid tert-butyl ester. The material was isolated as the free amine base by chromatography on silica gel with dichloromethane:methanol:ammonia=9:1:0.1 in the form of a light yellow oil.

HNMR: (250 MHz, CDCl$_3$, δ [ppm]) 1.47 (d, J=6.5 Hz, 3H); 2.33 (s, 3H); 2.38 (s, 3H); 3.07–3.42 (m, 2H); 4.06–4.26 (m, 2H); 4.34–4.42 (m, 1H); 6.02 (s, 1H); 7.07 (s, 1H); 7.31 (s, 1H)

c) (4R,10aR) 4,7,8-Trimethyl-1,2,3,4,10,10a-hexahydro-pyrazino[1,2-a]indole and (4R,10aS) 4,7,8-Trimethyl-1,2,3, 4,10,10a-hexahydro-pyrazino[1,2-a]indole In analogy to example 12e) the title compounds were obtained from (R)-4,7,8-trimethyl-1,2,3,4-tetrahydro-pyrazino[1,2-a]indole-2-carboxylic acid tert-butyl ester; by reduction with sodium borohydride in the presence of trifluoroacetic acid. The diastereomeric products were separated by chromatography on silica gel. The more polar compound was assigned the trans configuration. The relative stereochemistry was determined on the basis of the proton NMR spectra and the rf. values.

MS: M+H=217.3

Example 87

(4R,10aR)-6,7-Dichloro-4-methyl-1,2,3,4,10,10a-hexahydro-pyrazino[1,2-a]indole a) (R)-6,7-Dichloro-4-methyl-3,4-dihydro-2H-pyrazino[1,2-a]indol-1-one The title compound, m/e=269.2 ([M+H]$^+$), was produced in accordance with the general method of example 14d) from 6,7-dichloro-1H-indole-2-carboxylic acid ethyl ester and (S)-5-methyl-2,2-dioxo-[1,2,3]oxathiazolidine-3-carboxylic acid tert-butyl ester. White solid.

b) (R)-6,7-Dichloro-4-methyl-1,2,3,4-tetrahydro-pyrazino[1,2-a]indole hydrochloride The title compound, m/e=255.1 ([M−Cl]$^+$), was produced in accordance with the general method of example 12d) from (R)-6,7-dichloro-4-methyl-3,4-dihydro-2H-pyrazino[1,2-a]indol-1-one and precipitated as the HCl salt. White solid.

c) (4R,10aR)-6,7-Dichloro-4-methyl-1,2,3,4,10,10a-hexahydro-pyrazino[1,2-a]indole The title compound, ISP-MS: m/e=257.0 ([M+H]$^+$), was produced in accordance with the general method of example 12e) from (R)-6,7-dichloro-4-methyl-1,2,3,4-tetrahydro-pyrazino[1,2-a]indole hydrochloride. Light brown oil.

Example 88

(4R,10aS)-8-Fluoro-4,6-dimethyl-1,2,3,4,10,10a-hexahydro-pyrazino[1,2-a]indole hydrochloride a) 7-Bromo-5-fluoro-1H-indole-2-carboxylic acid ethyl ester 2-Bromo-4-fluoro-phenylhydrazine (20 g, 0.097 mol) was dissolved in ethanol and the solution cooled to 0° C. (ice-bath). Ethyl pyruvate (11.3 ml, 0.101 mol) was added dropwise and the solution stirred 15 h at room temperature. The solvent was evaporated under reduced pressure, and the residue stirred with hexane. The mixture of hydrazones that formed upon cooling in an ice-bath was filtered and dried under vacuum. Yield 24.4 g, 82%. The hydrazone mixture (22 g, 0.073 mol) was dissolved in Eaton's reagent (230 ml) and the mixture heated 3 h at 50° C. The mixture was cooled to room temperature, diluted with dichloromethane and added to saturated aqueous sodium hydrogen carbonate. The phases were separated and the aqueous phase extracted twice with dichloromethane. The combined organic phases were washed with water, dried over magnesium sulfate and evaporated. The residue was taken up in diethyl ether, and hexane added whereupon part of the product precipitated. This was filtered and the mother liquor purified by column chromatography on silica gel (5:1 toluene/hexane eluant) to afford the product as a light yellow solid (14.1 g, 68%). Mp: 125° C., EI MS: 285.0 (M$^+$)

b) (R)-7-Bromo-1-(2-tert-butoxycarbonylamino-1-methyl-ethyl)-5-fluoro-1H-indole-2-carboxylic acid ethyl ester The title compound, ISP-MS: m/e=(M+H$^+$), was prepared in accordance with the general method of example 12b) from 7-bromo-5-fluoro-1H-indole-2-carboxylic acid ethyl ester (10.0 g, 0.035mol) and (S)-5-methyl-2,2-dioxo-[1,2,3] oxathiazolidine-3-carboxylic acid tert-butyl ester 10 g, 0.042 mol). The product was isolated as a viscous yellow oil, (10.1 g, 65%); ISP MS: 445.3 (M+H)$^+$ c) (R)-6-Bromo-8-fluoro-4-methyl-3,4-dihydro-2H-pyrazino[1,2-a]indol-1-one.

The title compound was prepared in accordance with the general method of example 12c) from (R)-7-Bromo-1-(2-tert-butoxycarbonylamino-1-methyl-ethyl)-5-fluoro-1H-indole-2-carboxylic acid ethyl ester(8.8 g, 0.0199 mol). Yield: 4.1 g, 70%) White solid, Mp: 188° C., ISP-MS: 297.2 (M+H)$^+$ d) (R)-8-Fluoro-4,6-dimethyl-1,2,3,4-tetrahydro-2H-pyrazino[1,2-a]indol-1-one (R)-6-Bromo-8-fluoro-4-methyl-3,4-dihydro-2H-pyrazino[1,2-a]indol-1-one 4.04 mMol) was dissolved in N,N-dimethylformamide under an argon atmosphere. Tetrakis(triphenylphosphine)palladium (0.45 g, 0.4 mMol) and potassium carbonate (1.56 g,12.11 mMol) were added. The mixture was stirred 5 min at room temperature before the addition of trimethylboroxine (0.55 ml, 4.04 mMol). The mixture was heated overnight at 110° C., cooled to room temperature and filtered over celite, washing with tetrahydrofuran. The solvents were evaporated to dryness and the residue purified by column chromatography on silica gel (1:1 to 3:1 ethyl acetate/toluene eluant) to afford the title compound as an off-white solid, (300 mg, 32%); ISP-MS: 233.1 (M+H$^+$)

e) (4R,10aS)-8-Fluoro-4,6-dimethyl-1,2,3,4,10,10a-hexahydro-pyrazino[1,2-a]indole hydrochloride The title compound was prepared in accordance with the general method of example 25f) from (R)-8-Fluoro-4,6-dimethyl-1,2,3,4-tetrahydro-2H-pyrazino[1,2-a]indol-1-one (106 mg), followed by conversion to the hydrochloride (Ethyl acetate/HCl). (Yield: 23 mg, 32%), light brown solid, ISP MS: 221.3 (M+H)$^+$

Example 89

(4R,10a R)-8-Bromo-7-fluoro-4methyl-1,2,3,4,10,10a-hexahydro-pyrazino[1,2-a]indole a) (4-Bromo-3-fluoro-phenyl)-carbamic acid methyl ester The title compound, m.p. 121–122° C., was prepared in accordance with the general method of example 81a) from 4-bromo-3-fluoroaniline and methyl chloroformate.

b) (4-Bromo-5-fluoro-2-iodo-phenyl)-carbamic acid methyl ester

The title compound, m.p. 101–102° C., was prepared in accordance with the general method of example 81b) from (4-bromo-3-fluoro-phenyl)-carbamic acid methyl ester.

c) 5-Bromo-2-[dimethyl-(1,1,2-trimethyl-propyl)-silanyloxymethyl]-6-fluoro-1H-indole The title compound, ISP-MS: m/e=302.0, 300.0 ([M+H]$^+$), was prepared in accordance with the general method of example 81c and d) from (4-bromo-5-fluoro-2-iodo-phenyl)-carbamic acid methyl ester.

d) (R)-8-Bromo-7-fluoro-4-methyl-3,4-dihydro-1H-pyrazino[1,2-a]indole-2-carboxylic acid tert-butyl ester The title compound, ISP-MS: m/e=383.2 ([M+H]$^+$) and m.p. 116–118° C., was prepared in accordance with the general method of example 81e and f) from 5-bromo-2-[dimethyl-(1,1,2-trimethyl-propyl)-silanyloxymethyl]-6-fluoro-1H-indole and (S)-5-methyl-2,2-dioxo-[1,2,3]oxathiazolidine-3-carboxylic acid tert-butyl ester.

e) (R)-8-Bromo-7-fluoro-4-methyl-1,2,3,4-tetrahydro-pyrazino[1,2-a]indole hydrochloride The title compound, m.p. 232° C., was prepared in accordance with the general method of example 81 g) from (R)-8-bromo-7-fluoro-4-methyl-3,4-dihydro-1H-pyrazino[1,2-a]indole-2-carboxylic acid tert-butyl ester.

f) (4R,10a R)-8-Bromo-7-fluoro-4methyl-1,2,3,4,10,10a-hexahydro-pyrazino[1,2-a]indole The title compound, ISP-MS: m/e=287.1, 285.0 ([M+H]$^+$), was prepared in accordance with the general method of example 81h) from (R)-8-bromo-7-fluoro-4-methyl-1,2,3,4-tetrahydro-pyrazino[1,2-a]indole and separated from its diastereomer by chromatography on silica gel.

Example 90

(4R,10a S)-8-Bromo-7-fluoro-4methyl-1,2,3,4,10,10a-hexahydro-pyrazino[1,2-a]indole The title compound, ISP-MS: m/e=287.1, 285.0 ([M+H]$^+$), was prepared in accordance with the general method of example 81h) from (R)-8-bromo-7-fluoro-4-methyl-1,2,3,4-tetrahydro-pyrazino[1,2-a]indole and separated from its diastereomer by chromatography on silica gel.

Example 91

(4R,10aR)-4-Methyl-1,2,3,4,10,10a-hexahydro-pyrazino 1,2-a]indole-7-carboxylic acid diethylamide hydrochloride a) (4R,10aR)-7-Diethylcarbamoyl-4-methyl-3,4,10,10a-tetrahydro-1H-pyrazino[1,2-a]indole-2-carboxylic acid tert-butyl ester The title compound; ISP-MS: m/e=388.3 (M+H$^+$), was prepared in accordance with the general method of example 79a) from (4R,10aR)-4-methyl-3,4,10,10a-tetrahydro-1H-pyrazino[1,2-a]indole-2,7-dicarboxylic acid 2-tert-butyl ester and N,N-diethylamine.

b) (4R,10aR)-4-Methyl-1,2,3,4,10,10a-hexahydro-pyrazino[1,2-a]indole-7-carboxylic acid diethylamide hydrochloride The title compound was prepared in accordance with the general method of example 78c) from (4R,10aR)-7-diethylcarbamoyl-4-methyl-3,4,10,10a-tetrahydro-1H-pyrazino[1,2-a]indole-2-carboxylic acid tert-butyl ester. Yellowish solid. M.p. 97° C. dec.;

ISP-MS: m/e=288.3 (M+H$^+$); $\alpha_D^{20}$=−36.8.

Example 92

(4R,10aR)-8-Fluoro-4,6-dimethyl-1,2,3,4,10,10a-hexahydro-pyrazino[1,2-a]indole; hydrochloride a) (R)-8-Fluoro-4,6-dimethyl-1,2,3,4-tetrahydro-pyrazino[1,2-a]indole; hydrochloride The title compound, ISP-MS: m/e=219.3 ([M−Cl]$^+$), was produced in accordance with the general method of example 12d) from (R)-8-fluoro-4,6-dimethyl-3,4,dihydro-pyrazino[1,2-a]indol-1-one and precipitated as HCl salt from diethylether solution. Light brown solid.

b) (4R,10aR)-8-Fluoro-4,6-dimethyl-1,2,3,4,10,10a-hexahydro-pyrazino[1,2-a]indole; hydrochloride The title compound, ISP-MS: m/e=221.2 ([M−Cl]$^+$) was produced in accordance with the general method of example 12e) from (R)-8-fluoro-4,6-dimethyl-1,2,3,4-tetrahydro-pyrazino[1,2-a]indole; hydrochloride. Light yellow solid.

Example 93

(4R,10aR)-7-Methoxymethyl-4-methyl-1,2,3,4,10,10a-hexahydro-pyrazino[1,2-a]indole a) (4R,10aR)-7-Methoxymethyl-4-methyl-3,4,10,10a-tetrahydro-1H-pyrazino[1,2-a]indole-2-carboxylic acid tert-butyl ester Sodium hydride (55–65% dispersion in mineral oil, 27 mg, 0.67 mmol) was added to a solution of (4R,10aR)-7-hydroxymethyl-4-methyl-3,4,10,10a-tetrahydro-1H-pyrazino[1,2-a]indole-2-carboxylic acid tert-butyl ester (200 mg, 0.63 mmol) in N,N-dimethylformamide (5 mL) at r.t., then after 1 h iodomethane (89 mg, 0.63 mmol) was added and the reaction mixture was stirred 2 h at 50° C. After cooling another portion of sodium hydride (27 mg, 0.67 mmol) was added, then after the addition of a second equivalent of iodomethane (89 mg, 0.63 mmol) the reaction mixture was stirred 2 h at 50° C. After cooling the reaction mixture was poured onto ice and extracted with ether (30 mL), the organic layer was washed with half-saturated brine, dried (MgSO$_4$), and concentrated. Chromatography on SiO$_2$ (Hexane/EtOAc 3:1) yielded the title compound (109 mg, 52%). Light yellow oil, ISP-MS: m/e=333.3 ([M+H]$^+$).

b) (4R,10aR)-7-Methoxymethyl-4-methyl-1,2,3,4,10,10a-hexahydro-pyrazino[1,2-a]indole The title compound, ISP-MS: m/e=233.2 ([M+H]$^+$), was produced in accordance with the general method of example 78c) from (4R,10aR)-7-methoxymethyl-4-methyl-3,4,10,10a-tetrahydro-1H-pyrazino[1,2-a]indole-2-carboxylic acid tert-butyl ester. Light yellow oil.

Example 94

(4R,10aR)-7-(2-Methoxy-ethoxymethyl)-4-methyl-1,2,3,4,10,10a-hexahydro-pyrazino[1,2-a]indole a) (4R,10aR)-7-(2-Methoxy-ethoxymethyl)-4-methyl-3,4,10,10a-tetrahydro-1H-pyrazino[1,2-a]indole-2-carboxylic acid tert-butyl ester The title compound, ISP-MS: m/e=377.4 ([M+H]$^+$), was produced in accordance with the general method of example 93a) from (4R,10aR)-7-hydroxymethyl-4-methyl-3,4,10,10a-tetrahydro-1H-pyrazino[1,2-a]indole-2-carboxylic acid tert-butyl ester and 2-bromoethyl methyl ether. Light yellow oil.

b) (4R,10aR)-7-(2-Methoxy-ethoxymethyl)-4-methyl-1,2,3,4,10,10a-hexahydro-pyrazino[1,2-a]indole The title compound, ISP-MS: m/e=277.3 ([M+H]$^+$), was produced in accordance with the general method of example 78c) from (4R,10aR)-7-methoxymethyl-4-methyl-3,4,10,10a-tetrahydro-1H-pyrazino[1,2-a]indole-2-carboxylic acid tert-butyl ester. Light yellow oil.

Example 95

(4R,10aR)-6-Bromo-4,7-dimethyl-1,2,3,4,10,10a-hexahydro-pyrazino[1,2-a]indole hydrochloride a) (2-Bromo-3-methyl-phenyl)-hydrazine The title compound, ISP-MS: m/e=184 and 186.1 (M-NH$_3$), was prepared in accordance with the general method of example 25a) from 2-bromo-3-methylaniline.

b) 2-[(2-Bromo-3-methyl-phenyl)-hydrazono]-propionic acid ethyl ester

The title compound, ISP-MS: m/e=299.3 and 301.3 (M+H$^+$), was prepared in accordance with the general method of example 25b) from (2-bromo-3-methyl-phenyl)-hydrazine and ethyl pyruvate.

c) 7-Bromo-6-methyl-1H-indole-2-carboxylic acid ethyl ester

The title compound, EI-MS: m/e=281.0 and 283.1 (M), was prepared in accordance with the general method of example 25c) from 2-[(2-bromo-3-methyl-phenyl)-hydrazono]-propionic acid ethyl ester.

d) (R)-7-Bromo-1-(2-tert-butoxycarbonylamino-1-methyl-ethyl)-6-methyl-1H-indole-2-carboxylic acid ethyl ester The title compound, ISP-MS: m/e=439.1 and 441.3 (M$^+$), was prepared in accordance with the general method of example 12b) from 7-bromo-6-methyl-1H-indole-2-carboxylic acid ethyl ester and (S)-5-methyl-2,2-dioxo-[1,2,3]oxathiazolidine-3-carboxylic acid tert-butyl ester.

e) (R)-6-Bromo-4,7-dimethyl-3,4-dihydro-2H-pyrazino[1,2-a]indol-1-one

The title compound, ISP-MS: m/e=291.2 and 293.2 (M$^+$), was prepared in accordance with the general method of example 12c) from (R)-7-bromo-1-(2-tert-butoxycarbonylamino-1-methyl-ethyl)-6-methyl-1H-indole-2-carboxylic acid ethyl ester.

f) (R)-6-Bromo-4,7-dimethyl-1,2,3,4-tetrahydro-pyrazino[1,2-a]indole

The title compound, ISP-MS: m/e=277.1 and 279.1 (M+H$^+$) was prepared in accordance with the general method of example 12d) from (R)-6-bromo-4,7-dimethyl-3,4-dihydro-2H-pyrazino[1,2-a]indol-1-one.

g) (4R,10aR)-6-Bromo-4,7-dimethyl-1,2,3,4,10,10a-hexahydro-pyrazino[1,2-a]indole hydrochloride The title compound, ISP-MS: m/e=281.2 and 283.2 (M$^+$) was prepared in accordance with the general method of example 12e) from (R)-6-bromo-4,7-dimethyl-1,2,3,4-tetrahydro-pyrazino[1,2-a]indole.

Examples 96 and 97

(4S,10aS)-(7-Trifluoromethyl-1,2,3,4,10,10a-hexahydro-pyrazino[1,2-a]indol-4-yl)-methanol and (4S,10aR)-(7-Trifluoromethyl-1,2,3,4,10,10a-hexahydro-pyrazino[1,2-a]indol-4-yl)-methanol a) (R)-5-[Dimethyl-(1,1,2-trimethyl-propyl)-silanyloxymethyl]-2,2-dioxo-[1,2,3]oxathiazolidine-3-carboxylic acid tert-butyl ester The title compound was prepared from (R)-{3-[dimethyl-(1,1,2-trimethyl-propyl)-silanyloxy]-2-hydroxy-propyl}-carbamic acid tert-butyl ester by the general method described in example 12a). It was purified by chromatography on silica gel with hexane ethyl acetate mixtures and obtained as viscous colorless oil. MS: m/e=396.1 (M$^+$). $\alpha_D^{20}$=+8.26 b) (S)-4-[Dimethyl-(1,1,2-trimethyl-propyl)-silanyloxymethyl]-7-trifluoromethyl-3,4-dihydro-2H-pyrazino[1,2-a]indol-1-one To a solution of 0.700 g ethyl 6-(trifluoromethyl)indole-2-carboxylate in 7 ml DMF was added 0.13 g sodium hydride 55% in oil and the mixture was stirred at room temperature for 30 min. To the resulting solution was added 1.30 g (R)-5-[Dimethyl-(1,1,2-trimethyl-propyl)-silanyloxymethyl]-2,2-dioxo-[1,2,3]oxathiazolidine-3-carboxylic acid tert-butyl ester and the mixture was stirred at room temperature for 18 h. The reaction mixture was distributed between 10% citric acid and dichloromethane and the organic phase was purified by chromatography on silica gel with dichloromethane. The product (1.15 g) was taken up in 11 ml TFA was stirred at 0° C. for 45 min. The solvent was evaporated and the residue was taken up in 10 ml methanol. To the resulting solution was added 1.00 g potassium carbonate and the mixture was stirred at room temperature for 3 h. The reaction mixture was purified by chromatography on silica gel with ethyl acetate to yield 0.36 g of the tiltle compound (m.p.: 143–144° C.) and 0.117 g of its desilylated analog (m.p.: 184–185° C.)

c) (S)-(7-Trifluoromethyl-1,2,3,4-tetrahydro-pyrazino[1,2-a]indol-4-yl)-methanol To a solution of 0.240 g (S)-4-[dimethyl-(1,1,2-trimethyl-propyl)-silanyloxymethyl]-7-trifluoromethyl-3,4-dihydro-2H-pyrazino[1,2-a]indol-1-one in 3 ml THF was added 1.2 ml of a 1M solution of lithium aluminum hydride in THF. The mixture was heated to reflux for 1 h. The reaction mixture was cooled to room temperature and the 10 ml ethyl acetate and 10 ml water was added. The phases were separated and the organic phase was purified by chromatography on silica gel with dichloromethane:methanol:25% aqueous ammonia=190:10:1 to yield 0.11 g of the tile compound as white crystals (m.p.: 126–127).

d) (4S,10aS)-(7-Trifluoromethyl-1,2,3,4,10,10a-hexahydro-pyrazino[1,2-a]indol-4-yl)-methanol and (4S,10aR)-(7-trifluoromethyl-1,2,3,4,10,10a-hexahydro-pyrazino[1,2-a]indol-4-yl)-methanol The title compounds of were obtained from (S)-(7-trifluoromethyl-1,2,3,4-tetrahydro-pyrazino[1,2-a]indol-4-yl)-methanol by the general procedure described in example 12e) by reduction with sodium borohydride in trifluoroacetic acid. The diastereomeric products were separated by chromatography on silica gel with dichloromethane:methanol: 25% aqueous ammonia=90:10:1. The more polar compound was assigned the trans configuration.

(4S,10aS)-Isomer: Light yellow gum. ISP-MS: m/e=273.2 ([M+H]$^+$).

(4S,10aR)-Isomer: Light yellow gum. ISP-MS: m/e=273.2 ([M+H]$^+$).

Example A

Tablets containing the following ingredients can be manufactured in a conventional manner:

| Ingredients | Per tablet |
| --- | --- |
| Compound of formula I | 10.0–100.0 mg |
| Lactose | 125.0 mg |
| Maize starch | 75.0 mg |
| Talc | 4.0 mg |
| Magnesium stearate | 1.0 mg |

Example B

Capsules containing the following ingredients can be manufactured in a conventional manner:

| Ingredients | Per capsule |
| --- | --- |
| Compound of formula I | 25.0 mg |
| Lactose | 150.0 mg |
| Maize starch | 20.0 mg |
| Talc | 5.0 mg |

Example C

Injection solutions can have the following composition:

| Compound of formula I | 3.0 mg |
| --- | --- |
| Gelatine | 150.0 mg |
| Phenol | 4.7 mg |
| Water for injection solutions | ad 1.0 ml |

What is claimed is:

1. A compound of formula I-C:

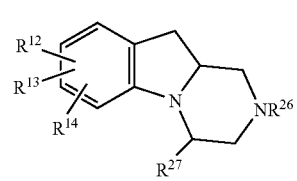

I-C wherein $R^{12}$, $R^{13}$ and $R^{14}$ are independently hydrogen, halogen, trifluoromethyl, lower alkyl, lower alkoxy lower alkyl, lower alkoxy lower alkoxy lower alkyl, halo lower alkoxy, lower alkyl aminocarbonyl or di-lower alkyl aminocarbonyl, cyano; $R^{26}$ is $(CH_2)_n$—Y, hydroxy lower alkyl, lower alkoxycarbonyl lower alkyl or carbamoyl lower alkyl;

$R^{27}$ is hydrogen or lower alkyl;

Y is oxazolidinone, cyclobutanonyl, [1,2,4]triazol-3-yl, [1,2,4]oxadiazol-3-yl, [1,2,4]triazol-3-one-5-yl, tetrazolyl, [1,3,4]oxadiazol-2-yl, [1,3,4]thiadiazol-2-yl, 1H-imidazol-2-yl or 1H-imidazol-4-yl; and n is 0, 1, 2 or 3.

2. The compound of claim 1 wherein said compound is (2S,10aR) and (2R,10aR)-2-(9-bromo-3,4,10,10a-tetrahydro-1H-pyrazino[1,2-a]indol-2-yl)-cyclobutanone.

3. The compound of claim 1 wherein said compound is (2S,10aS) and (2R,10aS)-2-(9-bromo-3,4,10,10a-tetrahydro-1H-pyrazino[1,2-a]indol-2-yl)-cyclobutanone.

4. The compound of claim 1 wherein said compound is (10aR)-3-(9-bromo-3,4,10,10a-tetrahydro-1H-pyrazino[1,2-a]indol-2-ylmethyl)-oxazolidin-2-one.

5. The compound of claim 1 wherein said compound is (10aS)-3-(9-bromo-3,4,10,10a-tetrahydro-1H-pyrazino[1,2-a]indol-2-ylmethyl)-oxazolidin-2-one.

6. The compound of claim 1 wherein said compound is (10aR)-2-(9-bromo-3,4,10,10a-tetrahydro-1H-pyrazino[1,2-a]indol-2-yl)-ethanol.

7. The compound of claim 1 wherein said compound is (10aR)-(9-bromo-3,4,10,10a-tetrahydro-1H-pyrazino[1,2-a]indol-2-yl)-acetic acid methyl ester.

8. The compound of claim 1 wherein said compound is (10aR)-2-(9-bromo-3,4,10,10a-tetrahydro-1H-pyrazino[1,2-a]indol-2-yl)-acetamide.

* * * * *